United States Patent
Cao et al.

(10) Patent No.: US 12,414,953 B2
(45) Date of Patent: Sep. 16, 2025

(54) SELECTIVE INHIBITORS OF PROTEIN ARGININE METHYLTRANSFERASE 5 (PRMT5)

(71) Applicant: Prelude Therapeutics, Incorporated, Wilmington, DE (US)

(72) Inventors: Ganfeng Cao, Chadds Ford, PA (US); Qun Li, Newark, DE (US); Huaping Zhang, Newark, DE (US); Hongwu Yu, Newark, DE (US)

(73) Assignee: Prelude Therapeutics, Incorporated, Willmington, DE (US)

( * ) Notice: Subject to any disclaimer, the term of this patent is extended or adjusted under 35 U.S.C. 154(b) by 712 days.

(21) Appl. No.: 17/761,717

(22) PCT Filed: Sep. 18, 2020

(86) PCT No.: PCT/US2020/051563
§ 371 (c)(1),
(2) Date: Mar. 18, 2022

(87) PCT Pub. No.: WO2021/055797
PCT Pub. Date: Mar. 25, 2021

(65) Prior Publication Data
US 2023/0029094 A1    Jan. 26, 2023

Related U.S. Application Data

(60) Provisional application No. 62/902,322, filed on Sep. 18, 2019.

(51) Int. Cl.
*A61K 31/519* (2006.01)
*A61P 35/00* (2006.01)

(52) U.S. Cl.
CPC ........ *A61K 31/519* (2013.01); *C07B 2200/13* (2013.01)

(58) Field of Classification Search
CPC .............................. A61K 31/315; A61P 35/00
USPC ...................................................... 514/258.1
See application file for complete search history.

(56) References Cited

FOREIGN PATENT DOCUMENTS

| | | |
|---|---|---|
| JP | 2017-525667 A | 9/2017 |
| JP | 2018-510850 A | 4/2018 |
| JP | 7328241 B | 8/2023 |
| WO | 2015200680 A2 | 12/2015 |
| WO | 2016/135582 A1 | 9/2016 |
| WO | 2017032840 A1 | 3/2017 |
| WO | 2017/153186 A1 | 9/2017 |
| WO | 2019032859 A1 | 2/2019 |
| WO | 2018/084470 A1 | 5/2019 |
| WO | 2019/178368 A1 | 9/2019 |

OTHER PUBLICATIONS

Chung et al. J Biol Chem 2013, 5534.
Hong Lin et al: "Discovery of Potent and Selective Covalent Protein Arginine Methyltransferase 5 (PRMT5) Inhibitors", ACS Medicinal Chemistry Letters, vol. 10, No. 7, May 22, 2019 (May 22, 2019), pp. 1033-1038, XP055663646, US ISSN: 1948-5875, DOI: 10.1021/acsmedchemlett.9b00074 abstract p. 1034, Scheme 1, compounds 9 and 10 figure 4; compounds 10, LLY-283.
Hsu et al. Nature 2015 525, 384.
Pal et al., Mol. Cell. Biol. 2003, 7475.
Pal et al. Mol. Cell. Biol. 2004, 9630.
Wang et al. Mol. Cell. Biol. 2008, 6262.
International Preliminary Report on Patentability for Application No. PCT/US2020/051563, mailed on Mar. 31, 2022, 10 pages.
International Search Report and Written Opinion issued in PCT/US2020/051563, dated Apr. 7, 2021, 12 pages.

*Primary Examiner* — Raymond J Henley, III
(74) *Attorney, Agent, or Firm* — Polsinelli PC

(57) ABSTRACT

The disclosure is directed to pharmaceutically acceptable salts of the compound of Formula I (I). Pharmaceutical compositions comprising pharmaceutically acceptable salts of the compound of Formula I, as well as methods of their use and preparation, are also described.

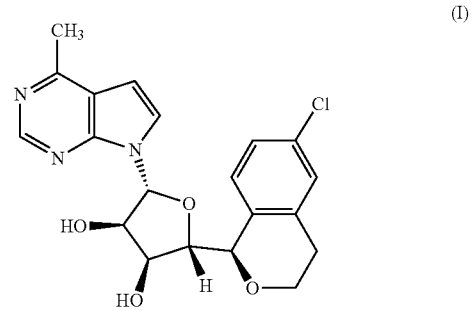

(I)

70 Claims, 24 Drawing Sheets

SELECTIVE INHIBITORS OF PROTEIN ARGININE METHYLTRANSFERASE 5 (PRMT5)

CROSS-REFERENCE TO RELATED APPLICATIONS

This application is the United States National Stage Application of International Patent Application No. PCT/US2020/051563, filed Sep. 18, 2020, which claims priority to U.S. Provisional Application No. 62/902,322 filed Sep. 18, 2019, the entirety of which is incorporated by reference herein.

TECHNICAL FIELD

The disclosure is directed to PRMT5 inhibitors and methods of their use.

BACKGROUND

Protein arginine methylation is a common post-translational modification that regulates numerous cellular processes, including gene transcription, mRNA splicing, DNA repair, protein cellular localization, cell fate determination, and signaling. Three types of methyl-arginine species exist: ω NG monomethylarginine (MMA), ω NG, NG asymmetric dimethylarginine (ADMA) and ω NG, N'G symmetric dimethylarginine (SDMA). The formation of methylated arginines is catalyzed by the protein arginine methyl transferases (PRMTs) family of methyltransferases. Currently, there are nine PRMTs annotated in the human genome. The majority of these enzymes are Type I enzymes (PRMT1, -2, -3, -4, -6, -8) that are capable of mono- and asymmetric dimethylation of arginine, with S-adenosylmethionine (SAM) as the methyl donor. PRMT-5, -7 and -9 are considered to be Type II enzymes that catalyze symmetric dimethylation of arginines. Each PRMT species harbors the characteristic motifs of seven beta strand methyltransferases (Katz et al., 2003), as well as additional "double E" and "THW" sequence motifs particular to the PRMT subfamily.

PRMT5 is as a general transcriptional repressor that functions with numerous transcription factors and repressor complexes, including BRG1 and hBRM, Blimp1, and Snail. This enzyme, once recruited to a promoter, symmetrically dimethylates H3R8 and H4R3. Importantly, the H4R3 site is a major target for PRMT1 methylation (ADMA) and is generally regarded as a transcriptional activating mark. Thus, both H4R3me2s (repressive; me2s indicates SDMA modification) and H4R3me2a (active; me2a indicates ADMA modification) marks are produced in vivo. The specificity of PRMT5 for H3R8 and H4R3 can be altered by its interaction with COPR5 and this could perhaps play an important role in determining PRMT5 corepressor status.

Role of PRMTs in Cancer

Aberrant expression of PRMTs has been identified in human cancers, and PRMTs are considered to be therapeutic targets. Global analysis of histone modifications in prostate cancer has shown that the dimethylation of histone H4R3 is positively correlated with increasing grade, and these changes are predictive of clinical outcome.

PRMT5 levels have been shown to be elevated in a panel of lymphoid cancer cell lines as well as mantle cell lymphoma clinical samples. PRMT5 interacts with a number of substrates that are involved in a variety of cellular processes, including RNA processing, signal transduction, and transcriptional regulation. PRMT5 can directly modify histone H3 and H4, resulting in the repression of gene expression. PRMT5 overexpression can stimulate cell growth and induce transformation by directly repressing tumor suppressor genes. Pal et al., Mol. Cell. Biol. 2003, 7475; Pal et al. Mol. Cell. Biol. 2004, 9630; Wang et al. Mol. Cell. Biol. 2008, 6262; Chung et al. J Biol Chem 2013, 5534. In addition to its well-documented oncogenic functions in transcription and translation, the transcription factor MYC also safeguards proper pre-messenger-RNA splicing as an essential step in lymphomagenesis. Koh et al. Nature 2015, 523 7558; Hsu et al. Nature 2015 525, 384.

The discovery of cancer dependencies has the potential to inform therapeutic strategies and to identify putative drug targets. Integrating data from comprehensive genomic profiling of cancer cell lines and from functional characterization of cancer cell dependencies, it has been recently discovered that loss of the enzyme methylthioadenosine phosphorylase (MTAP) confers a selective dependence on protein arginine methyltransferase 5 (PRMT5) and its binding partner WDR77. MTAP is frequently lost due to its proximity to the commonly deleted tumor suppressor gene, CDKN2A. Cells harboring MTAP deletions possess increased intracellular concentrations of methylthioadenosine (MTA, the metabolite cleaved by MTAP). Furthermore, MTA specifically inhibits PRMT5 enzymatic activity. Administration of either MTA or a small-molecule PRMT5 inhibitor shows a preferential impairment of cell viability for MTAP-null cancer cell lines compared to isogenic MTAP-expressing counterparts. Together, these findings reveal PRMT5 as a potential vulnerability across multiple cancer lineages augmented by a common "passenger" genomic alteration.

Role of PRMT5 in Hemoglobinopathies

The developmental switch in human globin gene subtype from fetal to adult that begins at birth heralds the onset of the hemoglobinopathies, b-thalassemia and sickle cell disease (SCD). The observation that increased adult globin gene expression (in the setting of hereditary persistence of fetal hemoglobin [HPFH] mutations) significantly ameliorates the clinical severity of thalassemia and SCD has prompted the search for therapeutic strategies to reverse gamma-globin gene silencing. Central to silencing of the gamma-genes is DNA methylation, which marks critical CpG dinucleotides flanking the gene transcriptional start site in adult bone marrow erythroid cells. It has been shown that these marks are established as a consequence of recruitment of the DNA methyltransferase, DNMT3A to the gamma-promoter by the protein arginine methyltransferase PRMT5. Zhao et al. Nat Struct Mol Biol. 2009 16, 304. PRMT5-mediated methylation of histone H4R3 recruits DNMT3A, coupling histone and DNA methylation in gene silencing.

PRMT5 induces the repressive histone mark, H4R3me2s, which serves as a template for direct binding of DNMT3A, and subsequent DNA methylation. Loss of PRMT5 binding or its enzymatic activity leads to demethylation of the CpG dinucleotides and gene activation. In addition to the H4R3me2s mark and DNA methylation, PRMT5 binding to the gamma-promoter, and its enzymatic activity are essential for assembly of a multiprotein complex on the gamma-promoter, which induces a range of coordinated repressive epigenetic marks. Disruption of this complex leads to reactivation of gamma gene expression. These studies provide the basis for developing PRMT5 inhibitors as targeted therapies for thalassemia and SCD.

SUMMARY

The disclosure is directed to pharmaceutically acceptable salts of a compound of Formula I:

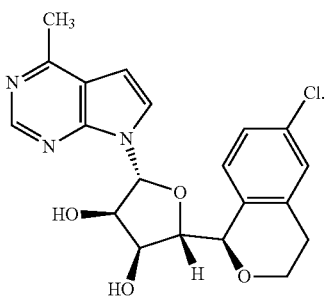

(I)

The disclosure is also directed to hydrochloride, phosphate, and tartrate salts of Formula I.

Crystalline forms of such salts, as well as pharmaceutical compositions and methods of use of such salts are also described.

DETAILED DESCRIPTION OF ILLUSTRATIVE EMBODIMENTS

Figure 1:
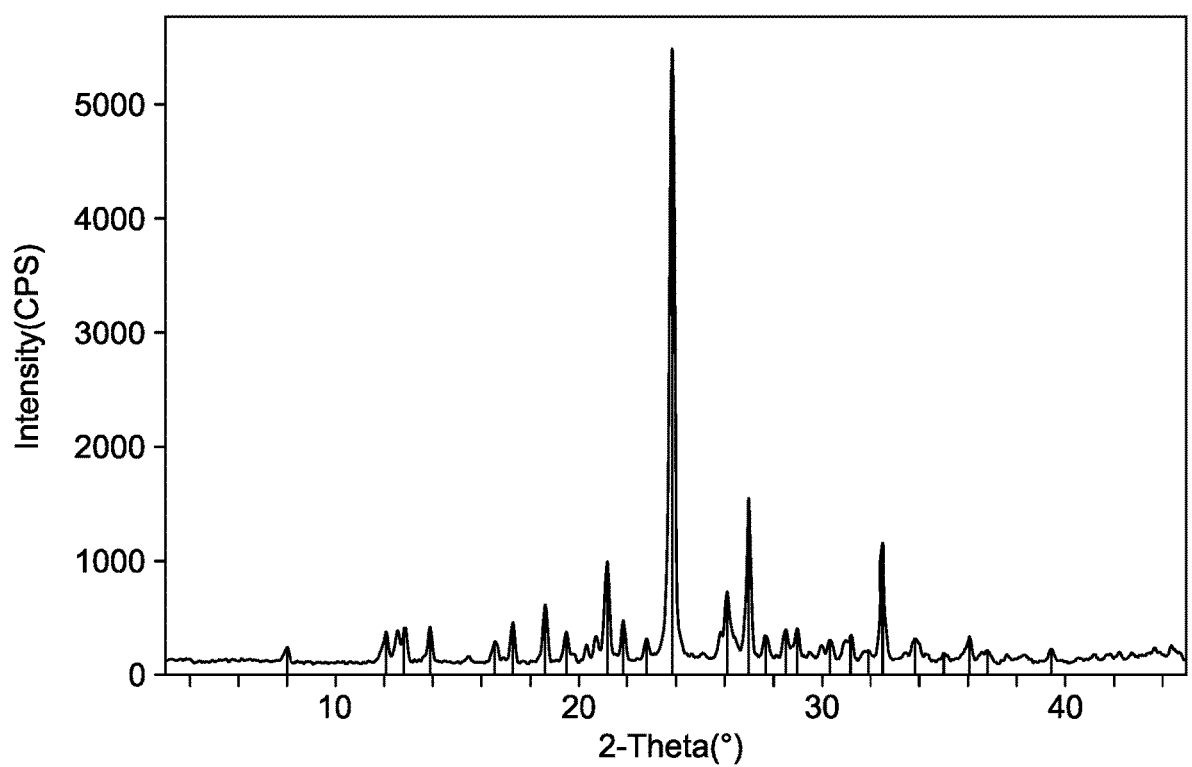
FIG. 1 shows an XRPD of Formula IA-Form I.

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, e.g., in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder. In some embodiments, "treating" or "treatment" refers to prophylactic treatment, i.e., preventing the onset of the disease or disorder.

"Compounds of the present disclosure," and equivalent expressions, are meant to embrace pharmaceutically acceptable salts of the compound of Formula I as described herein, as well as their subgenera, which expression includes the stereoisomers (e.g., entaniomers, diastereomers) and constitutional isomers (e.g., tautomers) where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

In some aspects, the disclosure is directed to pharmaceutically acceptable salts of a compound of Formula I:

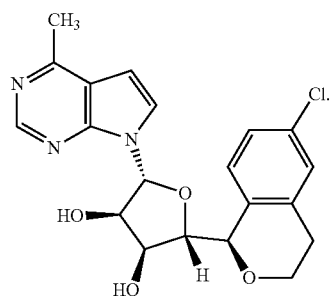

(I)

In some embodiments, the pharmaceutically acceptable salt is the phosphoric, sulfuric, hydrochloric, ascorbic, L-tartaric acid, ethane-1,2-disulfonic acid, or 1-hydroxy-2-naphthoic acid, and oxalic acids.

In some embodiments, the pharmaceutically acceptable salt of the compound of Formula I is the hydrochloride salt, i.e., Formula IA.

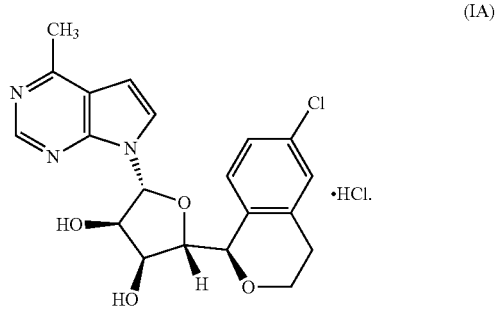 [SMILES: Cc1ncnc2c1ccn2[C@@H]1O[C@H]([C@@H]2OCCc3cc(Cl)ccc32)[C@@H](O)[C@H]1O]

(IA)

In other embodiments, the pharmaceutically acceptable salt of the compound of Formula I is the phosphate salt, i.e., Formula IB.

In other embodiments, the pharmaceutically acceptable salt of the compound of Formula I is the tartrate salt, i.e., Formula IC.

In some embodiments, the tartrate is L-tartrate. In other embodiments, the tartrate is D-tartrate.

In other embodiments, the pharmaceutically acceptable salt of the compound of Formula I is the sulfate salt, i.e., Formula ID.

In other embodiments, the pharmaceutically acceptable salt of the compound of Formula I is the ascorbate salt, i.e., Formula IE.

In other embodiments, the pharmaceutically acceptable salt of the compound of Formula I is the ethane-1,2-disulfonic acid salt, i.e., Formula IF.

In other embodiments, the pharmaceutically acceptable salt of the compound of Formula I is the 1-hydroxy-2-naphthoate salt, i.e., Formula IG.

In other embodiments, the pharmaceutically acceptable salt of the compound of Formula I is the oxalate, i.e., Formula IH.

In some aspects, the disclosure is directed to crystalline forms of pharmaceutically acceptable salts of Formula I.

In some embodiments, the disclosure is directed to crystalline forms of the salts of Formula IA, Formula IB, or Formula IC.

The crystalline forms of the salts of Formula IA, IB, or IC according to the present disclosure may have advantageous properties, including, one or more of chemical or polymorphic purity, flowability, solubility, dissolution rate, bioavailability, morphology, or crystal habit, stability—e.g., chemical stability, thermal stability, and mechanical stability with respect to polymorphic conversion, storage stability; hygroscopicity, low content of residual solvents, and advantageous processing and handling characteristics such as compressibility, or bulk density.

A crystal form may be referred to herein as being characterized by graphical data "as shown in" a Figure. Such data include, for example, powder X-ray diffractograms (XRPD), Differential Scanning calorimetry (DSC) thermograms, or thermogravimetric analysis (TGA) profiles. As is known in the art, the graphical data potentially provides additional technical information to further define the respective solid state form which can not necessarily be described by reference to numerical values or peak positions alone. Thus, the term "substantially as shown in" when referring to graphical data in a Figure herein means a pattern that is not necessarily identical to those depicted herein, but that falls within the limits of experimental error or deviations, when considered by one of ordinary skill in the art. The skilled person would readily be able to compare the graphical data in the Figures herein with graphical data generated for an unknown crystal form and confirm whether the two sets of graphical data are characterizing the same crystal form or two different crystal forms.

A solid, crystalline form may be referred to herein as "polymorphically pure" or as "substantially free of any other form." As used herein in this context, the expression "substantially free of any other forms" will be understood to mean that the solid form contains about 20% or less, about 10% or less, about 5% or less, about 2% or less, about 1% or less, or 0% of any other forms of the subject compound as measured, for example, by XRPD. For example, a solid form of Formula IA described herein as substantially free of any other solid forms would be understood to contain greater than about 80% (w/w), greater than about 90% (w/w), greater than about 95% (w/w), greater than about 98% (w/w), greater than about 99% (w/w), or about 100% of the subject solid form of Formula IA Accordingly, in some embodiments of the disclosure, the described solid forms of Formula IA may contain from about 1% to about 20% (w/w), from about 5% to about 20% (w/w), or from about 5% to about 10% (w/w) of one or more other solid forms of Formula IA.

As used herein, unless stated otherwise, XRPD peaks reported herein are measured using CuK$_\alpha$ radiation, $\lambda$=1.54 Å.

The modifier "about" should be considered as disclosing the range defined by the absolute values of the two endpoints. For example, the expression "from about 2 to about 4" also discloses the range "from 2 to 4." When used to modify a single number, the term "about" refers to plus or minus 10% of the indicated number and includes the indicated number. For example, "about 10%" indicates a range of 9% to 11%, and "about 1" means from 0.9-1.1.

In some aspects, the disclosure is directed to a crystalline form of the hydrochloride salt of Formula I, i.e., Formula IA. In some embodiments, the crystalline form of Formula IA is Form I (Formula IA-Form I). In some embodiments, Formula IA-Form I is substantially free of any other solid form of Formula IA.

In some embodiments, Formula IA-Form I exhibits an XRPD substantially as shown in FIG. 1. The XRPD of Formula IA-Form I shown in FIG. 1 comprises reflection angles (degrees 2-theta±0.2 degrees 2-theta), line spacings (d values), and relative intensities as shown in Table 1:

TABLE 1

XRPD Data for crystalline form of Formula IA-Form I shown in FIG. 1

| Angle (degrees 2-theta ± 0.2 degrees 2-theta) | d Value (Å) | Relative Intensity |
|---|---|---|
| 7.999 | 11.0435 | 2.5 |
| 12.08 | 7.3205 | 5 |
| 12.822 | 6.8986 | 5.4 |
| 13.88 | 6.3747 | 5.8 |
| 16.541 | 5.3549 | 3.6 |
| 17.28 | 5.1275 | 6.7 |
| 18.601 | 4.7662 | 9.7 |
| 19.48 | 4.5532 | 4.9 |

TABLE 1-continued

XRPD Data for crystalline form of Formula IA-Form I shown in FIG. 1

| Angle (degrees 2-theta ± 0.2 degrees 2-theta) | d Value (Å) | Relative Intensity |
|---|---|---|
| 21.18 | 4.1914 | 16.4 |
| 21.84 | 4.0662 | 6.4 |
| 22.781 | 3.9003 | 2.9 |
| 23.84 | 3.7293 | 100 |
| 26.1 | 3.4114 | 11 |
| 26.98 | 3.302 | 26.2 |
| 27.68 | 3.2201 | 3.4 |
| 28.5 | 3.1292 | 4.6 |
| 28.979 | 3.0786 | 4.8 |
| 30.32 | 2.9454 | 3.1 |
| 31.162 | 2.8678 | 3.8 |
| 31.88 | 2.8048 | 1.6 |
| 32.499 | 2.7527 | 19.5 |
| 33.84 | 2.6467 | 3.7 |
| 35.02 | 2.5602 | 1.4 |
| 36.06 | 2.4886 | 4.4 |
| 36.8 | 2.4403 | 2 |
| 39.421 | 2.2839 | 2.3 |

In some embodiments of the present disclosure, Formula IA-Form I is characterized by an XRPD pattern comprising a peak at one of the angles listed in Table 1. In other aspects, Formula IA-Form I is characterized by an XRPD pattern comprising more than one peak at one of the angles listed in Table 1 above. In other aspects, Formula IA-Form I is characterized by an XRPD pattern comprising two peaks selected from the angles listed in Table 1 above. In other aspects, Formula IA-Form I is characterized by an XRPD pattern comprising three peaks selected from the angles listed in Table 1 above. In other aspects, Formula IA-Form I is characterized by an XRPD pattern comprising four peaks selected from the angles listed in Table 1 above. In other aspects, Formula IA-Form I is characterized by an XRPD pattern comprising five peaks selected from the angles listed in Table 1 above. In other aspects, Formula IA-Form I is characterized by an XRPD pattern comprising six peaks selected from the angles listed in Table 1 above. In other aspects, Formula IA-Form I is characterized by an XRPD pattern comprising seven peaks selected from the angles listed in Table 1 above. In other aspects, Formula IA-Form I is characterized by an XRPD pattern comprising eight peaks selected from the angles listed in Table 1 above. In other aspects, Formula IA-Form I is characterized by an XRPD pattern comprising nine peaks selected from the angles listed in Table 1 above. In other aspects, Formula IA-Form I is characterized by an XRPD pattern comprising ten peaks selected from the angles listed in Table 1 above. In other aspects, Formula IA-Form I is characterized by an XRPD pattern comprising more than ten peaks selected from the angles listed in Table 1 above.

In some embodiments, Formula IA-Form I is characterized by an XRPD pattern comprising a peak at 23.8 degrees±0.2 degrees 2-theta. In other embodiments, Formula IA-Form I is characterized by an XRPD pattern comprising peaks at 21.2 and 23.8 degrees±0.2 degrees 2-theta. In other embodiments, Formula IA-Form I is characterized by an XRPD pattern comprising peaks at 21.2, 23.8, and 27.0 degrees±0.2 degree 2-theta. In other embodiments, Formula IA-Form I is characterized by an XRPD pattern comprising peaks at 21.2, 23.8, 27.0, and 32.5 degrees±0.2 degree 2-theta.

In some embodiments of the present disclosure, Formula IA-Form I is characterized by an XRPD pattern comprising peaks at two or more of 21.2, 23.8, 27.0, and 32.5 degrees±0.2 degrees 2-theta.

Figure 2:
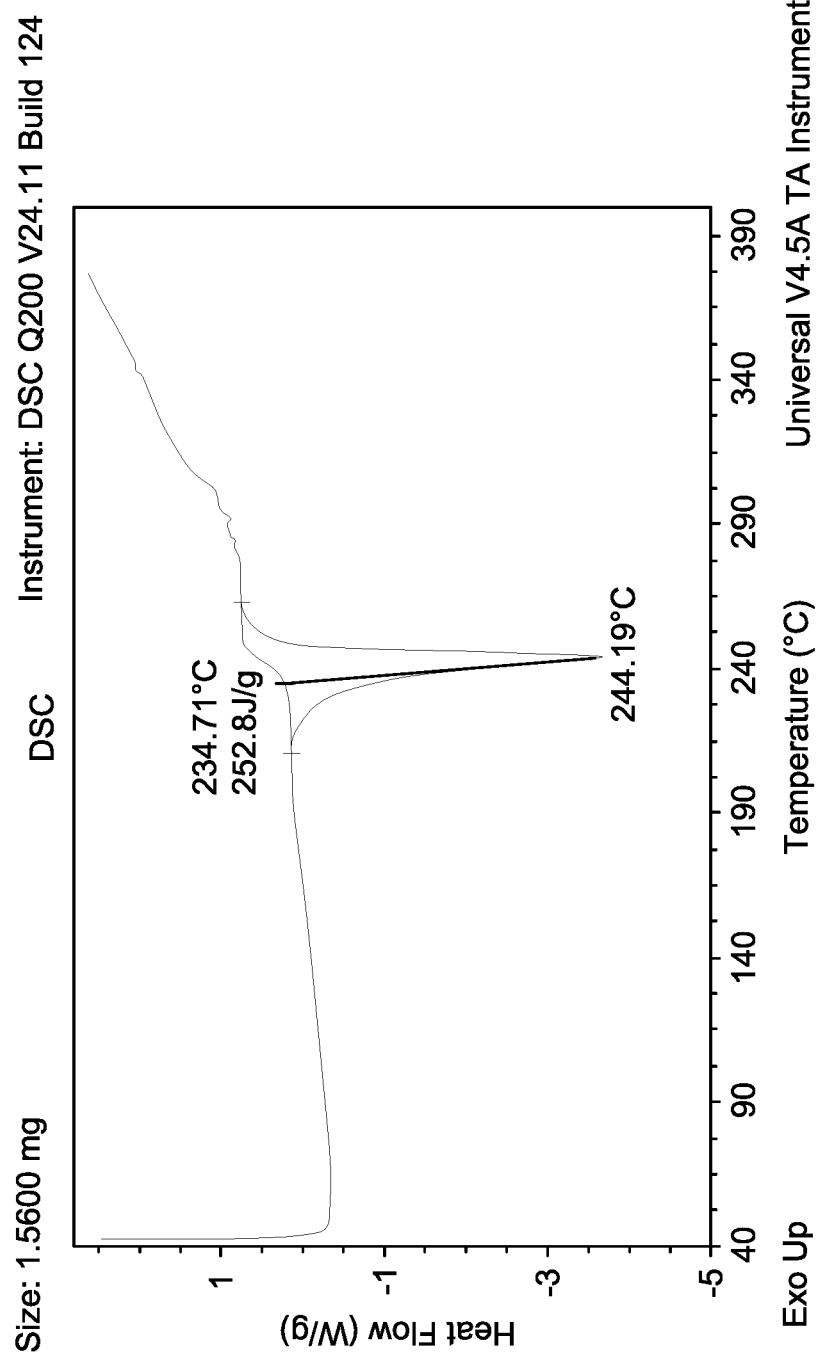
FIG. 2 shows a DSC thermogram of Formula IA-Form I.

In some embodiments, Formula IA-Form I can be characterized by a DSC thermogram substantially as shown in FIG. 2. As FIG. 2 shows, Formula IA-Form I produced an endothermic peak at 244.19° C., with a peak onset temperature of 234.71° C., and an enthalpy of melting of 252.8 J/g, when heated at a rate of 10° C./min. In some embodiments of the present disclosure, Formula IA-Form I is characterized by a DSC thermogram comprising an endothermic peak at about 244° C. In other embodiments of the present disclosure, Formula IA-Form I is characterized by a DSC enthalpy of melting of about 253 J/g.

Figure 3:
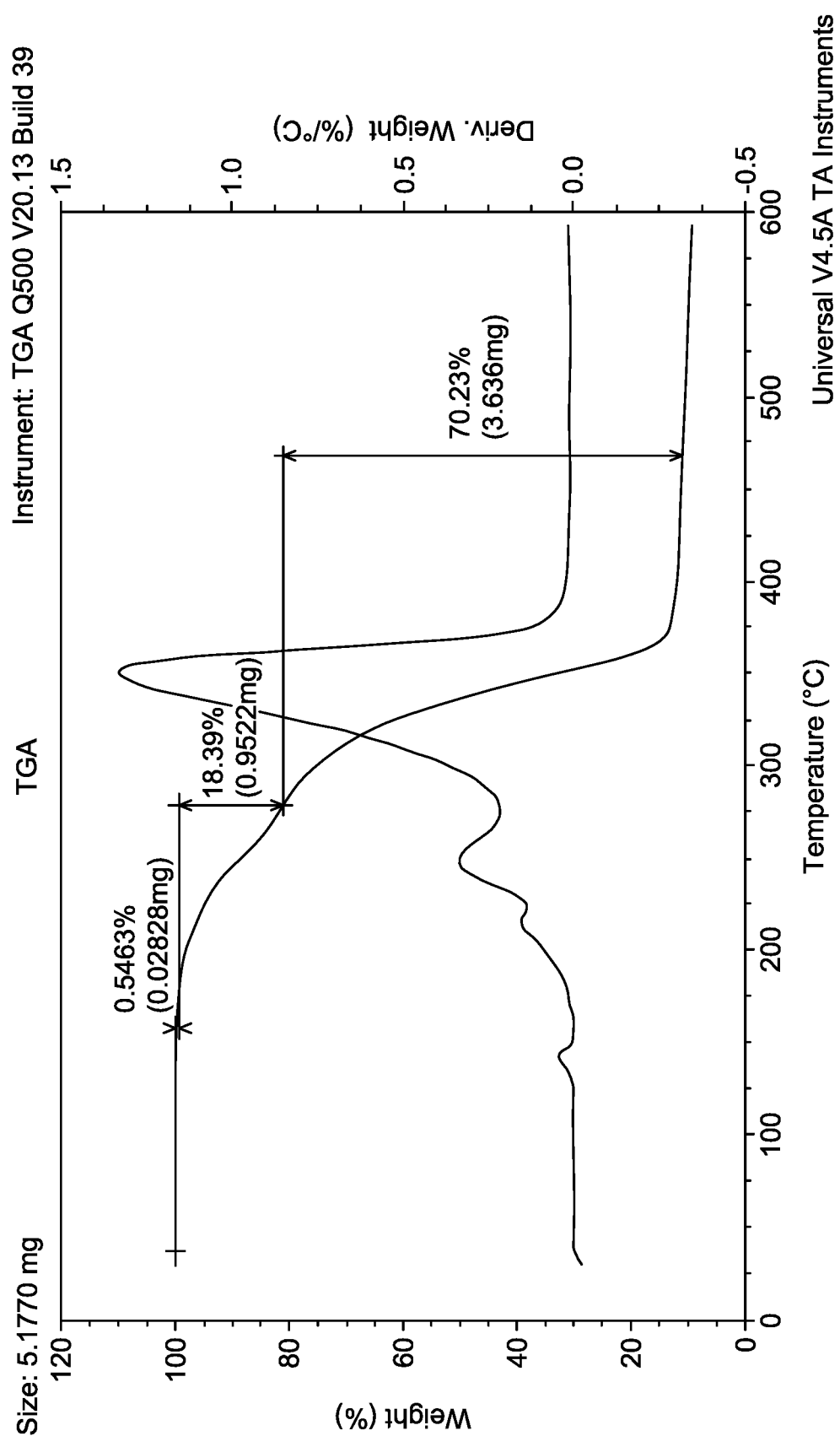
FIG. 3 shows a TGA profile of Formula IA-Form I.

In some embodiments, Formula IA-Form I can be characterized by a TGA profile substantially as shown in FIG. 3 when heated at a rate of 20° C./min. As FIG. 3 shows, Formula IA-Form I lost about 18.4% of its weight upon heating to about 300° C.

In some embodiments of the present disclosure, Formula IA-Form I is characterized by an XRPD pattern comprising peaks at one or more of 21.2, 23.8, 27.0, and 32.5 degrees±0.2 degrees 2-theta, and a DSC thermogram comprising an endothermic peak at about 244° C. when heated at a rate of 10° C./min.

In some embodiments, the crystalline form of Formula IA is Form II (Formula IA-Form II). In some embodiments, Formula IA-Form II is substantially free of any other solid form of Formula IA.

Figure 4:
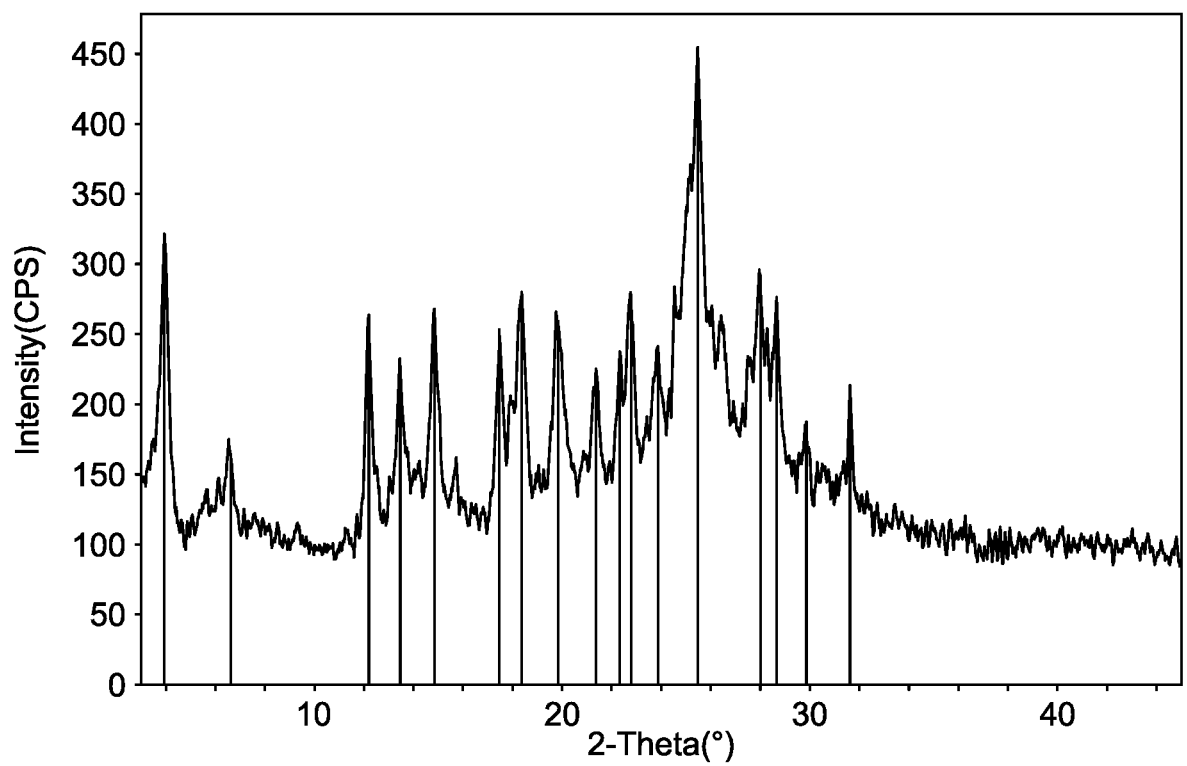
FIG. 4 shows an XRPD of Formula IA-Form II.

In some embodiments, Formula IA-Form II exhibits an XRPD substantially as shown in FIG. 4. The XRPD of Formula IA-Form II shown in FIG. 4 comprises reflection angles (degrees 2-theta±0.2 degrees 2-theta), line spacings (d values), and relative intensities as shown in Table 2:

TABLE 2

XRPD Data for crystalline form of Formula IA-Form II shown in FIG. 4

| Angle (degrees 2-theta ± 0.2 degrees 2-theta) | d Value (Å) | Relative Intensity |
| --- | --- | --- |
| 3.94 | 22.4059 | 73.3 |
| 6.618 | 13.3443 | 20.7 |
| 12.199 | 7.2496 | 58.1 |
| 13.458 | 6.574 | 37.4 |
| 14.839 | 5.9649 | 51.1 |
| 17.462 | 5.0746 | 50.4 |
| 18.36 | 4.8281 | 55.2 |
| 19.84 | 4.4713 | 44.8 |
| 21.361 | 4.1562 | 31.1 |
| 22.341 | 3.9761 | 32.2 |
| 22.778 | 3.9007 | 45.2 |
| 23.877 | 3.7236 | 24.1 |
| 25.46 | 3.4955 | 100 |
| 28.019 | 3.1819 | 47.4 |
| 28.66 | 3.1122 | 45.2 |
| 29.858 | 2.99 | 19.6 |
| 31.62 | 2.8272 | 35.2 |

In some embodiments of the present disclosure, Formula IA-Form II is characterized by an XRPD pattern comprising a peak at one of the angles listed in Table 2. In other aspects, Formula IA-Form II is characterized by an XRPD pattern comprising more than one peak at one of the angles listed in Table 2 above. In other aspects, Formula IA-Form II is characterized by an XRPD pattern comprising two peaks selected from the angles listed in Table 2 above. In other aspects, Formula IA-Form II is characterized by an XRPD pattern comprising three peaks selected from the angles listed in Table 2 above. In other aspects, Formula IA-Form II is characterized by an XRPD pattern comprising four peaks selected from the angles listed in Table 2 above. In other aspects, Formula IA-Form II is characterized by an XRPD pattern comprising five peaks selected from the angles listed in Table 2 above. In other aspects, Formula IA-Form II is characterized by an XRPD pattern comprising six peaks selected from the angles listed in Table 2 above. In other aspects, Formula IA-Form II is characterized by an XRPD pattern comprising seven peaks selected from the angles listed in Table 2 above. In other aspects, Formula IA-Form II is characterized by an XRPD pattern comprising eight peaks selected from the angles listed in Table 2 above. In other aspects, Formula IA-Form II is characterized by an XRPD pattern comprising nine peaks selected from the angles listed in Table 2 above. In other aspects, Formula IA-Form II is characterized by an XRPD pattern comprising ten peaks selected from the angles listed in Table 2 above. In other aspects, Formula IA-Form II is characterized by an XRPD pattern comprising more than ten peaks selected from the angles listed in Table 2 above.

In some embodiments, Formula IA-Form II is characterized by an XRPD pattern comprising a peak at 25.5 degrees±0.2 degrees 2-theta. In other embodiments, Formula IA-Form II is characterized by an XRPD pattern comprising peaks at 14.8, 17.5, and 25.5 degrees±0.2 degrees 2-theta. In other embodiments, Formula IA-Form II is characterized by an XRPD pattern comprising peaks at 14.8, 17.5, 18.4, 24.0, and 25.5 degrees±0.2 degree 2-theta. In other embodiments, Formula IA-Form II is characterized by an XRPD pattern comprising peaks at 14.8, 17.5, 18.4, 24.0, 25.5, 28.0, and 28.7 degrees±0.2 degree 2-theta. In other embodiments, Formula IA-Form II is characterized by an XRPD pattern comprising peaks at 17.5, 18.4, 19.8, 24.0, 25.5, 28.0, and 28.7 degrees±0.2 degree 2-theta.

In some embodiments of the present disclosure, Formula IA-Form II is characterized by an XRPD pattern comprising peaks at three or more of 17.5, 18.4, 19.8, 24.0, 25.5, 28.0, and 28.7 degrees±0.2 degrees 2-theta. In some embodiments of the present disclosure, Formula IA-Form II is characterized by an XRPD pattern comprising peaks at four or more of 17.5, 18.4, 19.8, 24.0, 25.5, 28.0, and 28.7 degrees±0.2 degrees 2-theta. In some embodiments of the present disclosure, Formula IA-Form II is characterized by an XRPD pattern comprising peaks at five or more of 17.5, 18.4, 19.8, 24.0, 25.5, 28.0, and 28.7 degrees±0.2 degrees 2-theta. In some embodiments of the present disclosure, Formula IA-Form II is characterized by an XRPD pattern comprising peaks at six or more of 17.5, 18.4, 19.8, 24.0, 25.5, 28.0, and 28.7 degrees±0.2 degrees 2-theta.

Figure 5:
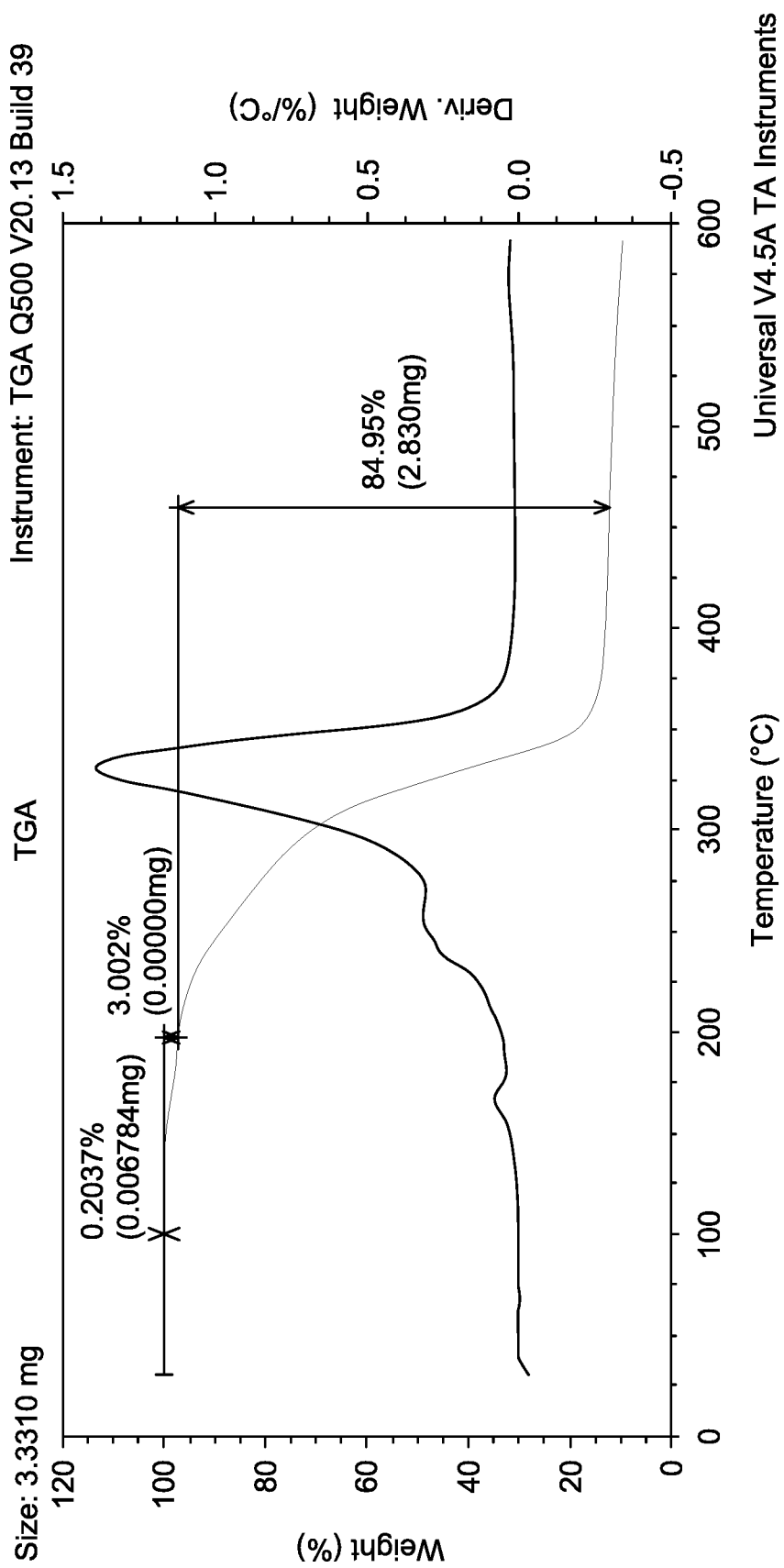
FIG. 5 shows a TGA profile of Formula IA-Form II.

In some embodiments, Formula IA-Form II can be characterized by a TGA profile substantially as shown in FIG. 5 when heated at a rate of 20° C./min. As FIG. 5 shows, Formula IA-Form II lost about 3% of its weight upon heating to about 225° C.

In some embodiments, the crystalline form of Formula IA is Form IIa (Formula IA-Form IIa). In some embodiments, Formula IA-Form IIa is substantially free of any other solid form of Formula IA.

Figure 6:
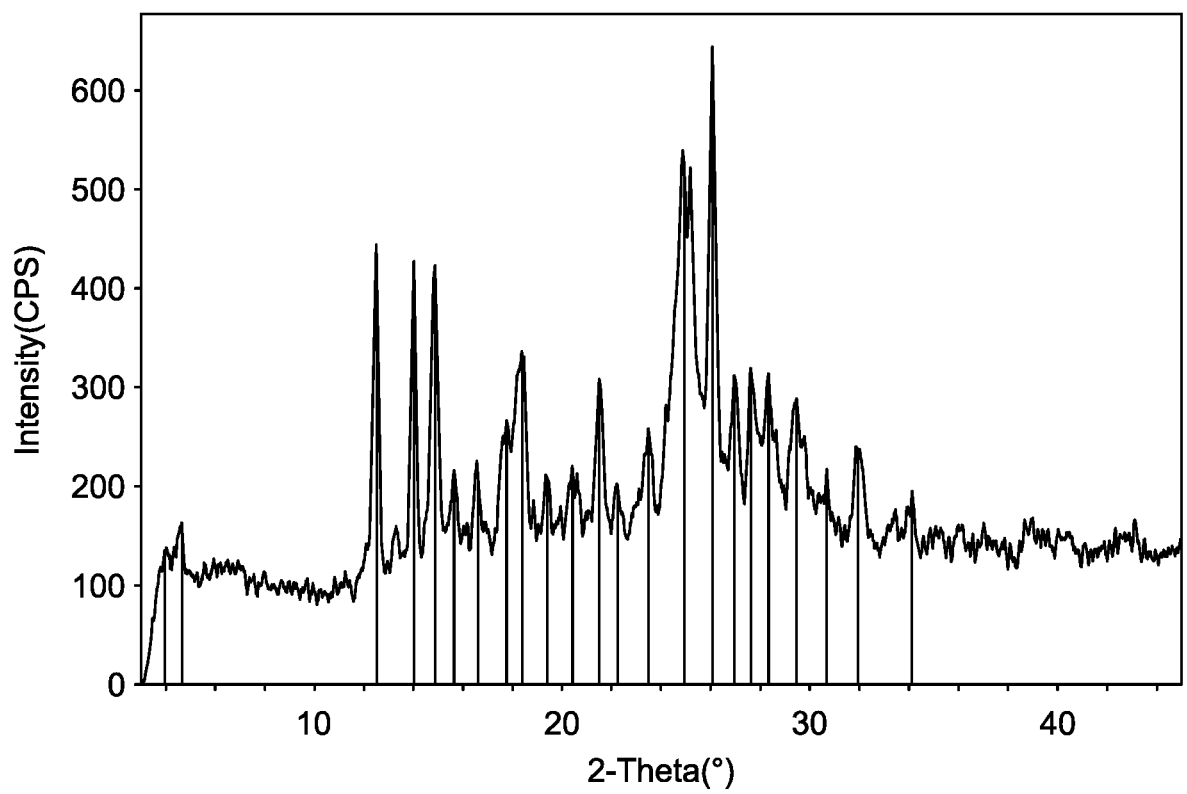
FIG. 6 shows an XRPD of Formula IA-Form IIa.

In some embodiments, Formula IA-Form IIa exhibits an XRPD substantially as shown in FIG. 6. The XRPD of Formula IA-Form IIa shown in FIG. 6 comprises reflection angles (degrees 2-theta±0.2 degrees 2-theta), line spacings (d values), and relative intensities as shown in Table 3:

TABLE 3

XRPD Data for crystalline form of Formula IA-Form IIa shown in FIG. 6

| Angle (degrees 2-theta ± 0.2 degrees 2-theta) | d Value (Å) | Relative Intensity |
|---|---|---|
| 3.96 | 22.2923 | 34.6 |
| 4.639 | 19.0309 | 42.1 |
| 12.519 | 7.0649 | 89.3 |
| 14.02 | 6.3117 | 79.3 |
| 14.879 | 5.9489 | 76.2 |
| 15.64 | 5.6613 | 22.5 |
| 16.597 | 5.337 | 21.5 |
| 17.76 | 4.9899 | 33.5 |
| 18.38 | 4.823 | 50.5 |
| 19.4 | 4.5717 | 17 |
| 20.418 | 4.3461 | 17 |
| 21.5 | 4.1296 | 41.9 |
| 22.257 | 3.9909 | 12.3 |
| 23.481 | 3.7856 | 24.3 |
| 24.938 | 3.5675 | 81.9 |
| 26.08 | 3.4139 | 100 |
| 26.962 | 3.3042 | 27.5 |
| 27.638 | 3.2248 | 32.2 |
| 28.339 | 3.1466 | 34.6 |
| 29.46 | 3.0294 | 29.3 |
| 30.683 | 2.9114 | 14.7 |
| 31.94 | 2.7997 | 27.2 |
| 34.122 | 2.6255 | 16.5 |

In some embodiments of the present disclosure, Formula IA-Form IIa is characterized by an XRPD pattern comprising a peak at one of the angles listed in Table 3. In other aspects, Formula IA-Form IIa is characterized by an XRPD pattern comprising more than one peak at one of the angles listed in Table 3 above. In other aspects, Formula IA-Form IIa is characterized by an XRPD pattern comprising two peaks selected from the angles listed in Table 3 above. In other aspects, Formula IA-Form IIa is characterized by an XRPD pattern comprising three peaks selected from the angles listed in Table 3 above. In other aspects, Formula IA-Form IIa is characterized by an XRPD pattern comprising four peaks selected from the angles listed in Table 3 above. In other aspects, Formula IA-Form IIa is characterized by an XRPD pattern comprising five peaks selected from the angles listed in Table 3 above. In other aspects, Formula IA-Form IIa is characterized by an XRPD pattern comprising six peaks selected from the angles listed in Table 3 above. In other aspects, Formula IA-Form IIa is characterized by an XRPD pattern comprising seven peaks selected from the angles listed in Table 3 above. In other aspects, Formula IA-Form IIa is characterized by an XRPD pattern comprising eight peaks selected from the angles listed in Table 3 above. In other aspects, Formula IA-Form IIa is characterized by an XRPD pattern comprising nine peaks selected from the angles listed in Table 3 above. In other aspects, Formula IA-Form IIa is characterized by an XRPD pattern comprising ten peaks selected from the angles listed in Table 3 above. In other aspects, Formula IA-Form IIa is characterized by an XRPD pattern comprising more than ten peaks selected from the angles listed in Table 3 above.

In some embodiments, Formula IA-Form IIa is characterized by an XRPD pattern comprising a peak at 26.1 degrees±0.2 degrees 2-theta. In other embodiments, Formula IA-Form IIa is characterized by an XRPD pattern comprising peaks at 14.0, 14.9, and 26.1 degrees±0.2 degrees 2-theta. In other embodiments, Formula IA-Form IIa is characterized by an XRPD pattern comprising peaks at 12.5, 14.0, 14.9, 18.4, and 26.1 degrees±0.2 degree 2-theta. In other embodiments, Formula IA-Form IIa is characterized by an XRPD pattern comprising peaks at 12.5, 14.0, 14.9, 18.4, 24.9, and 26.1 degrees±0.2 degree 2-theta. In other embodiments, Formula IA-Form IIa is characterized by an XRPD pattern comprising peaks at 12.5, 14.0, 14.9, 18.4, 24.9, 26.1 and 28.3 degrees±0.2 degree 2-theta.

In some embodiments of the present disclosure, Formula IA-Form IIa is characterized by an XRPD pattern comprising peaks at three or more of 12.5, 14.0, 14.9, 18.4, 24.9, 26.1 and 28.3 degrees±0.2 degrees 2-theta. In some embodiments of the present disclosure, Formula IA-Form IIa is characterized by an XRPD pattern comprising peaks at four or more of 12.5, 14.0, 14.9, 18.4, 24.9, 26.1 and 28.3 degrees±0.2 degrees 2-theta. In some embodiments of the present disclosure, Formula IA-Form IIa is characterized by an XRPD pattern comprising peaks at five or more of 12.5, 14.0, 14.9, 18.4, 24.9, 26.1 and 28.3 degrees±0.2 degrees 2-theta. In some embodiments of the present disclosure, Formula IA-Form IIa is characterized by an XRPD pattern comprising peaks at six or more of 12.5, 14.0, 14.9, 18.4, 24.9, 26.1 and 28.3 degrees±0.2 degrees 2-theta.

Figure 7:
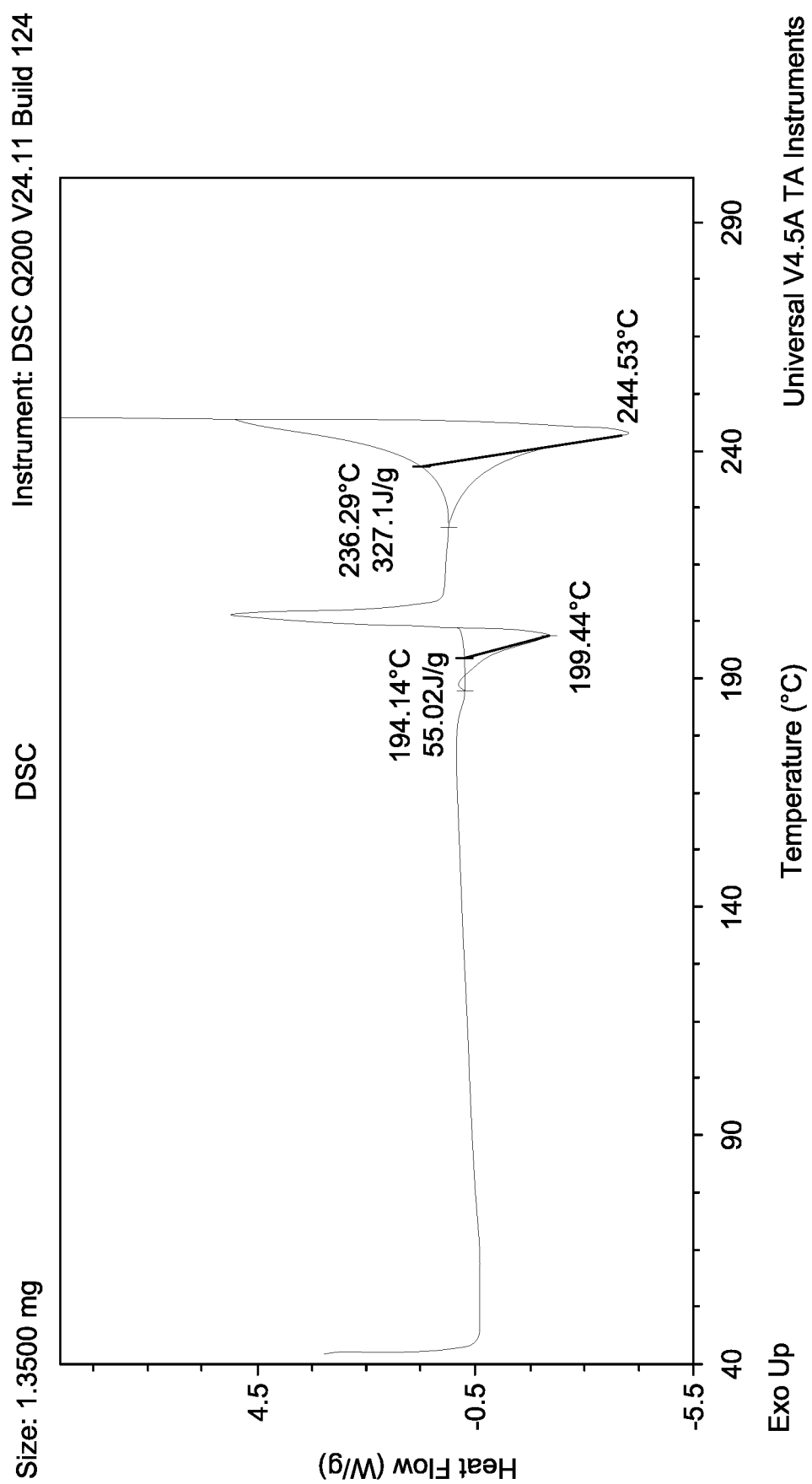
FIG. 7 shows a DSC thermogram of Formula IA-Form IIa.

In some embodiments, Formula IA-Form IIa can be characterized by a DSC thermogram substantially as shown in FIG. 7. As FIG. 7 shows, Formula IA-Form IIa produced an endothermic peak at 199.44° C., with a peak onset temperature of 194.14° C., and an enthalpy of melting of 55.02 J/g; followed by an exothermic peak; followed by an endothermic peak at 244.53° C., with a peak onset temperature of 236.29° C., and an enthalpy of melting of 327.1 J/g when heated at a rate of 10° C./min. In some embodiments of the present disclosure, Formula IA-Form IIa is characterized by a DSC thermogram comprising an endothermic peak at about 199° C. In other embodiments of the present disclosure, Formula IA-Form IIa is characterized by a DSC enthalpy of melting of about 55 J/g.

In some embodiments of the present disclosure, Formula IA-Form IIa is characterized by an XRPD pattern comprising peaks at one or more of 12.5, 14.0, 14.9, 18.4, 24.9, 26.1 and 28.3 degrees±0.2 degrees 2-theta, and a DSC thermogram comprising an endothermic peak at about 199° C. when heated at a rate of 10° C./min.

In some embodiments, the crystalline form of Formula IA is Form III (Formula IA-Form III). In some embodiments, Formula IA-Form III is substantially free of any other solid form of Formula IA.

Figure 8:
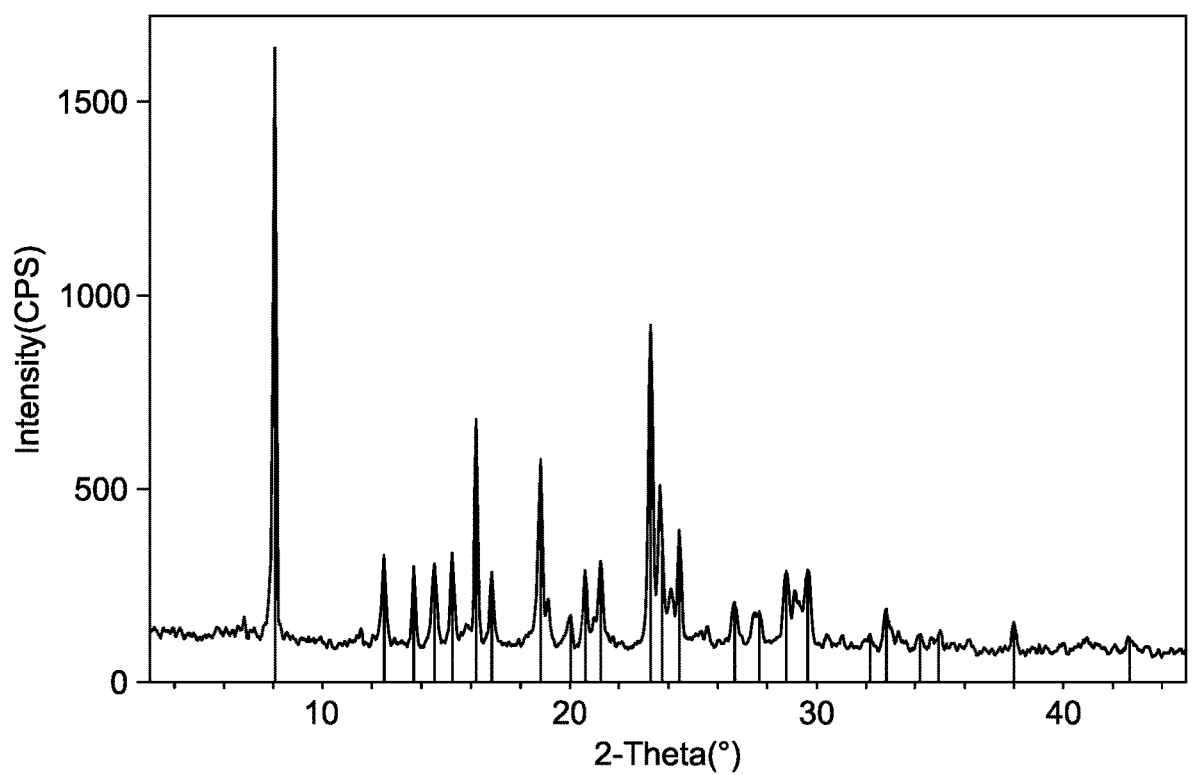
FIG. 8 shows an XRPD of Formula IA-Form III.

In some embodiments, Formula IA-Form III exhibits an XRPD substantially as shown in FIG. 8. The XRPD of Formula IA-Form III shown in FIG. 8 comprises reflection angles (degrees 2-theta±0.2 degrees 2-theta), line spacings (d values), and relative intensities as shown in Table 4:

TABLE 4

XRPD Data for crystalline form of Formula IA-Form III shown in FIG. 8

| Angle (degrees 2-theta ± 0.2 degrees 2-theta) | d Value (Å) | Relative Intensity |
|---|---|---|
| 8.059 | 10.9618 | 100 |
| 12.499 | 7.0758 | 15.4 |
| 13.7 | 6.4584 | 13.5 |
| 14.54 | 6.0872 | 13.5 |
| 15.26 | 5.8014 | 15.5 |
| 16.219 | 5.4606 | 37.8 |
| 16.841 | 5.2602 | 12.4 |
| 18.82 | 4.7113 | 31.5 |
| 20.038 | 4.4276 | 5.5 |
| 20.659 | 4.2958 | 13.1 |
| 21.279 | 4.172 | 14.9 |

TABLE 4-continued

XRPD Data for crystalline form of Formula IA-Form III shown in FIG. 8

| Angle (degrees 2-theta ± 0.2 degrees 2-theta) | d Value (Å) | Relative Intensity |
|---|---|---|
| 23.3 | 3.8146 | 54.4 |
| 23.774 | 3.7395 | 15.6 |
| 24.46 | 3.6362 | 19.1 |
| 26.699 | 3.3361 | 7.3 |
| 27.681 | 3.22 | 5.4 |
| 28.78 | 3.0995 | 12.2 |
| 29.641 | 3.0114 | 12.6 |
| 32.16 | 2.781 | 2.6 |
| 32.839 | 2.7251 | 7.1 |
| 34.2 | 2.6196 | 2.7 |
| 34.964 | 2.5641 | 2.8 |
| 38.018 | 2.3649 | 5.4 |
| 42.678 | 2.1168 | 2.6 |

In some embodiments of the present disclosure, Formula IA-Form III is characterized by an XRPD pattern comprising a peak at one of the angles listed in Table 4. In other aspects, Formula IA-Form III is characterized by an XRPD pattern comprising more than one peak at one of the angles listed in Table 4 above. In other aspects, Formula IA-Form III is characterized by an XRPD pattern comprising two peaks selected from the angles listed in Table 4 above. In other aspects, Formula IA-Form III is characterized by an XRPD pattern comprising three peaks selected from the angles listed in Table 4 above. In other aspects, Formula IA-Form III is characterized by an XRPD pattern comprising four peaks selected from the angles listed in Table 4 above. In other aspects, Formula IA-Form III is characterized by an XRPD pattern comprising five peaks selected from the angles listed in Table 4 above. In other aspects, Formula IA-Form III is characterized by an XRPD pattern comprising six peaks selected from the angles listed in Table 4 above. In other aspects, Formula IA-Form III is characterized by an XRPD pattern comprising seven peaks selected from the angles listed in Table 4 above. In other aspects, Formula IA-Form III is characterized by an XRPD pattern comprising eight peaks selected from the angles listed in Table 4 above. In other aspects, Formula IA-Form III is characterized by an XRPD pattern comprising nine peaks selected from the angles listed in Table 4 above. In other aspects, Formula IA-Form III is characterized by an XRPD pattern comprising ten peaks selected from the angles listed in Table 4 above. In other aspects, Formula IA-Form III is characterized by an XRPD pattern comprising more than ten peaks selected from the angles listed in Table 4 above.

In some embodiments, Formula IA-Form III is characterized by an XRPD pattern comprising a peak at 8.1 degrees±0.2 degrees 2-theta. In other embodiments, Formula IA-Form III is characterized by an XRPD pattern comprising peaks at 8.1 and 23.3 degrees±0.2 degrees 2-theta. In other embodiments, Formula IA-Form III is characterized by an XRPD pattern comprising peaks at 8.1, 12.5, 16.2, and 23.3 degrees±0.2 degree 2-theta. In other embodiments, Formula IA-Form III is characterized by an XRPD pattern comprising peaks at 8.1, 12.5, 16.2, 18.8, 23.3, and 24.5 degrees±0.2 degree 2-theta. In other embodiments, Formula IA-Form III is characterized by an XRPD pattern comprising peaks at 8.1, 12.5, 13.7, 14.5, 16.2, 18.8, 23.3, and 24.5 degrees±0.2 degree 2-theta. In yet other embodiments, Formula IA-Form III is characterized by an XRPD pattern comprising peaks at 8.1, 12.5, 13.7, 14.5, 15.3, 16.2, 18.8, 21.2, 23.3, and 24.5 degrees±0.2 degree 2-theta.

In some embodiments of the present disclosure, Formula IA-Form III is characterized by an XRPD pattern comprising peaks at three or more of 8.1, 12.5, 13.7, 14.5, 15.3, 16.2, 18.8, 21.2, 23.3, and 24.5 degrees±0.2 degrees 2-theta. In some embodiments of the present disclosure, Formula IA-Form III is characterized by an XRPD pattern comprising peaks at four or more of 8.1, 12.5, 13.7, 14.5, 15.3, 16.2, 18.8, 21.2, 23.3, and 24.5 degrees±0.2 degrees 2-theta. In some embodiments of the present disclosure, Formula IA-Form III is characterized by an XRPD pattern comprising peaks at five or more of 8.1, 12.5, 13.7, 14.5, 15.3, 16.2, 18.8, 21.2, 23.3, and 24.5 degrees±0.2 degrees 2-theta. In some embodiments of the present disclosure, Formula IA-Form III is characterized by an XRPD pattern comprising peaks at six or more of 8.1, 12.5, 13.7, 14.5, 15.3, 16.2, 18.8, 21.2, 23.3, and 24.5 degrees±0.2 degrees 2-theta. In some embodiments of the present disclosure, Formula IA-Form III is characterized by an XRPD pattern comprising peaks at seven or more of 8.1, 12.5, 13.7, 14.5, 15.3, 16.2, 18.8, 21.2, 23.3, and 24.5 degrees±0.2 degrees 2-theta.

Figure 9:
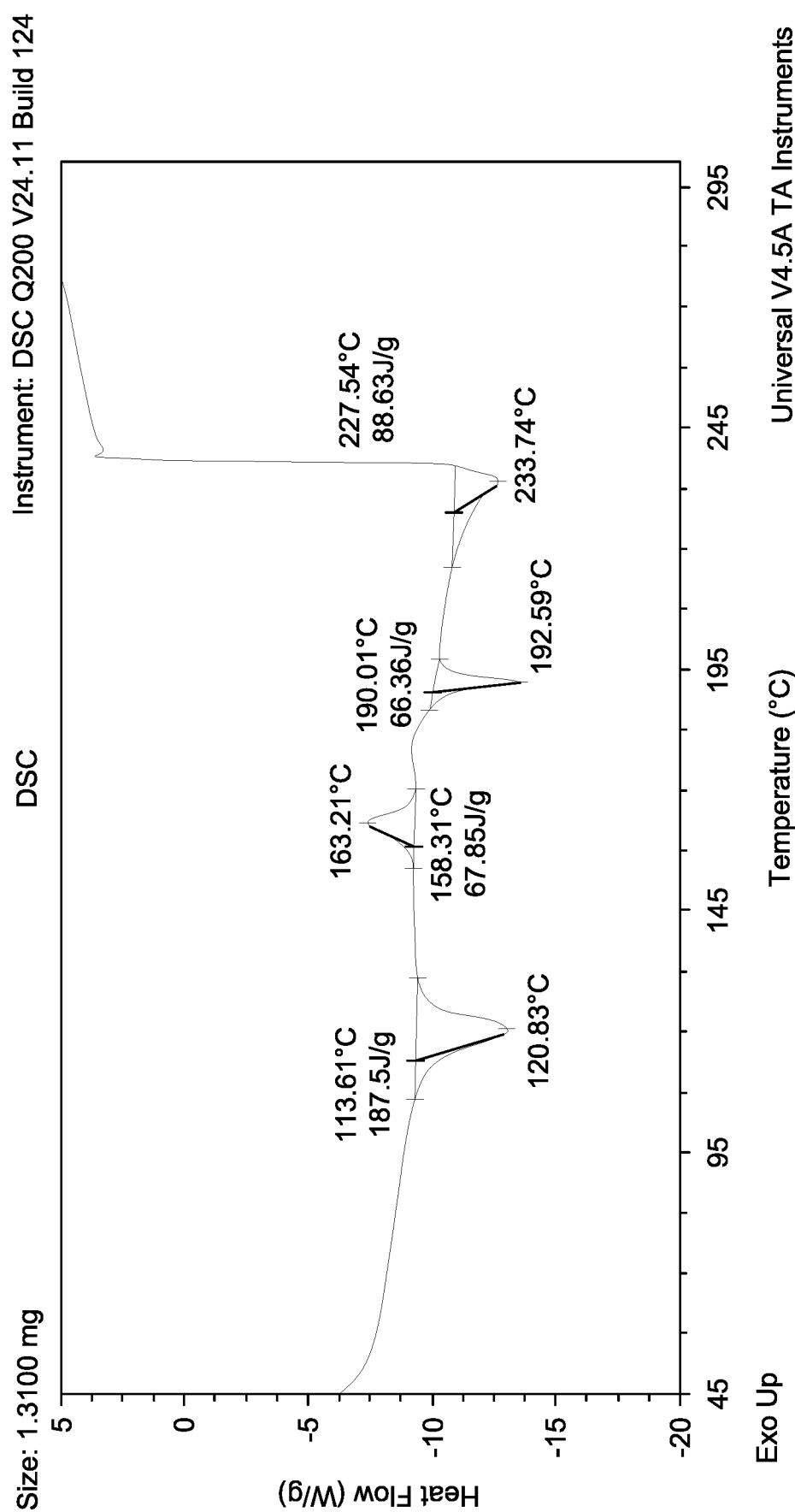
FIG. 9 shows a DSC thermogram of Formula IA-Form III.

In some embodiments, Formula IA-Form III can be characterized by a DSC thermogram substantially as shown in FIG. 9. As FIG. 9 shows, Formula IA-Form III produced an endothermic peak at 120.83° C., with a peak onset temperature of 113.61° C., and an enthalpy of melting of 187.5 J/g; followed by an exothermic peak at 163.21° C., with a peak onset temperature of 158.31° C., and an enthalpy of melting of 67.85 J/g; followed by an endothermic peak at 192.59° C., with a peak onset temperature of 190.01° C., and an enthalpy of melting of 66.36 J/g; followed by an endothermic peak at 233.74° C., with a peak onset temperature of 227.54° C., and an enthalpy of melting of 88.63 J/g when heated at a rate of 10° C./min. In some embodiments of the present disclosure, Formula IA-Form III is characterized by a DSC thermogram comprising an endothermic peak at about 121° C. In other embodiments of the present disclosure, Formula IA-Form III is characterized by a DSC enthalpy of melting of about 187.5 J/g.

Figure 10:
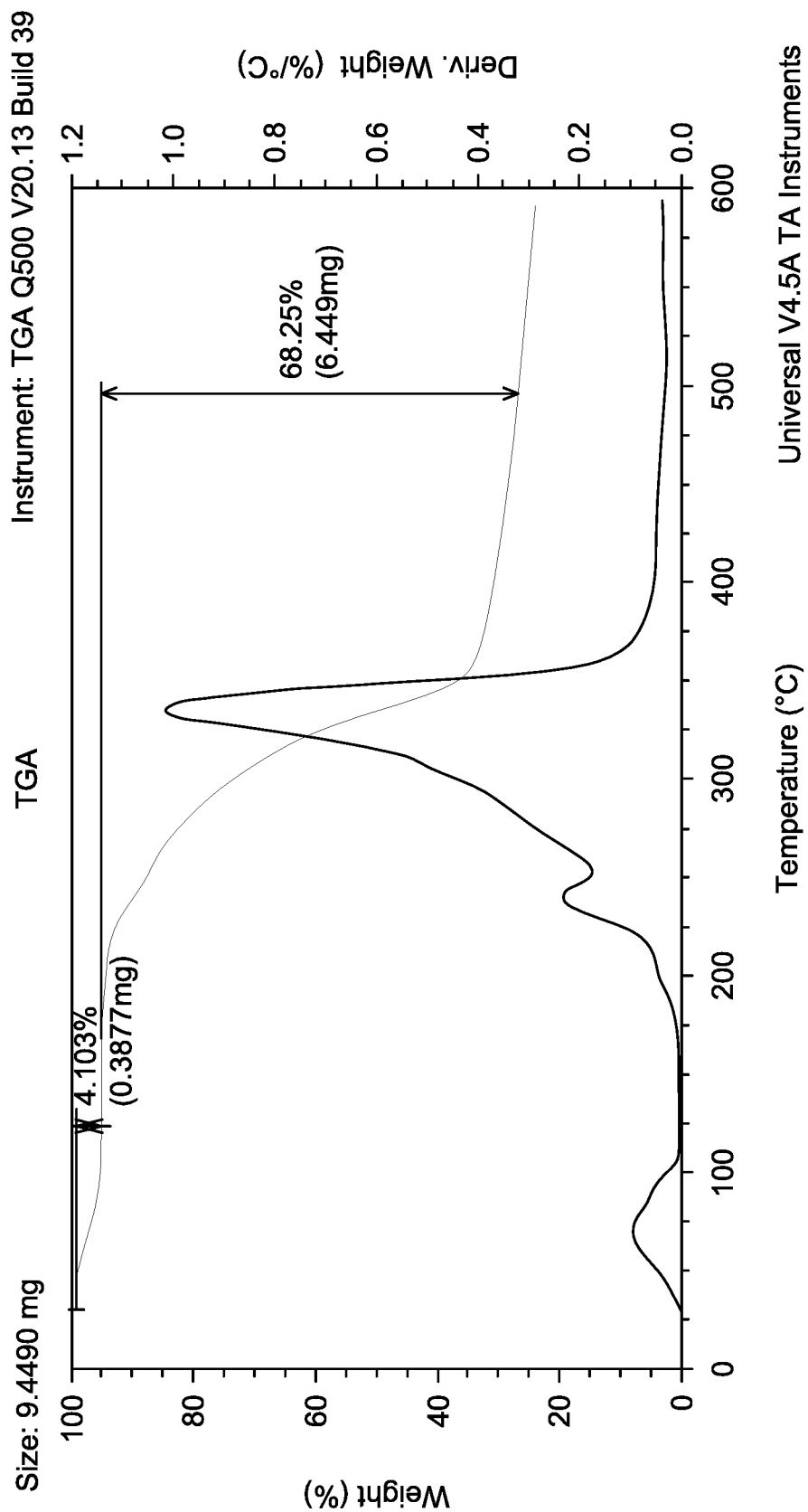
FIG. 10 shows a TGA profile of Formula IA-Form III.

In some embodiments, Formula IA-Form III can be characterized by a TGA profile substantially as shown in FIG. 10 when heated at a rate of 20° C./min. As FIG. 10 shows, Formula IA-Form III lost about 4.1% of its weight upon heating to about 125° C.

In some embodiments of the present disclosure, Formula IA-Form III is characterized by an XRPD pattern comprising peaks at one or more of 12.5, 13.7, 14.5, 15.3, 16.2, 18.8, 21.2, 23.3, and 24.5 degrees±0.2 degrees 2-theta, and a DSC thermogram comprising an endothermic peak at about 121° C. when heated at a rate of 10° C./min.

In some embodiments, the crystalline form of Formula IA is Form IV (Formula IA-Form IV). In some embodiments, Formula IA-Form IV is substantially free of any other solid form of Formula IA.

Figure 11:
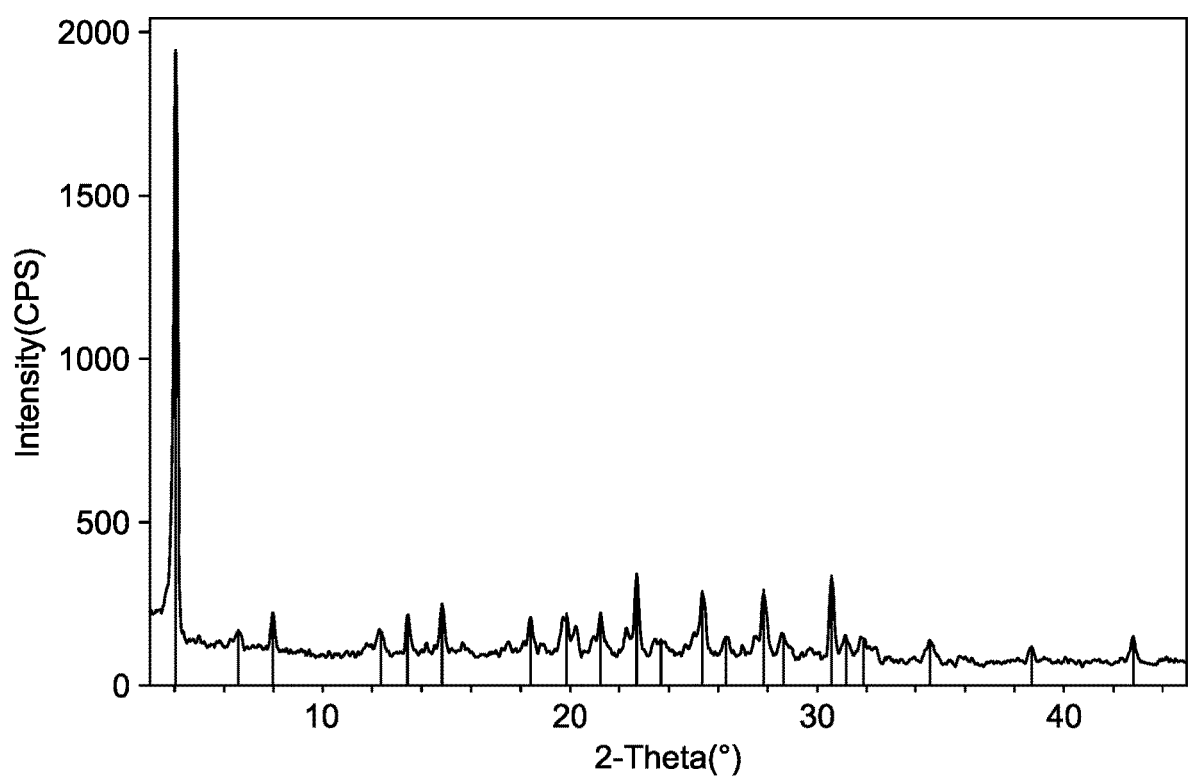
FIG. 11 shows an XRPD of Formula IA-Form IV.

In some embodiments, Formula IA-Form IV exhibits an XRPD substantially as shown in FIG. 11. The XRPD of Formula IA-Form IV shown in FIG. 11 comprises reflection angles (degrees 2-theta±0.2 degrees 2-theta), line spacings (d values), and relative intensities as shown in Table 5:

TABLE 5

XRPD Data for crystalline form of Formula IA-Form IV shown in FIG. 11

| Angle (degrees 2-theta ± 0.2 degrees 2-theta) | d Value (Å) | Relative Intensity |
|---|---|---|
| 4.04 | 21.8507 | 100 |
| 6.58 | 13.4221 | 3 |
| 7.961 | 11.0963 | 6.8 |

TABLE 5-continued

XRPD Data for crystalline form of Formula IA-Form IV shown in FIG. 11

| Angle (degrees 2-theta ± 0.2 degrees 2-theta) | d Value (Å) | Relative Intensity |
|---|---|---|
| 12.359 | 7.156 | 4.3 |
| 13.441 | 6.5823 | 7 |
| 14.84 | 5.9648 | 8.9 |
| 18.418 | 4.8131 | 6.5 |
| 19.86 | 4.4668 | 7 |
| 21.26 | 4.1757 | 7.3 |
| 22.719 | 3.9107 | 14.1 |
| 23.698 | 3.7513 | 2.7 |
| 25.361 | 3.509 | 11 |
| 26.32 | 3.3833 | 3.3 |
| 27.841 | 3.2019 | 11.6 |
| 28.657 | 3.1125 | 3.4 |
| 30.581 | 2.9209 | 13.8 |
| 31.177 | 2.8664 | 4.1 |
| 31.86 | 2.8065 | 3.9 |
| 34.599 | 2.5903 | 4.2 |
| 38.699 | 2.3248 | 2.8 |
| 42.799 | 2.1111 | 4.8 |

In some embodiments of the present disclosure, Formula IA-Form IV is characterized by an XRPD pattern comprising a peak at one of the angles listed in Table 5. In other aspects, Formula IA-Form IV is characterized by an XRPD pattern comprising more than one peak at one of the angles listed in Table 5 above. In other aspects, Formula IA-Form IV is characterized by an XRPD pattern comprising two peaks selected from the angles listed in Table 5 above. In other aspects, Formula IA-Form IV is characterized by an XRPD pattern comprising three peaks selected from the angles listed in Table 5 above. In other aspects, Formula IA-Form IV is characterized by an XRPD pattern comprising four peaks selected from the angles listed in Table 5 above. In other aspects, Formula IA-Form IV is characterized by an XRPD pattern comprising five peaks selected from the angles listed in Table 5 above. In other aspects, Formula IA-Form IV is characterized by an XRPD pattern comprising six peaks selected from the angles listed in Table 5 above. In other aspects, Formula IA-Form IV is characterized by an XRPD pattern comprising seven peaks selected from the angles listed in Table 5 above. In other aspects, Formula IA-Form IV is characterized by an XRPD pattern comprising eight peaks selected from the angles listed in Table 5 above. In other aspects, Formula IA-Form IV is characterized by an XRPD pattern comprising nine peaks selected from the angles listed in Table 5 above. In other aspects, Formula IA-Form IV is characterized by an XRPD pattern comprising ten peaks selected from the angles listed in Table 5 above. In other aspects, Formula IA-Form IV is characterized by an XRPD pattern comprising more than ten peaks selected from the angles listed in Table 5 above.

In some embodiments, Formula IA-Form IV is characterized by an XRPD pattern comprising a peak at 4.0 degrees±0.2 degrees 2-theta. In other embodiments, Formula IA-Form IV is characterized by an XRPD pattern comprising peaks at 4.0 and 22.7 degrees±0.2 degrees 2-theta. In other embodiments, Formula IA-Form IV is characterized by an XRPD pattern comprising peaks at 4.0, 22.7, 27.8 degrees±0.2 degree 2-theta. In other embodiments, Formula IA-Form IV is characterized by an XRPD pattern comprising peaks at 22.7, 27.8, 30.6 degrees±0.2 degree 2-theta. In other embodiments, Formula IA-Form IV is characterized by an XRPD pattern comprising peaks at 14.8, 22.7, 27.8, and 30.6 degrees±0.2 degree 2-theta. In yet other embodiments, Formula IA-Form IV is characterized by an XRPD pattern comprising peaks at 4.0, 14.8, 22.7, 27.8, and 30.6 degrees±0.2 degree 2-theta.

In some embodiments of the present disclosure, Formula IA-Form IV is characterized by an XRPD pattern comprising peaks at three or more of 4.0, 14.8, 22.7, 27.8, and 30.6 degrees±0.2 degrees 2-theta. In some embodiments of the present disclosure, Formula IA-Form IV is characterized by an XRPD pattern comprising peaks at four or more of 4.0, 14.8, 22.7, 27.8, and 30.6 degrees±0.2 degrees 2-theta.

Figure 12:
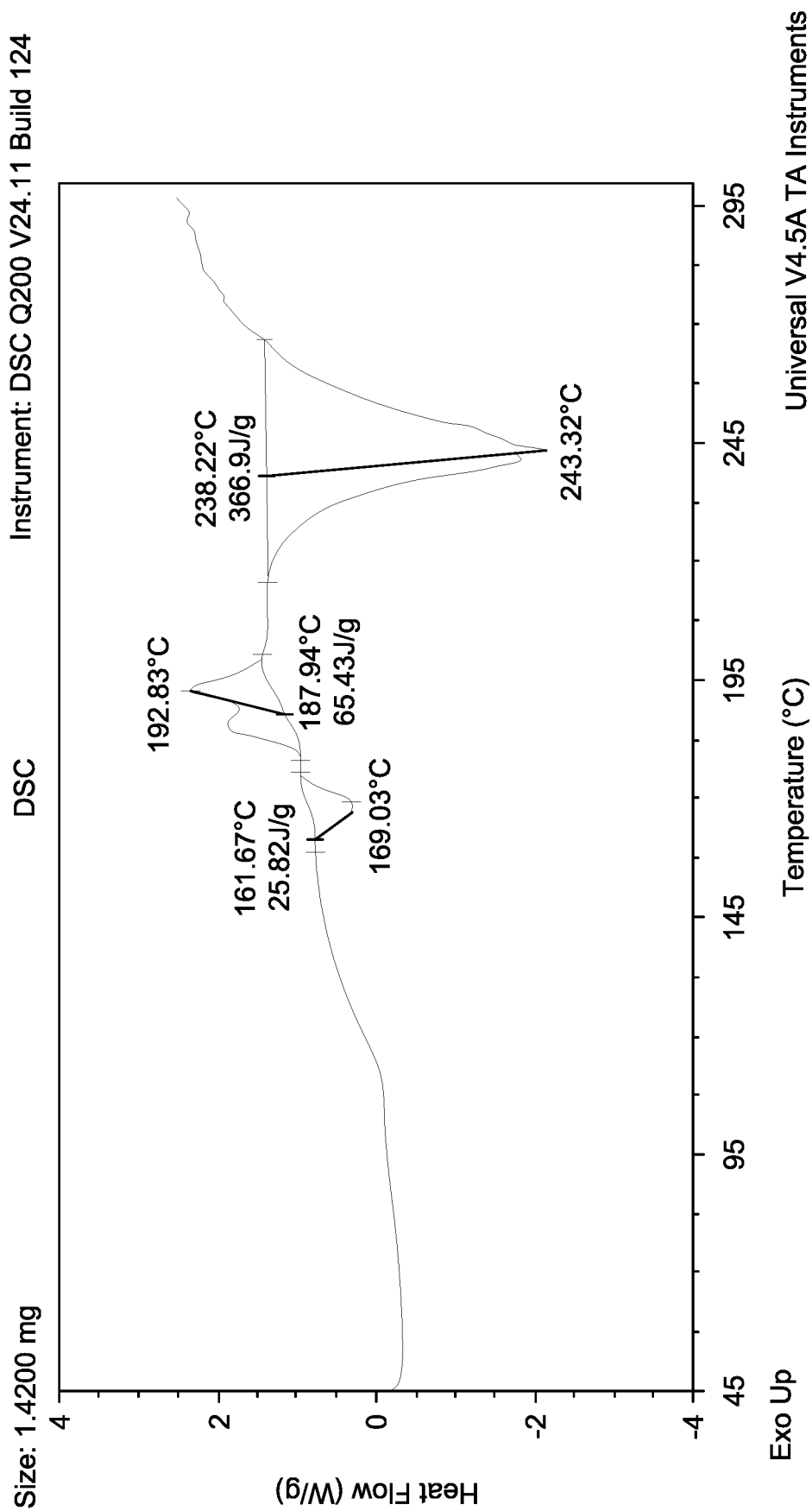
FIG. 12 shows a DSC thermogram of Formula IA-Form IV.

In some embodiments, Formula IA-Form IV can be characterized by a DSC thermogram substantially as shown in FIG. 12. As FIG. 12 shows, Formula IA-Form IV produced an endothermic peak at 169.03° C., with a peak onset temperature of 161.67° C., and an enthalpy of melting of 25.82 J/g, followed by an exothermic peak at 192.83° C., followed by an endothermic peak at 243.32° C. with an onset temperature of 238.22° C., and an enthalpy of 366.9 J/g, when heated at a rate of 10° C./min. In some embodiments of the present disclosure, Formula IA-Form IV is characterized by a DSC thermogram comprising an endothermic peak at about 169° C. In other embodiments of the present disclosure, Formula IA-Form IV is characterized by a DSC enthalpy of melting of about 26 J/g.

Figure 13:
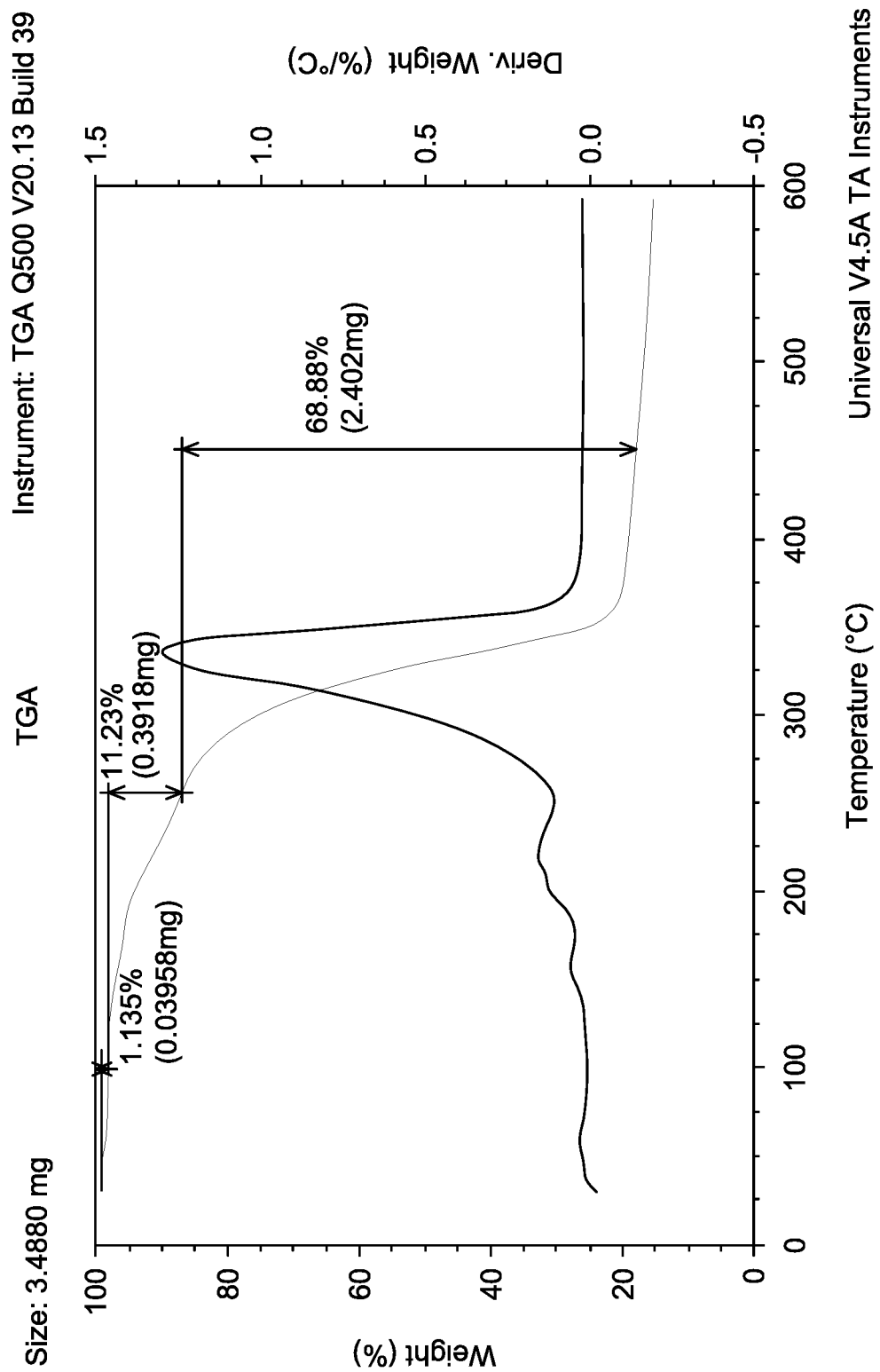
FIG. 13 shows a TGA profile of Formula IA-Form IV.

In some embodiments, Formula IA-Form IV can be characterized by a TGA profile substantially as shown in FIG. 13 when heated at a rate of 20° C./min. As FIG. 13 shows, Formula IA-Form IV lost about 12.4 (1.135%+ 11.23%) % of its weight upon heating to about 300° C.

In some embodiments of the present disclosure, Formula IA-Form IV is characterized by an XRPD pattern comprising peaks at one or more of 4.0, 14.8, 22.7, 27.8, and 30.6 degrees±0.2 degrees 2-theta, and a DSC thermogram comprising an endothermic peak at about 169° C. when heated at a rate of 10° C./min.

In some aspects, the disclosure is directed to a crystalline form of the phosphate salt of Formula I, i.e., Formula D3.

Figure 14A:
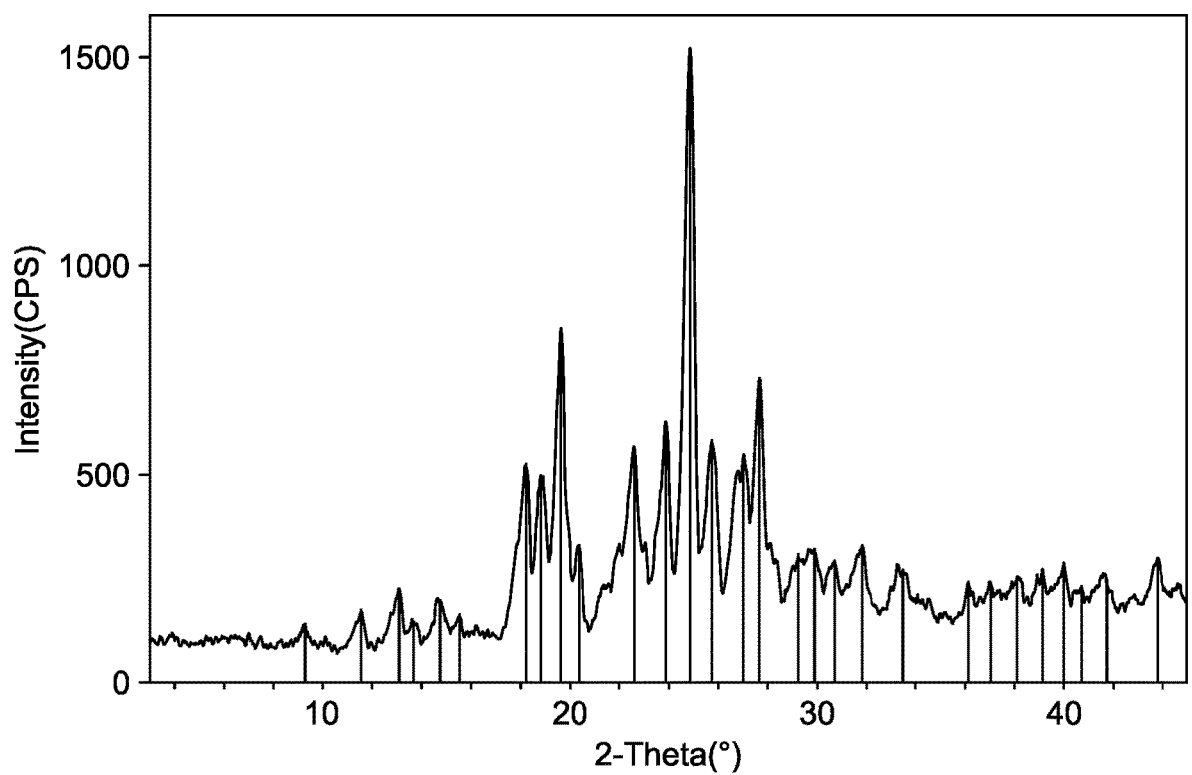
FIG. 14A shows an XRPD of Formula IB-Form I.

In some embodiments, the crystalline salt of Formula IB is Formula IB-Form I, exhibits an XRPD substantially as shown in FIG. 14A. The XRPD of Formula IB-Form I shown in FIG. 14A comprises reflection angles (degrees 2-theta±0.2 degrees 2-theta), line spacings (d values), and relative intensities as shown in Table 6:

TABLE 6

XRPD Data for crystalline form of Formula IB-Form I shown in FIG. 14A

| Angle (degrees 2-theta ± 0.2 degrees 2-theta) | d Value (Å) | Relative Intensity |
|---|---|---|
| 9.298 | 9.5039 | 4.7 |
| 11.56 | 7.6487 | 7.5 |
| 13.08 | 6.763 | 10.9 |
| 13.679 | 6.468 | 3.9 |
| 14.74 | 6.005 | 7.5 |
| 15.539 | 5.6978 | 4.7 |
| 18.22 | 4.8651 | 32.7 |
| 18.819 | 4.7114 | 23.8 |
| 19.62 | 4.5209 | 55.9 |
| 20.36 | 4.3581 | 10.1 |
| 22.6 | 3.9311 | 27.1 |
| 23.88 | 3.7232 | 28.8 |
| 24.86 | 3.5786 | 100 |
| 25.74 | 3.4582 | 27.6 |
| 27.001 | 3.2995 | 25.6 |
| 27.66 | 3.2223 | 41 |
| 29.239 | 3.0518 | 7.9 |
| 29.88 | 2.9878 | 8.9 |
| 30.699 | 2.9099 | 6.1 |

TABLE 6-continued

XRPD Data for crystalline form of Formula IB-Form I shown in FIG. 14A

| Angle (degrees 2-theta ± 0.2 degrees 2-theta) | d Value (Å) | Relative Intensity |
|---|---|---|
| 31.82 | 2.8099 | 11 |
| 33.48 | 2.6743 | 8.8 |
| 36.138 | 2.4835 | 5.4 |
| 37.019 | 2.4264 | 5.2 |
| 38.101 | 2.3599 | 5 |
| 39.138 | 2.2997 | 6.7 |
| 39.999 | 2.2522 | 7.8 |
| 40.7 | 2.215 | 3.7 |
| 41.717 | 2.1634 | 5.4 |
| 43.8 | 2.0652 | 9 |

In some embodiments of the present disclosure, Formula IB-Form I is characterized by an XRPD pattern comprising a peak at one of the angles listed in Table 6. In other aspects, Formula IB-Form I is characterized by an XRPD pattern comprising more than one peak at one of the angles listed in Table 6 above. In other aspects, Formula IB-Form I is characterized by an XRPD pattern comprising two peaks selected from the angles listed in Table 6 above. In other aspects, Formula IB-Form I is characterized by an XRPD pattern comprising three peaks selected from the angles listed in Table 6 above. In other aspects, Formula IB-Form I is characterized by an XRPD pattern comprising four peaks selected from the angles listed in Table 6 above. In other aspects, Formula IB-Form I is characterized by an XRPD pattern comprising five peaks selected from the angles listed in Table 6 above. In other aspects, Formula IB-Form I is characterized by an XRPD pattern comprising six peaks selected from the angles listed in Table 6 above. In other aspects, Formula IB-Form I is characterized by an XRPD pattern comprising seven peaks selected from the angles listed in Table 6 above. In other aspects, Formula IB-Form I is characterized by an XRPD pattern comprising eight peaks selected from the angles listed in Table 6 above. In other aspects, Formula IB-Form I is characterized by an XRPD pattern comprising nine peaks selected from the angles listed in Table 6 above. In other aspects, Formula IB-Form I is characterized by an XRPD pattern comprising ten peaks selected from the angles listed in Table 6 above. In other aspects, Formula IB-Form I is characterized by an XRPD pattern comprising more than ten peaks selected from the angles listed in Table 6 above.

In some embodiments, Formula IB-Form I is characterized by an XRPD pattern comprising a peak at 24.9 degrees±0.2 degrees 2-theta. In other embodiments, Formula IB-Form I is characterized by an XRPD pattern comprising peaks at 18.2, 19.6, and 24.9 degrees±0.2 degrees 2-theta. In other embodiments, Formula IB-Form I is characterized by an XRPD pattern comprising peaks at 18.2, 19.6, 24.9 25.7, and 27.0 degrees±0.2 degree 2-theta. In other embodiments, Formula IB-Form I is characterized by an XRPD pattern comprising peaks at 18.2, 18.8, 19.6, 24.9 25.7, and 27.0 degrees±0.2 degree 2-theta.

In some embodiments of the present disclosure, Formula IB-Form I is characterized by an XRPD pattern comprising peaks at three or more of 18.2, 18.8, 19.6, 24.9 25.7, and 27.0 degrees±0.2 degrees 2-theta. In some embodiments of the present disclosure, Formula IB-Form I is characterized by an XRPD pattern comprising peaks at four or more of 18.2, 18.8, 19.6, 24.9 25.7, and 27.0 degrees±0.2 degrees 2-theta. In some embodiments of the present disclosure, Formula IB-Form I is characterized by an XRPD pattern comprising peaks at five or more of 18.2, 18.8, 19.6, 24.9 25.7, and 27.0 degrees±0.2 degrees 2-theta. In some embodiments of the present disclosure, Formula IB-Form I is characterized by an XRPD pattern comprising peaks at six or more of 18.2, 18.8, 19.6, 24.9 25.7, and 27.0 degrees±0.2 degrees 2-theta. In some embodiments of the present disclosure, Formula IB-Form I is characterized by an XRPD pattern comprising peaks at seven or more of 18.2, 18.8, 19.6, 24.9 25.7, and 27.0 degrees±0.2 degrees 2-theta.

Figure 15A:
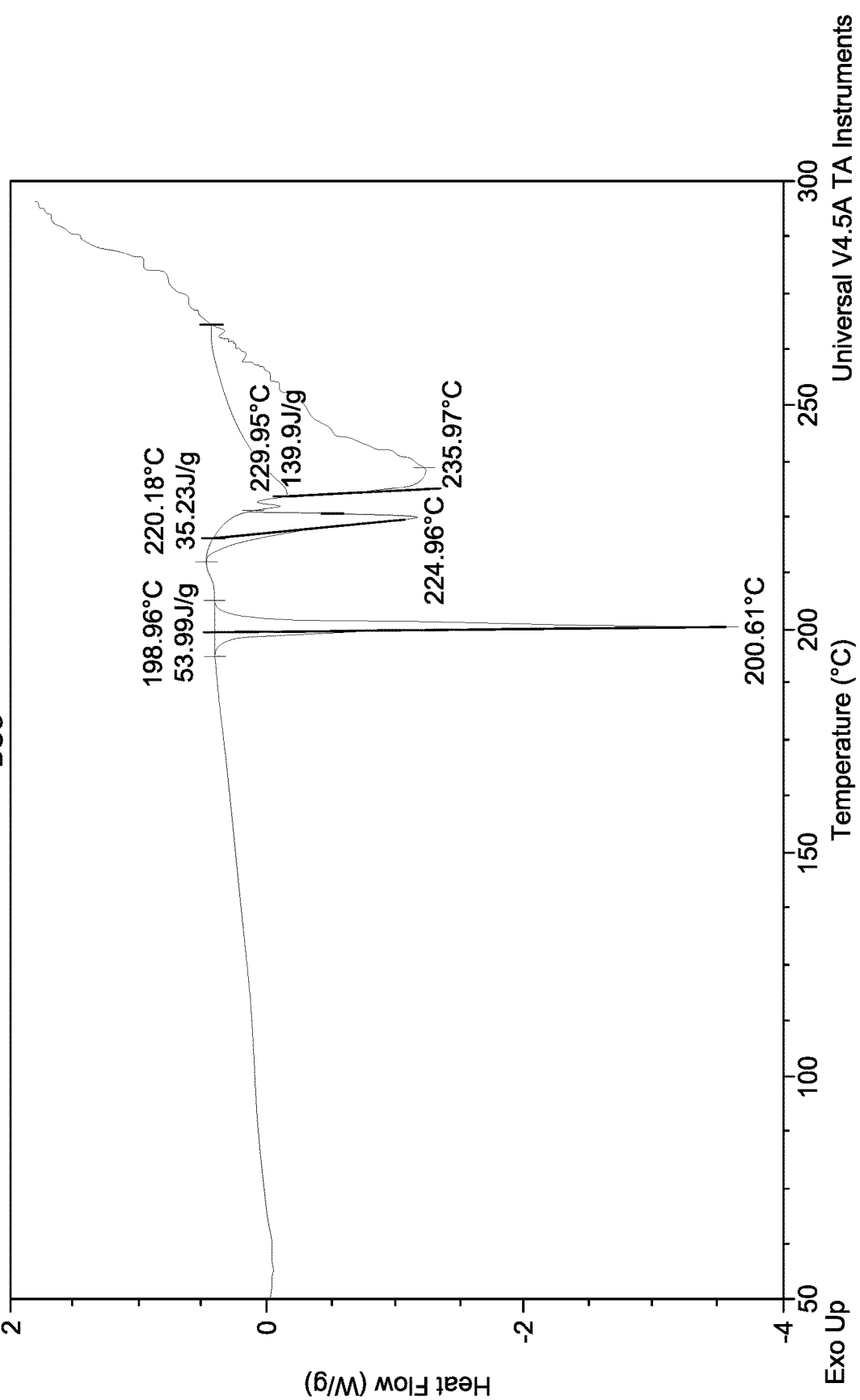
FIG. 15A shows a DSC thermogram of Formula IB-Form I.

In some embodiments, Formula IB-Form I can be characterized by a DSC thermogram substantially as shown in FIG. 15A. As FIG. 15A shows, Formula IB-Form I produced an endothermic peak at 200.6° C., with a peak onset temperature of 198.96° C., and an enthalpy of melting of 53.99 J/g, followed by an endothermic peaks at 224.96° C. and 235.97° C. when heated at a rate of 10° C./min. In some embodiments of the present disclosure, Formula IB-Form I is characterized by a DSC thermogram comprising an endothermic peak at about 201° C. In other embodiments of the present disclosure, Formula IB-Form I is characterized by a DSC enthalpy of melting of about 54 J/g.

Figure 16A:
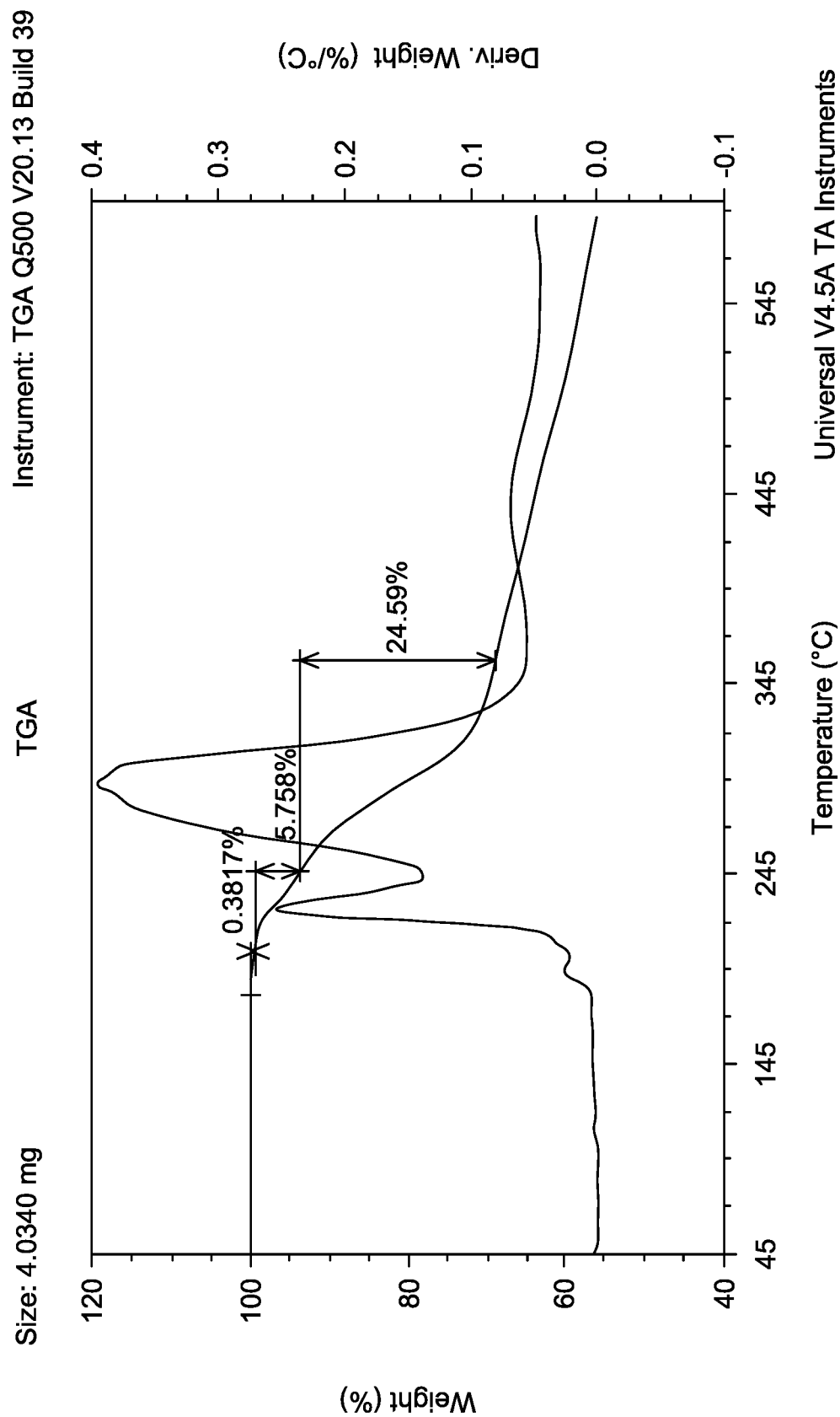
FIG. 16A shows a TGA profile of Formula IB-Form I.

In some embodiments, Formula IB-Form I can be characterized by a TGA profile substantially as shown in FIG. 16A when heated at a rate of 20° C./min. As FIG. 16A shows, Formula IB-Form I lost about 6% of its weight upon heating to about 250° C.

In some embodiments of the present disclosure, Formula IB-Form I is characterized by an XRPD pattern comprising peaks at one or more of 18.2, 18.8, 19.6, 24.9 25.7, and 27.0 degrees±0.2 degrees 2-theta, and a DSC thermogram comprising an endothermic peak at about 201° C. when heated at a rate of 10° C./min.

Figure 14B:
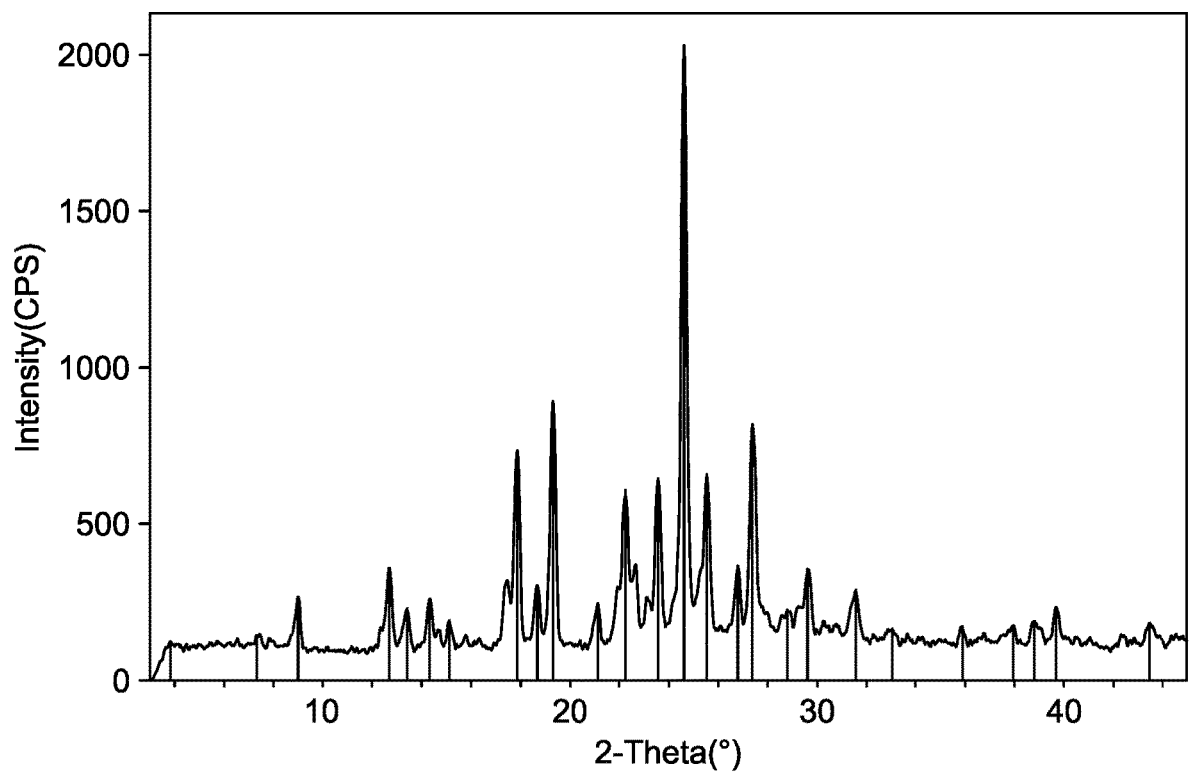
FIG. 14B shows an XRPD of Formula IB-Form II.

In some embodiments, the crystalline salt of Formula IB is Formula IB-Form II, which exhibits an XRPD substantially as shown in FIG. 14B. The XRPD of Formula IB-Form II shown in FIG. 14B comprises reflection angles (degrees 2-theta±0.2 degrees 2-theta), line spacings (d values), and relative intensities as shown in Table 6B:

TABLE 6B

XRPD Data for crystalline form of Formula IB-Form II shown in FIG. 14B

| Angle (degrees 2-theta ± 0.2 degrees 2-theta) | d Value (Å) | Relative Intensity |
|---|---|---|
| 3.84 | 22.9927 | 6.4 |
| 7.322 | 12.063 | 2.1 |
| 9.02 | 9.7961 | 9.4 |
| 12.72 | 6.9537 | 14.4 |
| 13.439 | 6.5832 | 7.2 |
| 14.34 | 6.1715 | 8.6 |
| 15.138 | 5.8477 | 4.7 |
| 17.88 | 4.9568 | 33 |
| 18.699 | 4.7414 | 9.8 |
| 19.32 | 4.5904 | 41.7 |
| 21.159 | 4.1953 | 7.2 |
| 22.28 | 3.9868 | 24.3 |
| 23.6 | 3.7667 | 25.5 |
| 24.64 | 3.6101 | 100 |
| 25.56 | 3.4821 | 26.5 |
| 26.82 | 3.3214 | 11.2 |
| 27.42 | 3.25 | 35.5 |
| 28.821 | 3.0951 | 3.7 |
| 29.641 | 3.0114 | 10.9 |
| 31.599 | 2.8291 | 8.4 |
| 33.1 | 2.7041 | 2.6 |
| 35.937 | 2.4969 | 3.3 |
| 37.979 | 2.3672 | 3.2 |
| 38.859 | 2.3156 | 3.9 |

TABLE 6B-continued

XRPD Data for crystalline form of Formula IB-Form II shown in FIG. 14B

| Angle (degrees 2-theta ± 0.2 degrees 2-theta) | d Value (Å) | Relative Intensity |
|---|---|---|
| 39.72 | 2.2674 | 6.5 |
| 43.5 | 2.0787 | 4.3 |

In some embodiments of the present disclosure, Formula IB-Form II is characterized by an XRPD pattern comprising a peak at one of the angles listed in Table 6B. In other aspects, Formula IB-Form II is characterized by an XRPD pattern comprising more than one peak at one of the angles listed in Table 6B above. In other aspects, Formula IB-Form II is characterized by an XRPD pattern comprising two peaks selected from the angles listed in Table 6B above. In other aspects, Formula IB-Form II is characterized by an XRPD pattern comprising three peaks selected from the angles listed in Table 6B above. In other aspects, Formula IB-Form II is characterized by an XRPD pattern comprising four peaks selected from the angles listed in Table 6B above. In other aspects, Formula IB-Form II is characterized by an XRPD pattern comprising five peaks selected from the angles listed in Table 6B above. In other aspects, Formula IB-Form II is characterized by an XRPD pattern comprising six peaks selected from the angles listed in Table 6B above. In other aspects, Formula IB-Form II is characterized by an XRPD pattern comprising seven peaks selected from the angles listed in Table 6B above. In other aspects, Formula IB-Form II is characterized by an XRPD pattern comprising eight peaks selected from the angles listed in Table 6B above. In other aspects, Formula IB-Form II is characterized by an XRPD pattern comprising nine peaks selected from the angles listed in Table 6B above. In other aspects, Formula IB-Form II is characterized by an XRPD pattern comprising ten peaks selected from the angles listed in Table 6B above. In other aspects, Formula IB-Form II is characterized by an XRPD pattern comprising more than ten peaks selected from the angles listed in Table 6B above.

In some embodiments, Formula IB-Form II is characterized by an XRPD pattern comprising a peak at 24.6 degrees±0.2 degrees 2-theta. In other embodiments, Formula IB-Form II is characterized by an XRPD pattern comprising peaks at 19.3, 24.6, and 27.4 degrees±0.2 degrees 2-theta. In other embodiments, Formula IB-Form II is characterized by an XRPD pattern comprising peaks at 19.3, 22.3, 23.6, 24.6, and 27.4 degrees±0.2 degree 2-theta. In other embodiments, Formula IB-Form II is characterized by an XRPD pattern comprising peaks at 19.3, 22.3, 23.6, 24.6, 25.6 and 27.4 degrees±0.2 degree 2-theta.

In some embodiments of the present disclosure, Formula IB-Form II is characterized by an XRPD pattern comprising peaks at three or more of 19.3, 22.3, 23.6, 24.6, 25.6 and 27.4 degrees±0.2 degrees 2-theta. In some embodiments of the present disclosure, Formula IB-Form II is characterized by an XRPD pattern comprising peaks at four or more of 19.3, 22.3, 23.6, 24.6, 25.6 and 27.4 degrees±0.2 degrees 2-theta. In some embodiments of the present disclosure, Formula IB-Form II is characterized by an XRPD pattern comprising peaks at five or more of 19.3, 22.3, 23.6, 24.6, 25.6 and 27.4 degrees±0.2 degrees 2-theta. In some embodiments of the present disclosure, Formula IB-Form II is characterized by an XRPD pattern comprising peaks at six or more of 19.3, 22.3, 23.6, 24.6, 25.6 and 27.4 degrees±0.2 degrees 2-theta.

Figure 15B:
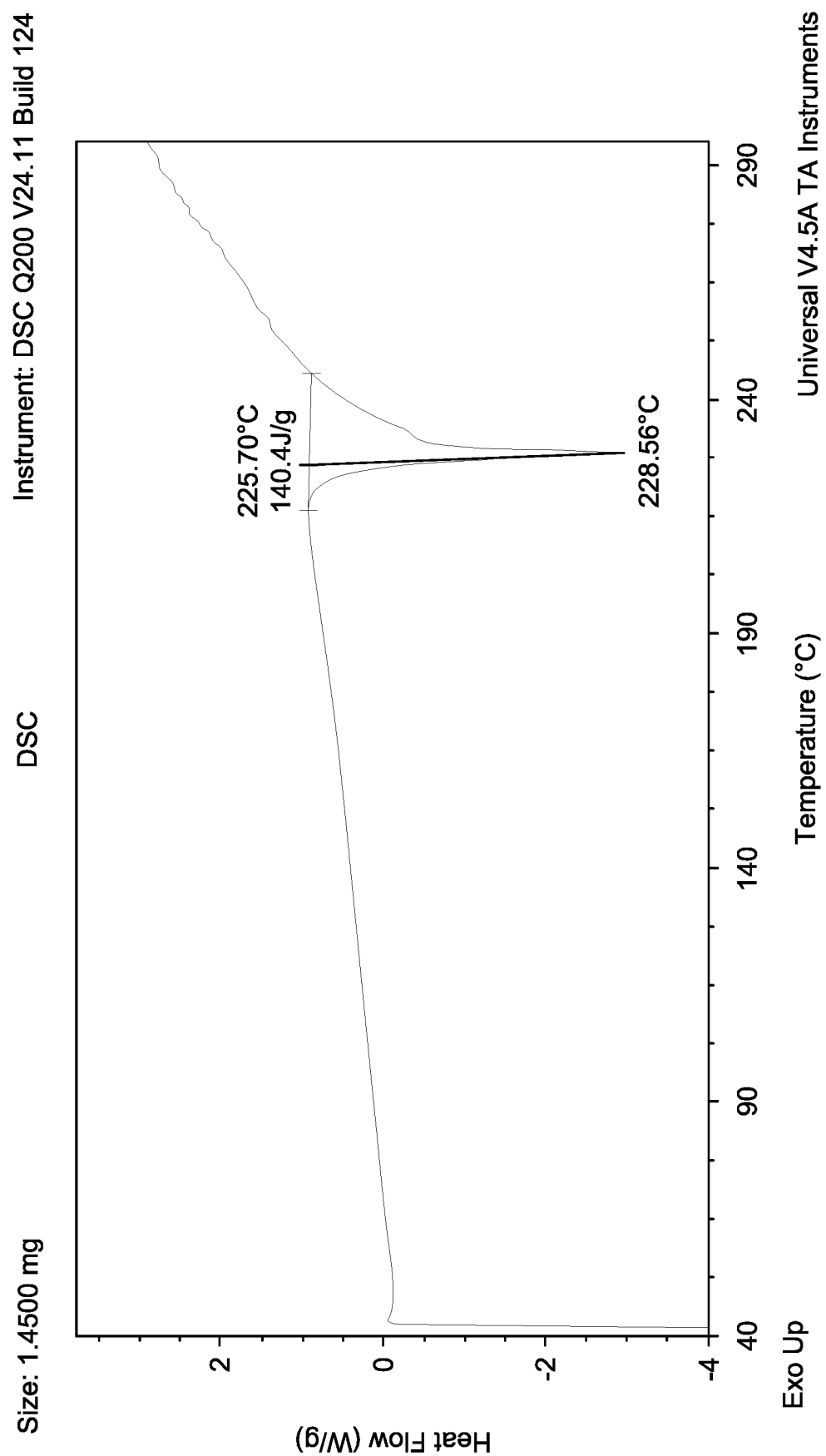
FIG. 15B shows a DSC thermogram of Formula IB-Form II.

In some embodiments, Formula IB-Form II can be characterized by a DSC thermogram substantially as shown in FIG. 15B. As FIG. 15B shows, Formula IB-Form II produced an endothermic peak at 228.56° C., with a peak onset temperature of 225.70° C., and an enthalpy of melting of 140.4 J/g, when heated at a rate of 10° C./min. In some embodiments of the present disclosure, Formula IB-Form II is characterized by a DSC thermogram comprising an endothermic peak at about 229° C. In other embodiments of the present disclosure, Formula IB-Form II is characterized by a DSC enthalpy of melting of about 140 J/g.

Figure 16B:
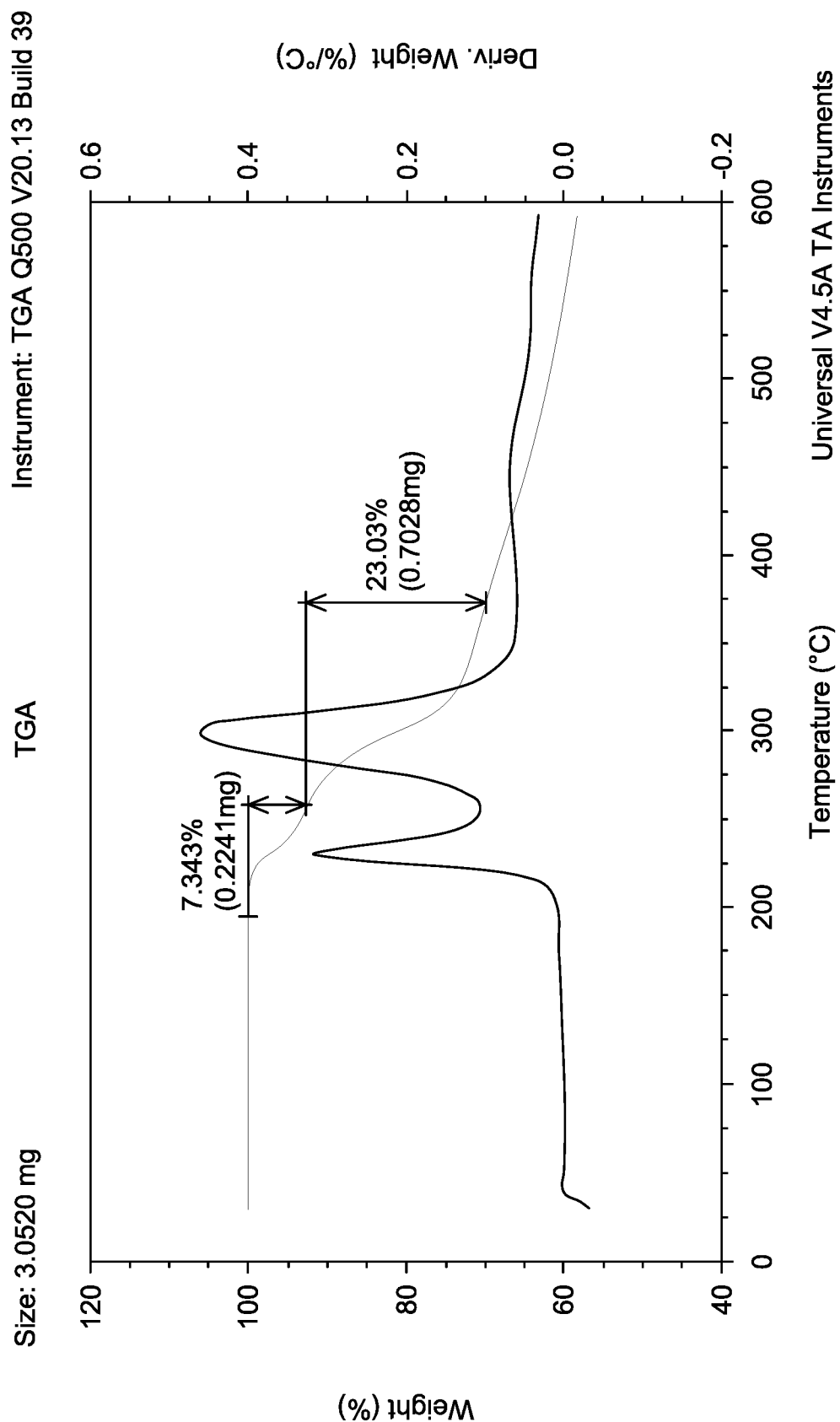
FIG. 16B shows a TGA profile of Formula IB-Form II.

In some embodiments, Formula IB-Form II can be characterized by a TGA profile substantially as shown in FIG. 16B when heated at a rate of 20° C./min. As FIG. 16B shows, Formula IB-Form II lost about 7.3% of its weight upon heating to about 275° C.

In some embodiments of the present disclosure, Formula IB-Form II is characterized by an XRPD pattern comprising peaks at one or more of 19.3, 22.3, 23.6, 24.6, 25.6 and 27.4 degrees±0.2 degrees 2-theta, and a DSC thermogram comprising an endothermic peak at about 229° C. when heated at a rate of 10° C./min.

In some aspects, the disclosure is directed to a crystalline form of the tartrate salt of Formula I, i.e., Formula IC.

Figure 17:
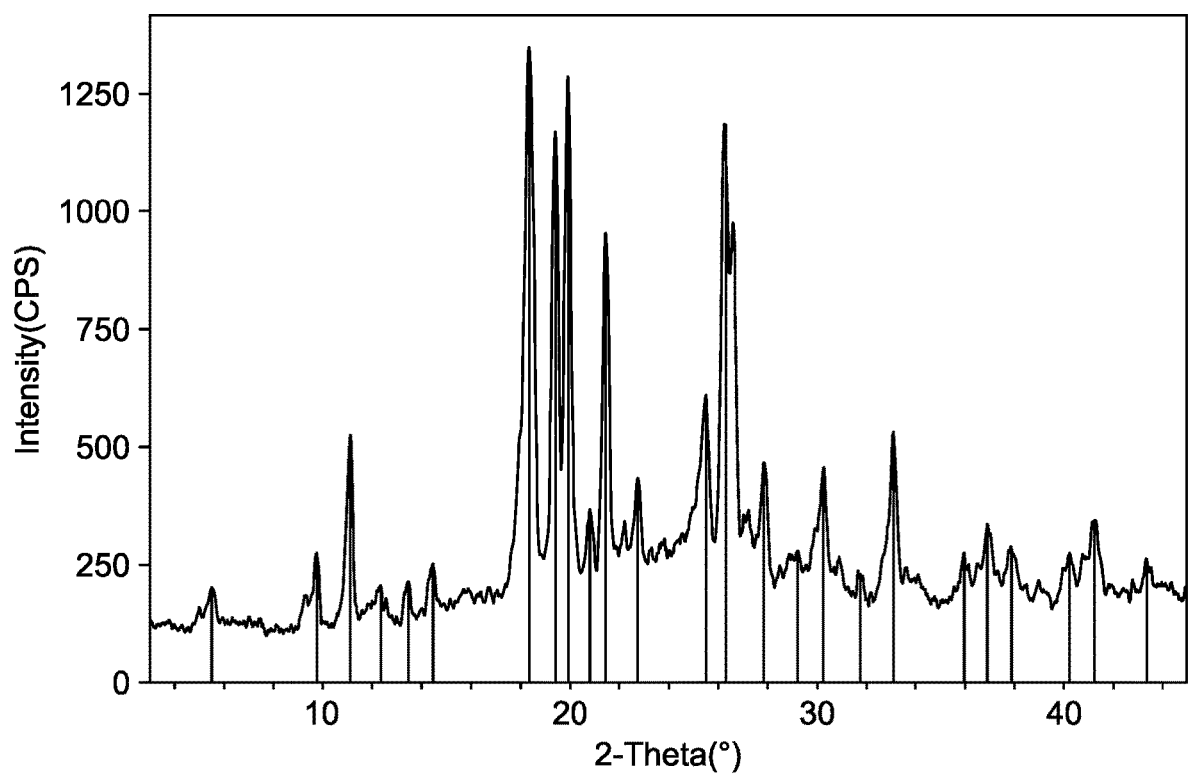
FIG. 17 shows an XRPD of Formula IC.

In some embodiments, Formula IC exhibits an XRPD substantially as shown in FIG. 17. The XRPD of Formula IC shown in FIG. 17 comprises reflection angles (degrees 2-theta±0.2 degrees 2-theta), line spacings (d values), and relative intensities as shown in Table 7:

TABLE 7

XRPD Data for crystalline form of Formula IC shown in FIG. 17

| Angle (degrees 2-theta ± 0.2 degrees 2-theta) | d Value (Å) | Relative Intensity |
|---|---|---|
| 5.5 | 16.0539 | 7.9 |
| 9.779 | 9.0371 | 14.3 |
| 11.14 | 7.9361 | 35.7 |
| 12.376 | 7.1462 | 6.6 |
| 13.48 | 6.563 | 7.7 |
| 14.479 | 6.1126 | 9.5 |
| 18.38 | 4.8231 | 100 |
| 19.44 | 4.5623 | 82.4 |
| 19.94 | 4.4491 | 93.9 |
| 20.84 | 4.2589 | 11.5 |
| 21.481 | 4.1333 | 62.4 |
| 22.78 | 3.9004 | 15.6 |
| 25.54 | 3.4849 | 28.4 |
| 26.339 | 3.3809 | 78.5 |
| 27.881 | 3.1973 | 19.8 |
| 29.24 | 3.0517 | 5.8 |
| 30.28 | 2.9492 | 21.7 |
| 31.779 | 2.8134 | 4.8 |
| 33.14 | 2.701 | 32.7 |
| 35.98 | 2.494 | 8.7 |
| 36.941 | 2.4313 | 13.2 |
| 37.919 | 2.3708 | 7.6 |
| 40.28 | 2.2371 | 9.3 |
| 41.28 | 2.1852 | 15.1 |
| 43.398 | 2.0834 | 7.8 |

In some embodiments of the present disclosure, Formula IC is characterized by an XRPD pattern comprising a peak at one of the angles listed in Table 7. In other aspects, Formula IC is characterized by an XRPD pattern comprising more than one peak at one of the angles listed in Table 7 above. In other aspects, Formula IC is characterized by an XRPD pattern comprising two peaks selected from the angles listed in Table 7 above. In other aspects, Formula IC is characterized by an XRPD pattern comprising three peaks selected from the angles listed in Table 7 above. In other aspects, Formula IC is characterized by an XRPD pattern comprising four peaks selected from the angles listed in Table 7 above. In other aspects, Formula IC is characterized by an XRPD pattern comprising five peaks selected from the angles listed in Table 7 above. In other aspects, Formula IC is characterized by an XRPD pattern comprising six peaks selected from the angles listed in Table 7 above. In other aspects, Formula IC is characterized by an XRPD pattern comprising seven peaks selected from the angles listed in Table 7 above. In other aspects, Formula IC is characterized by an XRPD pattern comprising eight peaks selected from the angles listed in Table 7 above. In other aspects, Formula IC is characterized by an XRPD pattern comprising nine peaks selected from the angles listed in Table 7 above. In other aspects, Formula IC is characterized by an XRPD pattern comprising ten peaks selected from the angles listed in Table 7 above. In other aspects, Formula IC is characterized by an XRPD pattern comprising more than ten peaks selected from the angles listed in Table 7 above.

In some embodiments, Formula IC is characterized by an XRPD pattern comprising a peak at 18.4 degrees±0.2 degrees 2-theta. In other embodiments, Formula IC is characterized by an XRPD pattern comprising peaks at 18.4, 19.9, and 21.5 degrees±0.2 degrees 2-theta. In other embodiments, Formula IC is characterized by an XRPD pattern comprising peaks at 18.4, 19.4, 19.9, 21.5, and 26.3 degrees±0.2 degree 2-theta. In other embodiments, Formula IC is characterized by an XRPD pattern comprising peaks at 11.4 18.4, 19.4, 19.9, 21.5, 26.3 and 30.2 degrees±0.2 degree 2-theta. In other embodiments, Formula IC is characterized by an XRPD pattern comprising peaks at 11.4 18.4, 19.4, 19.9, 21.5, 26.3, 30.2, and 33.1 degrees±0.2 degree 2-theta.

In some embodiments of the present disclosure, Formula IC is characterized by an XRPD pattern comprising peaks at three or more of 11.4 18.4, 19.4, 19.9, 21.5, 26.3 30.2, and 33.1 degrees±0.2 degrees 2-theta. In some embodiments of the present disclosure, Formula IC is characterized by an XRPD pattern comprising peaks at four or more of 11.4 18.4, 19.4, 19.9, 21.5, 26.3 30.2, and 33.1 degrees±0.2 degrees 2-theta. In some embodiments of the present disclosure, Formula IC is characterized by an XRPD pattern comprising peaks at five or more of 11.4 18.4, 19.4, 19.9, 21.5, 26.3 30.2, and 33.1 degrees±0.2 degrees 2-theta. In some embodiments of the present disclosure, Formula IC is characterized by an XRPD pattern comprising peaks at six or more of 11.4 18.4, 19.4, 19.9, 21.5, 26.3 30.2, and 33.1 degrees±0.2 degrees 2-theta. In some embodiments of the present disclosure, Formula IC is characterized by an XRPD pattern comprising peaks at seven or more of 11.4 18.4, 19.4, 19.9, 21.5, 26.3, 30.2, and 33.1 degrees±0.2 degrees 2-theta.

Figure 18:
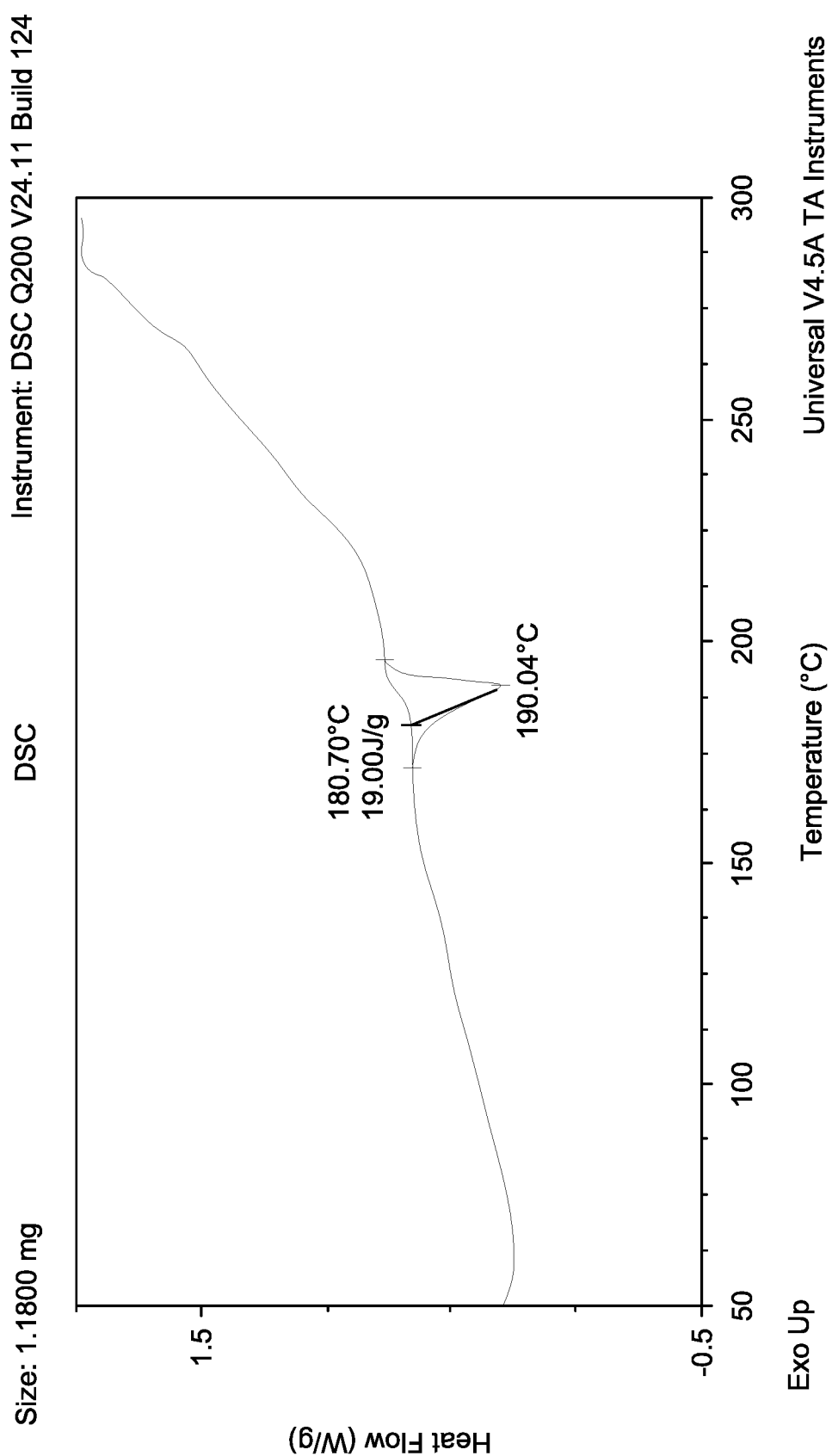
FIG. 18 shows a DSC thermogram of Formula IC.

In some embodiments, Formula IC can be characterized by a DSC thermogram substantially as shown in FIG. 18. As FIG. 18 shows, Formula IC produced an endothermic peak at 190.04° C., with a peak onset temperature of 180.70° C., and an enthalpy of melting of 19.00 J/g, when heated at a rate of 10° C./min. In some embodiments of the present disclosure, Formula IC is characterized by a DSC thermogram comprising an endothermic peak at about 190° C. In other embodiments of the present disclosure, Formula IC is characterized by a DSC enthalpy of melting of about 19 J/g.

Figure 19:
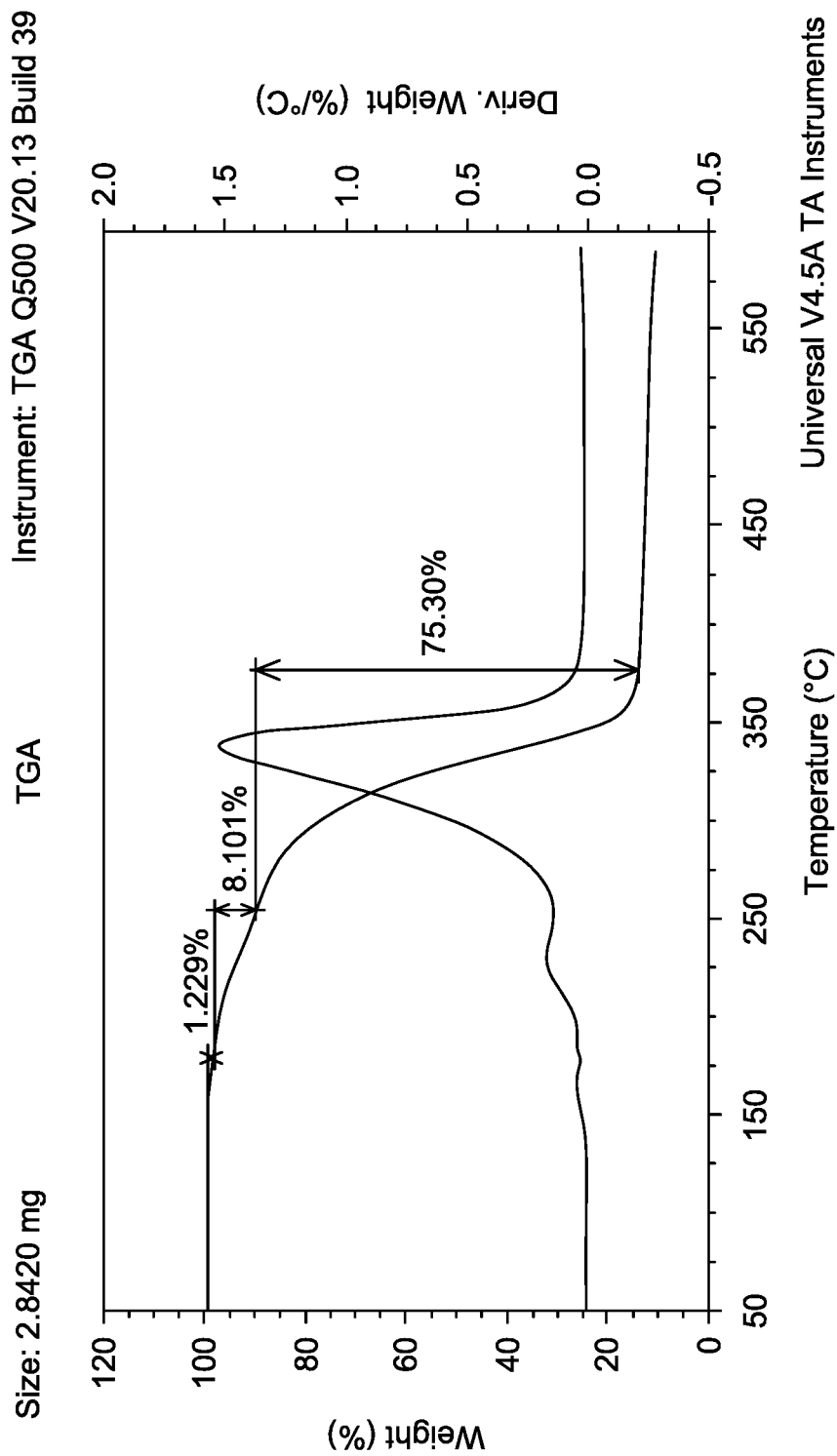
FIG. 19 shows a TGA profile of Formula IC.

In some embodiments, Formula IC can be characterized by a TGA profile substantially as shown in FIG. 19 when heated at a rate of 20° C./min. As FIG. 19 shows, Formula IC lost about 9.3% of its weight upon heating to about 275° C.

In some embodiments of the present disclosure, Formula IC is characterized by an XRPD pattern comprising peaks at one or more of 11.4 18.4, 19.4, 19.9, 21.5, 26.3 30.2, and 33.1 degrees±0.2 degrees 2-theta, and a DSC thermogram comprising an endothermic peak at about 190° C. when heated at a rate of 10° C./min.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%), 100% o, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

In some embodiments, the pharmaceutical composition comprises a compound of formula IA, microcrystalline cellulose, crospovidone, sodium lauryl sulfate, and magnesium stearate.

In some embodiments, the pharmaceutical composition comprises a compound of formula IA, mannitol, microcrystalline cellulose, crospovidone, sodium lauryl sulfate, and magnesium stearate.

In some embodiments, the pharmaceutical composition comprises a compound of formula IA-Form I, mannitol, microcrystalline cellulose, crospovidone, sodium lauryl sulfate, and magnesium stearate.

In some embodiments, the pharmaceutical composition comprises a compound of formula IA-Form II, mannitol, microcrystalline cellulose, crospovidone, sodium lauryl sulfate, and magnesium stearate.

In some embodiments, the pharmaceutical composition comprises a compound of formula IA-Form IIa, mannitol, microcrystalline cellulose, crospovidone, sodium lauryl sulfate, and magnesium stearate.

In some embodiments, the pharmaceutical composition comprises a compound of formula IA-Form III, mannitol, microcrystalline cellulose, crospovidone, sodium lauryl sulfate, and magnesium stearate.

In some embodiments, the pharmaceutical composition comprises a compound of formula IA-Form IV, mannitol, microcrystalline cellulose, crospovidone, sodium lauryl sulfate, and magnesium stearate.

In some embodiments, the pharmaceutical composition comprises a compound of formula IB, mannitol, microcrystalline cellulose, crospovidone, sodium lauryl sulfate, and magnesium stearate.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a PRMT5 inhibitor with an IC50 value of about or less than a predetermined value, as ascertained in an in vitro assay. In some embodiments, the PRMT5 inhibitor inhibits PRMT5 a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 µM, 100 µM, 200 µM, 300 µM, 400 µM, or 500 µM, or less, (or a number in the range defined by and including any two numbers above).

In some embodiments, the PRMT5 inhibitor selectively inhibits PRMT5 a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other PRMTs.

In some embodiments, the PRMT5 inhibitor selectively inhibits PRMT5 a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other PRMTs.

The subject methods are useful for treating a disease condition associated with PRMT5. Any disease condition that results directly or indirectly from an abnormal activity or expression level of PRMT5 can be an intended disease condition.

Different disease conditions associated with PRMT5 have been reported. PRMT5 has been implicated, for example, in a variety of human cancers as well as a number of hemoglobinopathies.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CIVIL), mastocytosis, chronic lymphocytic leukemia (CLL), multiple myeloma (MM), myelodysplastic syndrome (MDS), epidermoid cancer, or hemoglobinopathies such as b-thalassemia and sickle cell disease (SCD).

In yet other embodiments, said method is for treating a disease selected from CDKN2A deleted cancers; 9P deleted cancers; MTAP deleted cancers; spliceosome mutant cancers, glioblastoma, NSCLC, head and neck cancer, bladder cancer, or hepatocellular carcinoma.

In other embodiments, said method is for treating a disease selected from breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; spliceosome mutant cancers, glioblastoma, NSCLC, head and neck cancer, bladder cancer, hepatocellular carcinoma, adenoid cystic carcinoma (ACC), primary central nervous system lymphoma, fallopian tube cancer, or non-Hodgkin lymphoma.

In other embodiments, said method is for treating a disease selected from adenoid cystic carcinoma (ACC), primary central nervous system lymphoma, fallopian tube cancer, or non-Hodgkin lymphoma.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

In other aspects, compounds of the disclosure, as well as pharmaceutical compositions comprising them, can be administered to treat any of the described diseases, alone or in combination with one or more other chemotherapeutic agents. Examples of other chemotherapeutic agents include, for example, abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat, and zoledronate, as well as any combination thereof.

In other aspects, the other agent is a therapeutic agent that targets an epigenetic regulator. Examples of epigenetic regulator agents include, for example, bromodomain inhibitors, the histone lysine methyltransferases, histone arginine methyl transferases, histone demethylases, histone deacetylases, histone acetylases, and DNA methyltransferases, as well as any combination thereof. Histone deacetylase inhibitors are preferred in some aspects, and include, for example, vorinostat.

In other methods wherein the disease to be treated is cancer or another proliferative disease, the compounds of the disclosure, as well as pharmaceutical compositions comprising them, can be administered in combination with targeted therapy agents. Targeted therapies include, for example, JAK kinase inhibitors (e.g. Ruxolitinib), PI3 kinase inhibitors (including PI3K-delta selective and broad spectrum PI3K inhibitors), MEK inhibitors, Cyclin Dependent kinase inhibitors (e.g., CDK4/6 inhibitors), BRAF inhibitors, mTOR inhibitors, proteasome inhibitors (e.g., Bortezomib, Carfilzomib), HDAC-inhibitors (e.g., panobinostat, vorinostat), DNA methyl transferase inhibitors, dexamethasone, bromo and extra terminal family members, BTK inhibitors (e.g., ibrutinib, acalabrutinib), BCL2 inhibitors (e.g., venetoclax), MCL1 inhibitors, PARP inhibitors, FLT3 inhibitors, and LSD1 inhibitors, as well as any combination thereof.

In other methods wherein the disease to be treated is cancer or another proliferative disease, the compounds of the disclosure, as well as pharmaceutical compositions comprising them, can be administered in combination with an immune checkpoint inhibitor agents. Immune checkpoint inhibitors include, for example, inhibitors of PD-1, for example, an anti-PD-1 monoclonal antibody. Examples of anti-PD-1 monoclonal antibodies include, for example, nivolumab, pembrolizumab (also known as MK-3475), pidilizumab, SHR-1210, PDR001, and AMP-224, as well as combinations thereof. In some aspects, the anti-PD1 antibody is nivolumab. In some aspects, the anti-PD1 antibody is pembrolizumab. In some aspects, the immune checkpoint inhibitor is an inhibitor of PD-L1, for example, an anti-PD-L1 monoclonal antibody. In some aspects, the anti-PD-L1 monoclonal antibody is BMS-935559, MEDI4736, MPDL3280A (also known as RG7446), or MSB0010718C, or any combination thereof. In some aspects, the anti-PD-L1 monoclonal antibody is MPDL3280A or MEDI4736. In other aspects, the immune checkpoint inhibitor is an inhibitor of CTLA-4, for example, and anti-CTLA-4 antibody. In some aspects, the anti-CTLA-4 antibody is ipilimumab.

In other methods wherein the disease to be treated is cancer or another proliferative disease, the compounds of the disclosure, as well as pharmaceutical compositions comprising them, can be administered in combination with an alkylating agent (e.g., cyclophosphamide (CY), melphalan (MEL), and bendamustine), a proteasome inhibitor agent (e.g., carfilzomib), a corticosteroid agent (e.g., dexamethasone (DEX)), or an immunomodulatory agent (e.g., lenalidomide (LEN) or pomalidomide (POM)), or any combination thereof.

In some embodiments, the disease to be treated is an autoimmune condition or an inflammatory condition. In these aspects, the compounds of the disclosure, as well as pharmaceutical compositions comprising them, can be administered in combination with a corticosteroid agent such as, for example, triamcinolone, dexamethasone, fluocinolone, cortisone, prednisolone, or flumetholone, or any combination thereof.

In other methods wherein the disease to be treated is an autoimmune condition or an inflammatory condition, the compounds of the disclosure, as well as pharmaceutical compositions comprising them, can be administered in combination with an immune suppressant agent such as, for example, fluocinolone acetonide (RETISERT™), rimexolone (AL-2178, VEXOL™, ALCO™), or cyclosporine (RESTASIS™), or any combination thereof.

In some embodiments, the disease to be treated is beta-thalassemia or sickle cell disease. In these aspects, the compounds of the disclosure, as well as pharmaceutical compositions comprising them, can be administered in combination with one or more agents such as, for example, HYDREA™ (hydroxyurea).

In some aspects, the present invention is directed to methods of preparing the pharmaceutically acceptable salts described herein. In some embodiments, the methods of preparing the pharmaceutically acceptable salts are those described in the examples below.

The examples and preparations provided below further illustrate and exemplify the compounds of the present invention and methods of preparing such compounds. It is to be understood that the scope of the present invention is not limited in any way by the scope of the following examples and preparations.

EXPERIMENTAL PROCEDURES

Example 1. Synthesis of (2S,3S,4R,5R)-2-((R)-6-chloroisochroman-1-yl)-5-(4-methyl-7H-pyrrolo[2,3-d]pyrimidin-7-yl)tetrahydrofuran-3,4-diol (Formula I)

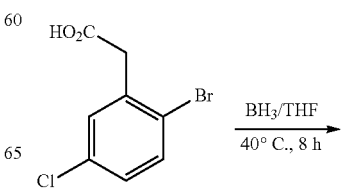

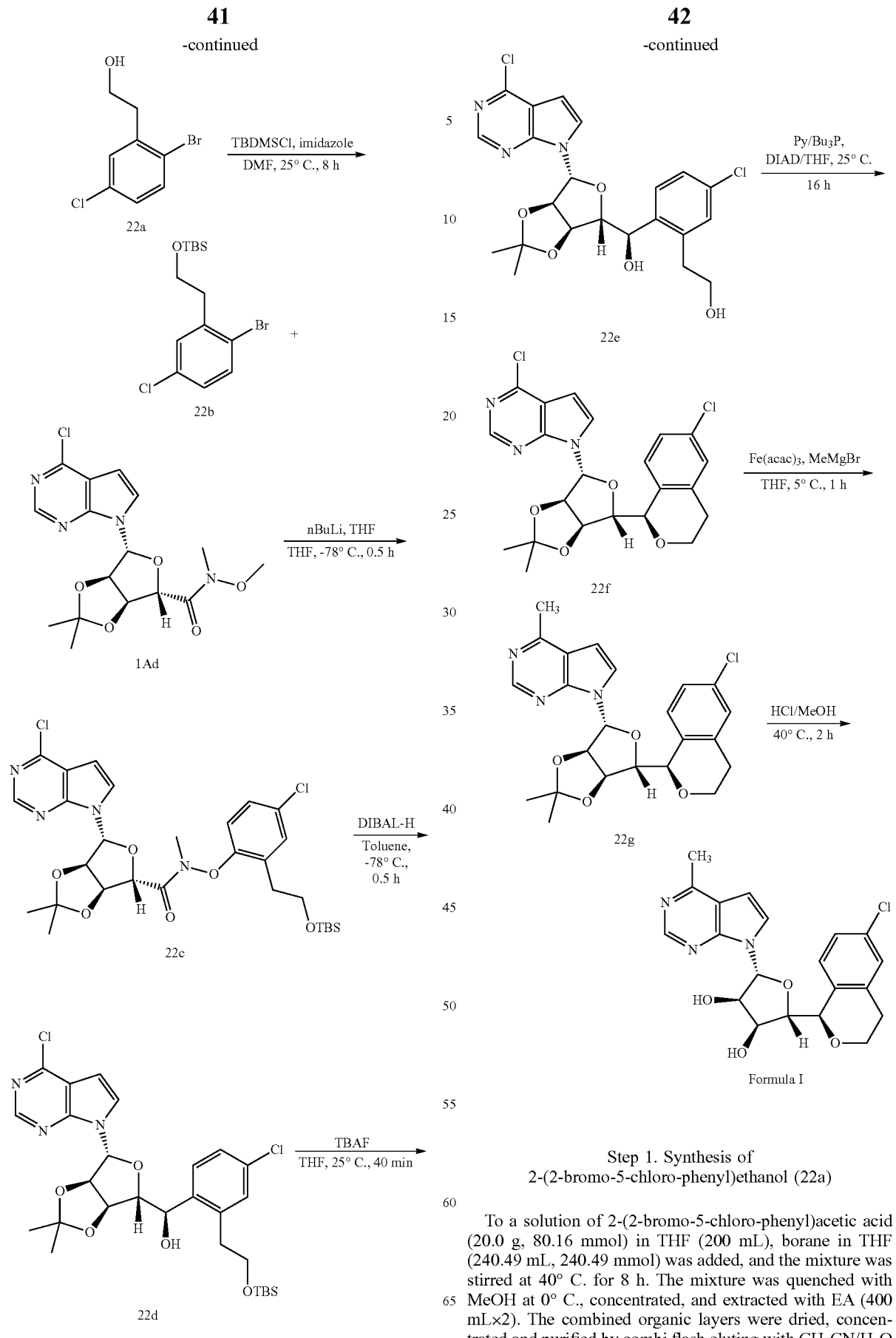

Step 1. Synthesis of
2-(2-bromo-5-chloro-phenyl)ethanol (22a)

To a solution of 2-(2-bromo-5-chloro-phenyl)acetic acid (20.0 g, 80.16 mmol) in THF (200 mL), borane in THF (240.49 mL, 240.49 mmol) was added, and the mixture was stirred at 40° C. for 8 h. The mixture was quenched with MeOH at 0° C., concentrated, and extracted with EA (400 mL×2). The combined organic layers were dried, concentrated and purified by combi flash eluting with CH₃CN/H₂O

Step 2. Synthesis of 2-(2-bromo-5-chloro-phenyl) ethoxy-tert-butyl-dimethyl-silane (22b)

To a solution of 22a (18.1 g, 76.85 mmol) in DMF (200 mL), imidazole (7.85 g, 115.28 mmol) and TBDMSCl (13.9 g, 92.23 mmol) were added and the mixture was stirred at 25° C. for 8 h. EA (800 mL) was added and the mixture was washed with brine (400 mL×2). The organic layer was concentrated and purified by flash column (PE) to give 22b (26.7 g, 76.34 mmol, 99.3% yield) as a colorless oil.

Step 3. Synthesis of [2-[2-[tert-butyl(dimethyl)silyl]oxyethyl]-4-chloro-phenyl]-[(3aR,4R,6S,6aS)-4-(4-chloropyrrolo[2,3-d]pyrimidin-7-yl)-2,2-dimethyl-3 a,4,6,6a-tetrahydrofuro[3,4-d][1,3]dioxol-6-yl] methanone (22c)

To a solution of 22b (8.91 g, 25.6 mmol) in dry THF (50 mL) was added n-BuLi (12.8 mL, 20.48 mmol) at −78° C. and the mixture was stirred for 10 min under nitrogen. A solution of 1Ad (4.0 g, 10.24 mmol) in dry THF (20 mL) was added and the mixture was stirred for 5 min at −78° C. TLC (PE:EA=8:1) showed the reaction was complete. The reaction was poured into dilute HCl (pH 6; pH kept <8 during the process of quenching.) The mixture was extracted with EA (200 mL×2), the combined organic layers were dried, concentrated and purified by combi-flash eluting with $CH_3CN/H_2O$ (neutral) from 5/95 to 95/5 to give 22c (5.1 g, 8.60 mmol, 84% yield) as yellow solid.

Step 4. Synthesis of (R)-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]—[2-[[tert-butyl(dimethyl)silyl]oxymethyl]-5-chloro-phenyl]methanol (22d)

To a solution of 22c (5.0 g, 8.44 mmol) in THF (30 mL) at −78° C., DIBAL-H (16.88 mL, 25.31 mmol) was added and the mixture was stirred at −78° C. for 30 min. TLC (PE/EA=8/1) showed SM Rf=0.5 has been completely consumed with the main product Rf=0.4. The reaction was poured into dilute HCl (pH 6, 400 mL, keeping the pH<8 during the process of quenching.) The mixture was extracted with EA (300 mL×2) and the combined organic layers were dried and concentrated to give the crude 22d (5.0 g) as a yellow solid.

Step 5. Synthesis of 2-[5-chloro-2-[(R)-hydroxy-[(3aR,4R,6R,6aR)-4-(4-chloropyrrolo[2,3-d]pyrimidin-7-yl)-2,2-dimethyl-3a,4,6,6a-tetrahydrofuro[3,4-d][1,3]dioxol-6-yl]methyl]phenyl]ethanol (22e)

To a solution of 22d (3.0 g, 5.17 mmol) in THF (50 mL) was added tetrabutylammonium fluoride (5.17 mL, 5.17 mmol). The mixture solution was stirred at 25° C. for 40 min. The reaction mixture was poured into aqueous $NH_4Cl$ and extracted with EA (100 mL). The combined organic layers were washed with brine, dried over anhydrous $Na_2SO_4$ and the solvent was concentrated under reduced pressure. The crude product was purified by flash column (PE:EA=15:1 to 3:1) to give 22e (2 g, 4.08 mmol, 79% yield) as a white solid. LCMS [M+H]: 480.1.

(neutral) from 5/95 to 95/5 to give 22b (18.1 g, 76.854 mmol, 95.9% yield) as a colorless oil. LCMS [M-18]: 217.0/219.0.

Step 6. Synthesis of 4-chloro-7-[(3aR,4R,6R,6aR)-2,2-dimethyl-6-[(1R)-6-chloroisochroman-1-yl]-3a,4,6,6a-tetrahydrofuro[3,4-d][1,3]dioxol-4-yl]pyrrolo[2,3-d]pyrimidine (22f)

To a solution of 22e (2.0 g, 4.16 mmol) in THF (100 mL) and was added tributylphosphine (2.1 mL, 8.33 mmol), isopropyl (NE)-N-isopropoxycarbonyliminocarbamate (1.72 mL, 8.74 mmol) and pyridine (0.34 mL, 4.16 mmol), and the reaction mixture was stirred at 25° C. for 16 h. TLC (PE/EA=3/1, Rf=0.4) showed that the starting material was consumed. The solvent was removed in vacuo and the crude product was purified by column chromatography on silica gel using petroleum ether/EtOAc (10:1-5:1) as eluent to give 22f (1.7 g, 3.68 mmol, 88% yield) as a yellow oil. LCMS [M+H]: 462.1.

Step 7. Synthesis of 4-methyl-7-[(3aR,4R,6R,6aR)-2,2-dimethyl-6-[(1R)-6-chloroisochroman-1-yl]-3a,4,6,6a-tetrahydrofuro[3,4-d][1,3]dioxol-4-yl]pyrrolo[2,3-d]pyrimidine (22g)

Methyl magnesium bromide (3.68 mL, 11.04 mmol) was added dropwise to a solution of ferric acetylacetonate (0.13 g, 0.37 mmol) and 22f (1.7 g, 3.68 mmol) in THF (100 mL) at 5° C. under nitrogen. The reaction mixture was warmed to rt and stirred for 1 h. TLC (EA:PE=1:1, Rf=0.3) showed the reaction was complete. Saturated $NH_4Cl$ was added dropwise to quench the reaction, which was extracted with EA (200 mL×2), then dried over $Na_2SO_4$ and concentrated. The residue was purified by flash column (PE:EA=10:1 to 1:1) to give 22g (900 mg, 1.93 mmol, 52.6% yield) as a white solid.

Step 8. Synthesis of (2R,3R,4S,5S)-2-(4-methylpyrrolo[2,3-d]pyrimidin-7-yl)-5-[(1R)-6-chloroisochroman-1-yl]tetrahydrofuran-3,4-diol (Formula I)

To a solution of HCl (6.0 mL, 12 mmol) in methanol (10 mL) and was added 22g (900 mg, 2.04 mmol) and the reaction mixture was stirred at 40° C. for 2 h. The reaction mixture was concentrated, and the residue was stirred with EA (50 mL) and filtered. The solid was purified by prep-HPLC eluting with $CH_3CN/H_2O$ (0.1% $NH_4OH$) from 5/95 to 95/5. The product fractions were extracted with EA (100 mL×2) and the extracts concentrated to yield Formula I (550 mg, 1.34 mmol, 66% yield) as a white solid. LCMS [M+H]: 402.3. $^1H$ NMR (400 M Hz, DMSO-$d_6$): δ 8.67 (s, 1H), 7.76 (d, J=4.0 Hz, 1H), 7.22-7.31 (m, 3H), 6.81 (d, J=3.6 Hz, 1H), 6.31 (d, J=7.6 Hz, 1H), 5.26 (d, J=7.2 Hz, 1H), 5.13 (d, J=4.0 Hz, 1H), 4.90 (d, J=3.6 Hz, 1H), 4.48-4.54 (m, 1H), 4.42-4.43 (m, 1H), 4.23-4.27 (m, 1H), 3.84-3.86 (m, 1H), 3.66-3.72 (m, 1H), 2.91-2.99 (m, 1H), 2.70-2.74 (m, 1H), 2.67 (s, 3H). $^1H$ NMR (400 M Hz, DMSO-$d_6$+D20): δ 8.86 (s, 1H), 7.77 (d, J=4 Hz, 1H), 7.22-7.31 (m, 3H), 6.82 (d, J=3.6 Hz, 1H), 6.31 (d, J=7.6 Hz, 1H), 4.90 (d, J=3.6 Hz, 1H), 4.49-4.53 (m, 1H), 4.42-4.43 (m, 1H), 4.24-4.28 (m, 1H), 3.83-3.85 (m, 1H), 3.66-3.72 (m, 1H), 2.91-2.99 (m, 1H), 2.70-2.75 (m, 1H), 2.69 (s, 3H).

Example 2. Synthesis of (2S,3S,4R,5R)-2-((R)-6-chloroisochroman-1-yl)-5-(4-methyl-7H-pyrrolo[2,3-d]pyrimidin-7-yl)tetrahydrofuran-3,4-diol (Formula I)

Added 5.84 g Formula IA to a 250 mL round bottom flask. Added 60 mL of de-ionized water and stirred for 5 min to give a suspension (pH 1.6). Added slowly 2.5 mL concentrated NH₄OH (37%) and stirred to give a slurry (pH 10). Stirred 3 hours, pH 10. Filtered the batch, washed with 200 mL water first, then with 200 mL heptane. Dried the product on filter in an oven under vacuum (temperature 40° C.) to give 5.20 g (98.0%) of Formula I. HPLC purity was 99.7%. The Formula I was crystalline by XRPD.

Figure 21:
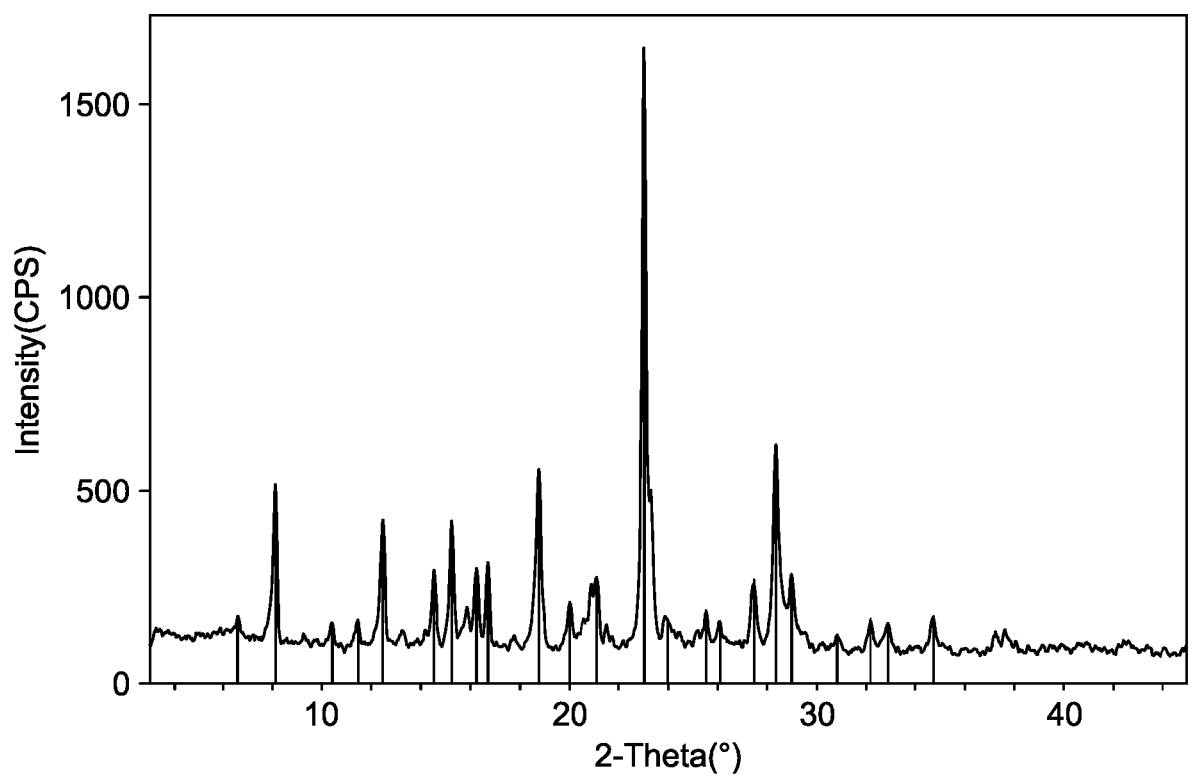
FIG. 21 shows an XRPD of Formula I free base.

In some embodiments, the Formula I free base may have the following XRPD peaks (See FIG. 21):

| Angle (degrees 2-theta ± 0.2 degrees 2-theta) | d Value (Å) | Relative Intensity |
| --- | --- | --- |
| 6.561 | 13.4599 | 3.8 |
| 8.079 | 10.935 | 26.6 |
| 10.415 | 8.4866 | 4.3 |
| 11.456 | 7.7179 | 4.7 |
| 12.44 | 7.1093 | 21.6 |
| 14.52 | 6.0955 | 12.8 |
| 15.221 | 5.8162 | 19.9 |
| 16.221 | 5.4599 | 13.3 |
| 16.698 | 5.3049 | 13.5 |
| 18.74 | 4.7311 | 30.5 |
| 20 | 4.4358 | 7.4 |
| 21.099 | 4.2071 | 12 |
| 23.02 | 3.8603 | 100 |
| 23.978 | 3.7083 | 3.8 |
| 25.521 | 3.4873 | 6 |
| 26.096 | 3.4119 | 3.8 |
| 27.459 | 3.2455 | 10.8 |
| 28.34 | 3.1466 | 34.1 |
| 28.98 | 3.0786 | 12.6 |
| 30.82 | 2.8988 | 3 |
| 32.18 | 2.7793 | 5.9 |
| 32.899 | 2.7202 | 5.1 |
| 34.719 | 2.5817 | 6.3 |

Example 3

Solids could be obtained by treatment of the Formula I free base with phosphoric, sulfuric, hydrochloric, ascorbic, L-tartaric acid, ethane-1,2-disulfonic acid, and 1-hydroxy-2-naphthoic acid, and oxalic acids.

Example 4. Synthesis of the Hydrochloride Salt of (2S,3S,4R,5R)-2-((R)-6-chloroisochroman-1-yl)-5-(4-methyl-7H-pyrrolo[2,3-d]pyrimidin-7-yl)tetrahydrofuran-3,4-diol (Formula IA)

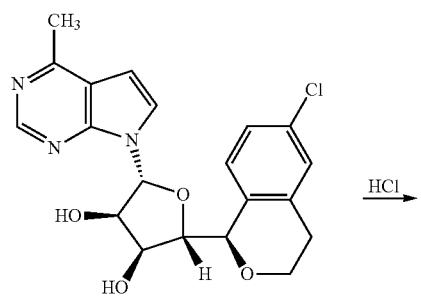

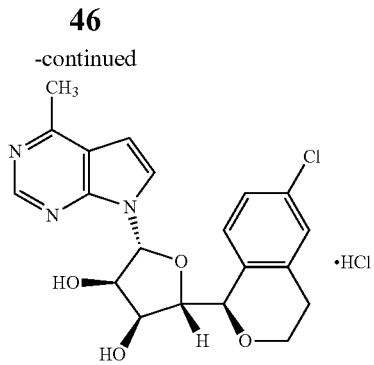

To 60 mg of Formula I free base (0.150 mmol) was added 1.5 mL of dichloromethane (DCM) and 2.0 mL of acetonitrile and the mixture was stirred to give a clear solution. Hydrochloric acid (1 M solution in isopropanol; 0.165 mL, 0.165 mmol, 1.10 eq) was added and the resulting mixture was stirred at room temperature for 40 min. The DCM was removed at 40-45° C. to give a slurry. The slurry was stirred at 65° C. for 60 min, and then cooled to room temperature and stirred for 2 h. The mixture was filtered and washed with methyl t-butyl ether (MTBE). The filter cake was dried at 45-48° C., under vacuum overnight to give 48.0 mg of the hydrochloride salt (Formula IA).

The XRPD of the hydrochloride salt is shown in FIG. 1.
The DSC of the hydrochloride salt is shown in FIG. 2.
The TGA of the hydrochloride salt is shown in FIG. 3.
The crystalline HCl salt formed by this procedure is Formula IA-Form I.

Example 5. Synthesis of the Hydrochloride Salt of (2S,3S,4R,5R)-2-((R)-6-chloroisochroman-1-yl)-5-(4-methyl-7H-pyrrolo[2,3-d]pyrimidin-7-yl)tetrahydrofuran-3,4-diol (Formula IA)

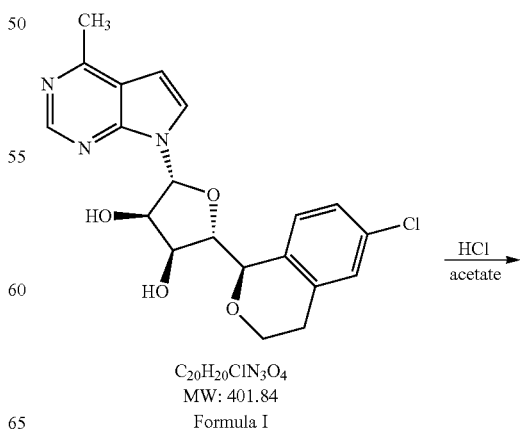

$C_{20}H_{20}ClN_3O_4$
MW: 401.84
Formula I

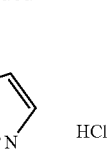
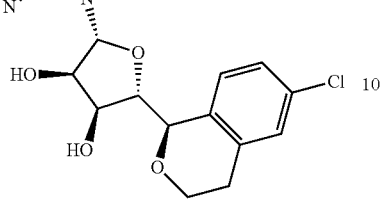

C20H21Cl2N3O4
MW: 438.30
Formula IA

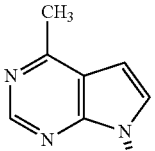
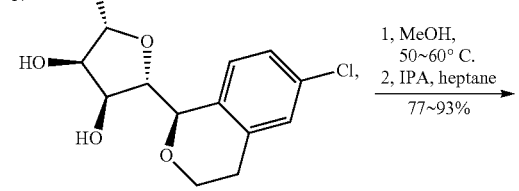

Formula IA
C20H21Cl2N3O4
MW: 438.31

1, MeOH, 50~60° C.
2, IPA, heptane
77~93%

Formula IA
C20H21Cl2N3O4
MW: 438.31

To 100.3 mg of Formula I (0.25 mmol, 1.0 eq.) was added 4.0 mL of acetone and stirred for 5 minutes. 265 μL of 1.0 M HCl in IPA (0.263 mmol, 1.06 eq.) was added. The resulting mixture was stirred to give a thin slurry, and then continuously stirred overnight. The mixture was filtered to give a solid which was dried at 40° C. under vacuum overnight to give 98.8 mg (yielding 90.0%) of the salt (Formula IA). The purity of the salt was 99.2% by HPLC. The crystallinity of the salt was confirmed by XPRD. The HPLC peak area comparison of the salt and the free base showed that the ratio of the free base and hydrochloric acid was approximately 1:1.

Example 6. Synthesis of the Hydrochloride Salt of (2S,3S,4R,5R)-2-((R)-6-chloroisochroman-1-yl)-5-(4-methyl-7H-pyrrolo[2,3-d]pyrimidin-7-yl)tetrahydrofuran-3,4-diol (Formula IA)

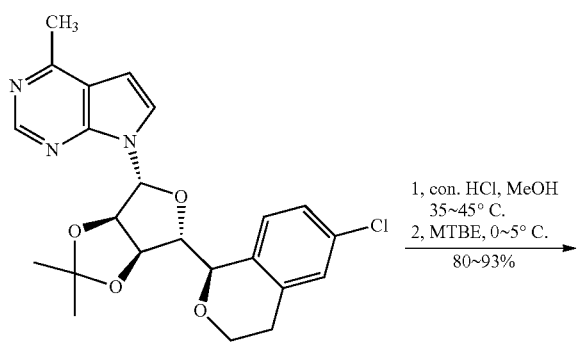

PRT1063
C23H24ClN3O4
MW: 441.91

1, con. HCl, MeOH 35~45° C.
2, MTBE, 0~5° C.
80~93%

To a clean and dried RBF were charged crude PRT1063, 3476.2 g, (containing 1829.0 g of PRT1063 based on the theoretical yield from previous steps) and MeOH (18.3 L). After charging con. HCl (1720 mL, 5.0 eq) into the reactor, the resulting solution was stirred at 35-45° C. for about 8 hours. MTBE (55.0 L) was added into the reaction, and the resulting slurry was stirred at rt for about 2 h. The slurry was cooled to 0-5° C., and stirred for about 1 h. The slurry was filtered, and the filter cake was transferred back to the RBF. MTBE (9.1 L) was charged and the slurry was stirred at rt for 0.5-1 hour. The slurry was filtered, and the filter cake was washed with MTBE (3.7 L). The filter cake was then dried on the funnel by vacuum for NLT 2 hours.

Re-crystallization of Formula IA: To a clean and dried RBF were charged Formula IA, (1500 g) and MeOH (15 L). The mixture was heated to 50-60° C. and stirred to form a clear solution. The solution was cooled to 20-30° C., and filtered through a fritted glass funnel. The filtrate was transferred to a clean and dried reactor, and the volume of filtrate in the reactor was recorded. The funnel was washed with MeOH (3.0 L). This washing MeOH was used to rinse the filtrate receiving flask before adding to the reactor. Distillation equipment was assembled to the reactor. The filtered solution in the reactor was heated to reflux and distillate was collected. While maintaining distillation in the reactor, IPA (15 L) was gradually added to the reactor in the speed to maintain the initial recorded volume of the solution. After the addition of IPA, heptane (22.5 L) was gradually added into the reactor while maintaining the distillation until the internal volume reached the recorded volume. The heating was stopped, and the slurry was cooled to 15-25° C. The slurry was stirred at 15-25° C. for about 2 hours. The batch was filtered, and the filter cake was washed with heptane (4.5 L). The product was dried on the filter for NLT 2 hours by pulling air through the filter cake. The filter cake was transferred to trays and dried in oven at 50° C. under vacuum to constant weight.

Example 7

Polymorphic forms of Formula IA have been identified as described below. These polymorphs—Formula IA-Form I, Formula IA-Form II, Formula IA-Form IIa, Formula IA-Form III, Formula IA-Form IV—may be prepared using the methods described below.

Solubility of HCl Salt at 21±1° C. and at 50±1° C.

3 mL of the tested solvent was added to a 4 mL of vial. Formula IA was added until a cloudy solution was obtained at 21±1° C. About 30 mg additional Formula IA was added to the cloudy solution. The mixture was agitated at 21±1° C. for a weekend, during which the temperature was controlled by IKA® ETS-D5 temperature controller and IKA® RCT basic safety control. The mixture was filtered using a syringe filter (PTFE, 0.22 μL, 13 mm, Agela Technologies Inc.). The satuatred solution was transferred into an HPLC vial, diluted with methanol, and analyzed by HPLC.

2 mL of the tested solvent was added to a 4 mL of vial. Formula IA was added until a cloudy solution was obtained at 50±1° C. About 30 mg additional Formula IA was added to the cloudy solution. The mixture was agitated at 50±1° C. for 24 hr, during which the temperature was controlled by IKA® ETS-D5 temperature controller and IKA® RCT basic safety control. The mixture was filtered using a syringe filter (PTFE, 0.22 μL, 13 mm, Agela Technologies Inc.). The saturated solution was transferred into an HPLC vial, diluted with methanol, and analyzed by HPLC. The results are shown in Table 8.

TABLE 8

| Solvent | Solubility at 21 ± 1° C. (mg/mL) | Solubility at 50 ± 1° C. (mg/mL) |
|---|---|---|
| MeCN | 0.69 | 1.05 |
| Methanol | >50 | >50 |
| EtOH | 7.64 | 10.80 |
| EtOAc | 0.12 | 0.16 |
| IPAc | 0.16 | 0.24 |
| IPA | 0.96 | 1.99 |
| Water | 14.68 | 43.76 |

Phase Equilibration at 25±1° C. and at 50±1° C.

Phase equilibration studies were designed to provide information on a predominant crystal form. Formula IA was equilibrated in solvents at 25±1° C. and at 50±1° C. temperature was controlled by IKA® ETSD5 temperature controller and IKA® RCT basic safety control.

To about 3 mL of solvent was added Formula IA Form I until a cloudy solution was obtained, then, about 20 mg of additional Formula IA Form I was added to the cloudy solution. The mixture was stirred at 25±1° C. and at 50±1° C. for 2.0 days. The solid was filtered and analyzed by XRPD.

In these experiments, polymorphic Form II (Formula IA-Form II) was obtained from phase equilibration in ethanol at 25° C., and polymorphic Form III (Formula IA-Form III) was obtained from water at 21° C. (Table 2). Phase equilibration at 50±1° C. (Table 3) resulted in polymorphic Form III from water, and Form I was obtained from the other solvents. The results are shown in Table 9.

TABLE 9

| | Polymorphic Form Obtained | |
|---|---|---|
| Solvent | 25 ± 1° C. | 50 ± 1° C. |
| acetonitrile | I | I |
| methanol | I | I |
| ethanol | II | I |
| Ethyl acetate | I | I |
| Isopropyl acetate | I | I |
| isopropanol | I | I |
| water | III | III |

Evaporation Studies

Evaporation studies were carried out to identify the predominant crystal form during uncontrolled evaporation. Experiments that did not result in any particulate solids (i.e., clear thin films and oils) were not studied further. XRPD was used to study the solid-state morphology of the crystalline forms of the evaporation samples at 20° C. and 50° C. In these studies, a saturated solution prepared from Formula IA-Form I was evaporated. The results are shown in Table 10.

TABLE 10

| | Polymorphic Form Obtained | |
|---|---|---|
| Solvent | 20 ± 1° C. | 50 ± 1° C. |
| acetonitrile | N/A | N/A |
| methanol | I | I |
| ethanol | I | I |
| Ethyl acetate | N/A | N/A |
| Isopropyl acetate | N/A | N/A |
| isopropanol | IV | IV (see FIG. 11) |
| water | N/A | N/A |

Anti-Solvent Addition Experiments

Saturated solution or nearly saturated solutions of Formula IA were prepared by adding Formula IA-Form I to a solvent. An anti-solvent was added to induce precipitation. Hexane, heptane, methyl t-butyl ether (MTBE), toluene, ethyl acetate, acetone, methyl ethyl ketone (MEK), isopropanol (IPA), tetrahydrofuran (THF), acetonitrile and isopropyl acetate (IPAc) were used as the anti-solvents. Experiments that did not produce any particulate solids on anti-solvent addition were not studied further. The results are presented in Table 11 below.

TABLE 11

| Antisolvent (mL) | Solvent (mL) | Polymorphic Form Obtained |
|---|---|---|
| MTBE (1.2) | MeOH (0.6) | IV |
| IPAc (1.2) | MeOH (0.6) | IV |
| IPA (2.5) | MeOH (0.6) | IV |
| EtOAc (1.5) | MeOH (0.6) | IV |
| THF (2.8) | MeOH (0.6) | IV |
| MEK (2.8) | MeOH (0.6) | I |
| Acetone (2.8) | MeOH (0.6) | I |
| Toluene (3.0) | MeOH (0.6) | N/A |
| Acetonitrile (3.0) | MeOH (0.6) | N/A |
| MTBE (4.0) | EtOH (2.5) | IV |
| Heptane (4.0) | EtOH (2.5) | IV |
| Hexanes (4.0) | EtOH (2.5) | IV |
| Toluene (4.5) | EtOH (2.5) | N/A |
| Cyclo-hexane (4.0) | EtOH (2.5) | IV |
| Ethyl acetate (4.0) | EtOH (2.5) | N/A |
| Heptane (3.5) | IPA (3.0) | IV |
| Hexanes (3.5) | IPA (3.0) | IV |
| MTBE (5.0) | IPA (3.0) | N/A |
| THF (4.0) | Water (2.5) | N/A |
| IPA (4.0) | Water (2.5) | N/A |
| 1-propanol (4.0) | Water (2.5) | N/A |
| Acetone (4.0) | Water (2.0) | N/A |
| Acetonitrile (4.0) | Water (2.5) | N/A |
| MEK (4.0) | Water (2.0) | N/A |
| 1,4-Dioxane (4.0) | Water (2.0) | N/A |

Reverse Addition Experiments

Saturated or nearly saturated solutions of Formula IA were prepared from Formula IA-Form I in a solvent. This solution was then added to a larger volume of a miscible anti-solvent. Hexane, heptane, MTBE, toluene, ethyl acetate, acetone, MEK, IPA, THF, acetonitrile and IPAc were used as the anti-solvents. Experiments that did not produce any particulate solids upon addition to the antisolvent were not studied further. The results are presented in Table 12 below.

TABLE 12

| Antisolvent (mL) | Solvent (mL) | Polymorphic Form Obtained |
|---|---|---|
| MTBE (2.8) | MeOH (0.5) | IV |
| IPAc (2.5) | MeOH (0.5) | IV |
| IPA (3.0) | MeOH (0.8) | IV |
| EtOAc (2.5) | MeOH (0.6) | IV |
| THF (2.5) | MeOH (0.6) | IV |
| Toluene (3.0) | MeOH (0.8) | N/A |
| MEK (2.8) | MeOH (0.6) | N/A |
| Acetone (3.0) | MeOH (0.6) | I |
| MTBE (4.3) | EtOH (2.5) | IV |
| Heptane (4.0) | EtOH (2.5) | IV |
| Hexanes (4.0) | EtOH (2.5) | IV |
| IPAc (4.0) | EtOH (2.5) | IV |
| Toluene (4.5) | EtOH (2.5) | N/A |
| Cyclohexane (4.0) | EtOH (2.5) | IV |
| Ethyl acetate | EtOH (2.5) | N/A |
| Heptanes (6.5) | IPA (3.0) | IV |
| Hexanes (6.5) | IPA (3.0) | IV |
| MTBE (8.0) | IPA (3.0) | IV |
| THF (4.0) | Water (2.5) | N/A |
| IPA (4.0) | Water (2.5) | N/A |
| 1-propanol (4.0) | Water (2.0) | N/A |
| Acetone (4.0) | Water (2.0) | N/A |
| Acetonitrile (4.0) | Water (2.5) | N/A |
| MEK (4.0) | Water (2.0) | N/A |
| 1,4-dioxane (4.0) | Water (2.0) | N/A |

Cooling of Saturated Solutions

Saturated or nearly saturated solutions of Formula IA-Form I in methanol or ethanol were prepared at room temperature and were quenched to about −40° C. A saturated solution in water was prepared at 35° C. and it was quenched to about 5° C. Both experiments were designed to induce precipitation of higher energy forms. The results of these experiments are shown in Table 13 below.

TABLE 13

| Solvent (mL) | Polymorphic Form Obtained |
|---|---|
| MeOH | N/A |
| EtOH | II |
| water | III |

Competitive Slurry Experiment

To evaluate the transformation of Formula IA solid forms, competitive slurry experiments were performed as follows. Formula IA was added to the solvent mixture until a saturated solution formed. An additional 8 mg of Formula IA-Form I was then added, in addition to 8 mg each of Formula IA-Form IIa, Formula IA-Form III, and Formula IA-Form IV. The slurries were stirred and analyzed by XRPD at various time points including overnight and 24 hours. The results are shown in Table 14.

TABLE 14

| | Polymorphic Form Obtained | |
|---|---|---|
| Solvent | Solid State Form (after overnight) | Solid State Form (after 24 h) |
| MeOH/IPA (40/60) | I | I |
| MeOH/IPA (20/80) | I | I |
| MeOH/IPA/Heptane (30/50/20) | I | I |
| Ethyl acetate | N/A | N/A |

TABLE 14-continued

| | Polymorphic Form Obtained | |
|---|---|---|
| Solvent | Solid State Form (after overnight) | Solid State Form (after 24 h) |
| Isopropyl acetate | N/A | N/A |
| isopropanol | IV | IV |
| water | N/A | N/A |

Representative Synthetic Procedures
Formula IA-Form II

To about 3 mL of saturated of drug substance prepared in ethanol was added about 50 mg of drug substance followed by stirring at 25±1° C. for 2 days, which was filtered, air-dried in hood for 24 h, and analyzed by XRPD as Formula IA-Form II. See FIG. 4, FIG. 5.

3.0 mL of saturated solution in ethanol was quenching cooled to −20° C., and kept at the temperature for 30 min. to give slurry, which was filtered and air-dried. The solid was analyzed by XRPD and assigned as Formula IA-Form II.
Formula IA-Form IIa Formula IA-Form IIa was formed by drying Formula IA-Form II under vacuum at 48-50° C. for 24 hours.
Formula IA-Form III To about 3 mL of saturated of drug substance prepared in water was added about 50 mg of drug substance followed by stirring at 25±1° C. for 2 days, which was filtered, air-dried in hood for 24 h, and analyzed by XRPD as Formula IA-Form III. See FIG. 8, FIG. 10.

3.0 mL of saturated solution in water was quenching cooled to 2-3° C., and kept at the temperature for 1.0 h. to give slurry, which was filtered and air-dried. The solid was analyzed by XRPD and assigned as Formula IA-Form III. See FIG. 9.
Formula IA-Form IV To 2.5 mL of ethyl acetate was added 0.6 mL of the solution of drug substance prepared in MeOH (50 mg/mL) followed by stirring about 5 min, of which the solid was filtered and analyzed by XRPD as Formula IA-Form IV. See FIG. 12 and FIG. 13.

To 0.6 mL of the solution of drug substance prepared in MeOH (50 mg/mL) was added 1.5 mL of ethyl acetate followed by stirring about 5 min, of which the solid was filtered and analyzed by XRPD as Formula IA-Form IV.

Example 8. Synthesis of the Phosphate Salt of (2S, 3S,4R,5R)-2-((R)-6-chloroisochroman-1-yl)-5-(4-methyl-7H-pyrrolo[2,3-d]pyrimidin-7-yl)tetrahydrofuran-3,4-diol (Formula IB)

To 50 mg of Formula I free base (0.125 mmol) was added 1.5 mL of isopropanol (IPA) and 1.0 mL of dichloromethane (DCM) and the mixture was stirred to give a clear solution. Phosphoric acid (1M solution in IPA; 0.15 mL, 0.15 mmol, 1.20 eq) was added and the resulting mixture was stirred at room temperature for 40 min. The DCM was removed at 40° C. to give a slurry. The slurry was stirred at 65° C. for 60 min, and then cooled to room temperature and stirred for 2 h. The mixture was filtered and washed with methyl t-butyl ether (MTBE). The filter cake was dried at 45-48° C., under vacuum overnight to give the phosphate salt (Formula IB).
The XRPD of this phosphate salt is shown in FIG. 14B.
The DSC of this phosphate salt is shown in FIG. 15B.
The TGA of this phosphate salt is shown in FIG. 16B.

Example 9. Synthesis of the Phosphate Salt of (2S, 3S,4R,5R)-2-((R)-6-chloroisochroman-1-yl)-5-(4-methyl-7H-pyrrolo[2,3-d]pyrimidin-7-yl)tetrahydrofuran-3,4-diol (Formula IB)

To 100.6 mg of Formula I free base (0.25 mmol, 1.0 eq.) was added 4.0 mL of EtOH. The resulting mixture was and stirred for 5 minutes. 263 µL of 1.0 M $H_3PO_4$ in IPA (0.263 mmol, 1.06 eq.) was added. The resulting mixture was stirred continuously overnight, and then filtered to give a solid. The filter cake was dried at 40° C. under vacuum overnight to give 86.7 mg, (69.3%) of the salt. The purity of the salt was 98.5% by HPLC. The HPLC peak area comparison of the salt and the free base indicated that the ratio of the free base and phosphoric acid was approximately 2:1.

The XRPD of this phosphate salt is shown in FIG. 14A.
The DSC of this phosphate salt is shown in FIG. 15A.
The TGA of this phosphate salt is shown in FIG. 16A.

Example 10. Synthesis of the tartrate salt of (2S, 3S,4R,5R)-2-((R)-6-chloroisochroman-1-yl)-5-(4-methyl-7H-pyrrolo[2,3-d]pyrimidin-7-yl)tetrahydrofuran-3,4-diol (Formula IC)

To 40.5 mg of L-tartaric acid (0.263 mmol, 1.05 eq.) was added 100.2 mg (0.25 mmol, 1.0 eq.) of Formula I. 4.0 mL of 2-butanone was added and the resulting mixture was stirred continuously overnight. The mixture was filtered to give a solid, which was washed with 2.5 mL MTBE. The filter cake was dried at 40° C. under vacuum overnight to give 68.8 mg, (yielding 50.0%) of the tartrate salt.

The stoichiometric ratio of the salt between Formula I and tartaric acid was determined by its $^1$H NMR spectrum (FIG. 20) as 2:1 (400 MHz in DMSO-$d_6$).

Figure 20:
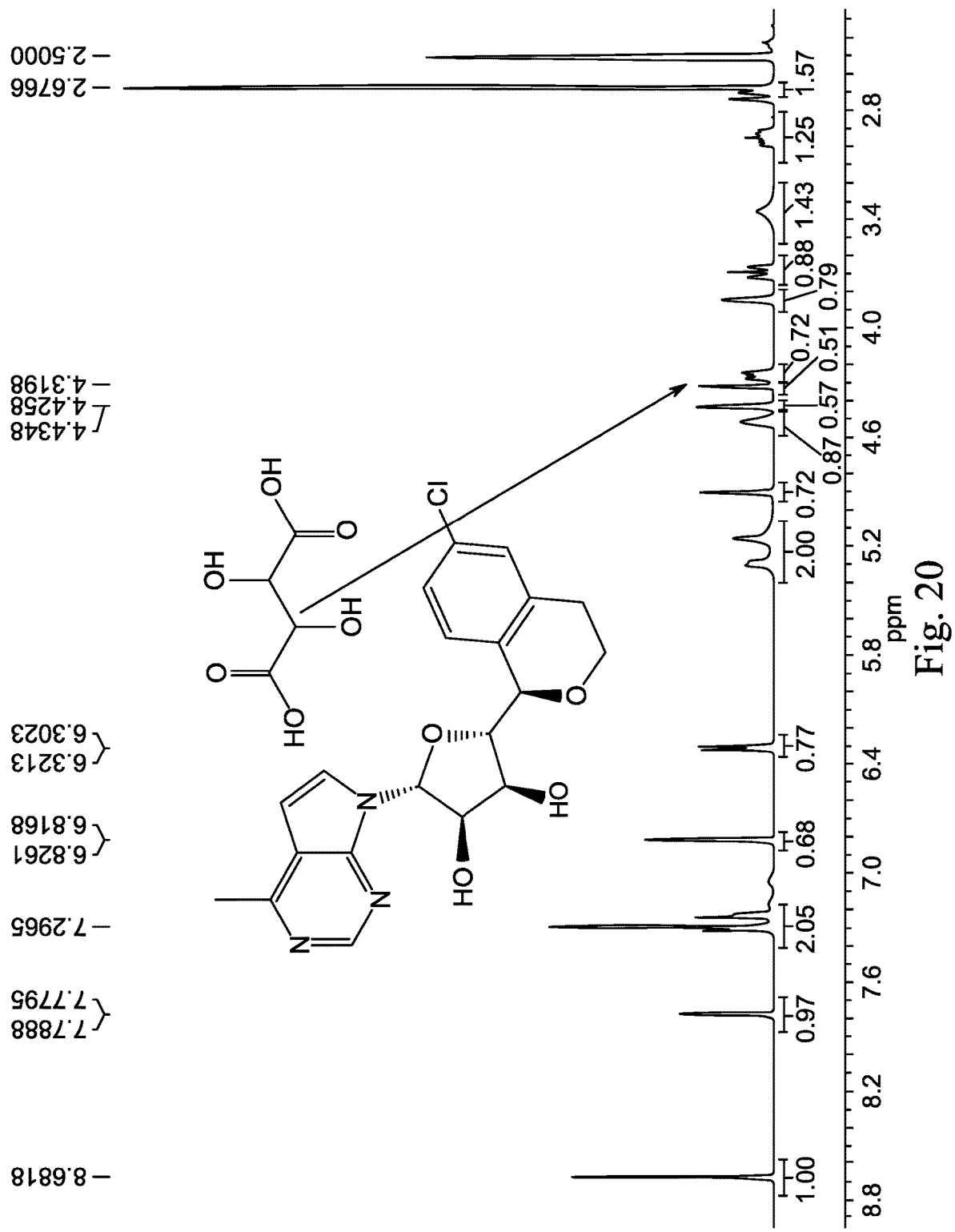
FIG. 20 shows a $^1$H NMR spectrum of Formula IC.

The XRPD of this tartrate salt is shown in FIG. 17.
The DSC of this tartrate salt is shown in FIG. 18.
The TGA of this tartrate salt is shown in FIG. 19.
The $^1$H NMR spectrum of the tartrate salt is shown in FIG. 20.

Instrument Methods
X-Ray Powder Diffraction (XRPD)

XRPD patterns also can be collected with a Rigaku MiniFlex X-ray Powder Diffractometer (XRPD) instrument. X-ray radiation is from Copper (Cu) at 1.54056 Å with $K_\beta$ filter. X-ray power: 30 KV, 15 mA.

Thermogravimetric Analysis (TGA) and Differential Scanning Calorimetry (DSC)

TGA can be collected using a TGA Q500 by TA Instruments using a scan rate of 20° C. per minute.

DSC can also be obtained using a TA Instrument Differential Scanning calorimetry, Model Q20 with autosampler, using a scan rate of 10° C./min, and nitrogen gas flow at 50 mL/min.

Biochemical Assay Protocol

Compounds were solubilized and 3-fold diluted in 100% DMSO. These diluted compounds were further diluted in the assay buffer (20 mM Tris-HCl, pH 8.0, 50 mM NaCl, 0.002% Tween20, 1 mM TCEP, 1% DMSO) for 10-dose $IC_{50}$ mode at a concentration 10-fold greater than the desired assay concentration. Standard reactions were performed in a total volume of 30 µL in assay buffer, with 300 nM histone H4 based AcH4-23 (Anaspec: AS-65002) as substrate. To this was added the PRMT5/MEP50 complex diluted to provide a final assay concentration of 2.5 nM and the compounds were allowed to preincubate for 20 minutes at 37° C. The reaction was initiated by adding S-[3H-methyl]-adenosine-L-methionine (PerkinElmer: NET155001MC) to a final concentration of 1 µM. Following a 30 minutes incubation at 37° C., the reaction was stopped by adding 25 µL of 8M Guanidine HCl. Prepare streptavidin YSI SPA beads (PerkinElmer: RPNQ0012) at 0.3 mg/mL in assay buffer. To each reaction, add 150 µL of SPA beads suspension, and incubated while shaking at room temperature for 30 minutes. The plate was centrifuged at 100×g for 30 second before reading in a scintillation counter. $IC_{50}$ values were determined by fitting the data to the standard 4 parameters with Hill Slope using GraphPad Prism software. See Table 15, below (PRMT5 $IC_{50}$).

Cellular Assay Protocol
Cell treatment and Western Blotting for Detecting Symmetric Di-Methyl Arginine (sDMA) Marks Compound titration and cell culture: Compounds were dissolved in DMSO to make 10 mM stock and 3-fold series dilutions were further conducted to make working stocks top at 1 mM. Granta-519 cells were maintained in PRMI 1640 (Corning Cellgro, Catalog #: 10-040-CV) supplemented with 10% v/v FBS (GE Healthcare, Catalog #: SH30910.03) and U-87 MG cells were maintained in DMEM (Corning Cellgro, Catalog #: 10-013-CV) with 10% FBS and 2 mM Glutamin (Corning Cellgro, Catalog #25005CV).

To determine enzyme inhibition $IC_{50}$ values in Granta-519 and U-87 MG cells using Western Blot analysis. One day before experiment, Granta-519 cells were passaged to a density of $0.5 \times 10^6$ cells/mL. U-87 MG cells were trypsinized and $4 \times 10^5$ cells were seeded into 6-well plates and allowed to grow overnight. The next day, Granta-519 cells were spun down at 1,500 rpm for 4 min, resuspended in fresh medium at $0.5 \times 10^6$ cells/ml and 3 mL of culture ($1.5 \times 10^6$ cells) were seeded into 6 well plate. Eight-point, 3-fold serial dilutions of compound working stocks were added to cells (3 µL, 1:1,000 dilution, DMSO concentration was 0.1%; final top concentration at 1 µM) and incubated for 3 days. Cells incubated with DMSO was used as a vehicle control.

Cells were harvested 3 days later, resuspended in 15 µL PBS, lysed in 4% SDS, and homogenized by passing through homogenizer column (Omega Biotek, Catalog #: HCR003). Total protein concentrations were determined by BCA assay (ThermoFisher Scientific, Catalog #: 23225). Lysates were mixed with 5× Laemmli buffer and boiled for 5 min. Forty µg of total protein was separated on SDS-PAGE gels (Bio-Rad, catalog #: 4568083, 4568043), transferred to PVDF membrane, blocked with 5% dry milk (Bio-Rad, Catalog #: 1706404) in TBS with 0.1% v/v Tween 20 (TBST) for 1 hour at room temperature (RT), and incubated with primary antibodies (sDMA: Cell signaling, Catalog #: 13222, 1:3,000; β-Actin: sigma, Catalog #: 1:5,000) in 5% dry milk in TBST at 4° C. overnight. The next day, membranes were washed with TBST, 5×5 min, and incubated with HRP conjugated seconded antibody (GE Healthcare; Catalog #: NA934-1ML, NA931-1ML; 1:5,000) for 2 hours at RT, followed by 5×5 min washes with TBST, and incubation with ECL substrates (Bio-Rad, Catalog #: 1705061, 1705062). Chemiluminescent signal was captured with Fluochem HD2 imager (Proteinsimple). SmD3me2s bands were quantified by ImageJ. Signals were normalized to β-Actin and DMSO control. $IC_{50}$ values were calculated using Graphpad Prism ([Inhibitor] vs. normalized response–Variable slope). See Table 15, below (sDMA $IC_{50}$).

Cell Proliferation Assay to Determine $IC_{50}$ in Granta-519 and U-87 MG Cells

One day before experiment, Granta-519 cells were passaged to a density of $0.5 \times 10^6$ cells/ml. U-87 MG cells were trypsinized and 2,000 cells were seeded into 96-well plates and allowed to grow overnight. On the day of experiment (day 0), Granta-519 Cells were spun down at 1,500 rpm for 4 min, resuspended in fresh medium to $0.5 \times 10^6$ cells/ml and 190 μL of cells were added to 96 well plates. For U-87 MG cells, old medium was removed and replaced with 190 uL fresh medium. Compound working stocks were first diluted at 1:50 with fresh medium in 96 well plate and 10 μL of diluted drugs were added to 96 well plates containing cells and incubated for 3 days. DMSO was used a vehicle control.

One day 3, 50 μL of Granta-519 cells were transferred to a new 96-well plate and 140 uL fresh medium was added. For U-87 MG cells, old medium was removed and replaced with 190 μL fresh medium. Compound working stocks were freshly diluted at 1:50 with medium and 10 μL of diluted drugs were added to cells and grow for 3 additional days. The same process was repeated on day 6. Cells were allowed to grow for an additional 4 days.

On day 10, 100 μL Granta-519 cells were transferred to a new 96 well plate and 10 μL of Cell Counting Kit-8 (CCK-8, Jojindo, CK04-13) solution was added. For U-87 MG cells, old medium was removed and replaced with 100 μL fresh medium and 10 μL CCK-8 solution was added. Plates were incubated in $CO_2$ incubator for 2 hours (Granta-519 cells) or 30 min (U-87 MG cells) and $OD_{450}$ values were measured with a microplate reader (iMark microplate reader, Bio-Rad). Percentage of viable cells, relative to DMSO vehicle control, were calculated and plotted in Graphpad Prism ([Inhibitor] vs. normalized response–Variable slope) to determine proliferation $IC_{50}$ values on day 10. See Table 15, below (Prolif. $IC_{50}$).

TABLE 15

Biochemical and cellular potency in U-87 MG cell line [Granta-519 cell line]

| Ex# | PRMT5 $IC_{50}$ μM | PRMT5 $IC_{50}$_N | sDMA $IC_{50}$ μM | sDMA $IC_{50}$_N | Prolif. $IC_{50}$ μM | Prolif. $IC_{50}$_N |
|---|---|---|---|---|---|---|
| Formula I (free base) | 0.0048 | 2 | 0.0176 | 2 | 0.054 | 3 |

In some embodiments, the disclosure is directed to the following aspects:

Aspect 1. A pharmaceutically acceptable salt of a compound of Formula I:

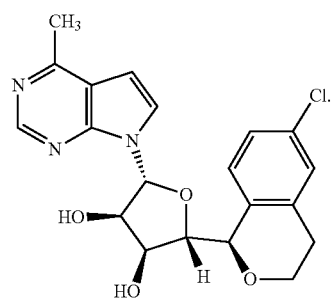

(I)

Aspect 2. The pharmaceutically acceptable salt of aspect 1, wherein the salt is the hydrochloride salt, Formula IA.

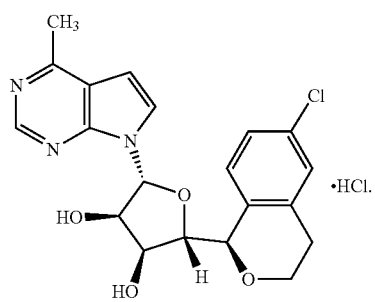

(IA)

Aspect 3. A crystalline form of the hydrochloride salt of aspect 2.

Aspect 4. The crystalline form of aspect 3, wherein said crystalline that is Formula IA-Form I.

Aspect 5. The crystalline form of aspect 3 or aspect 4, characterized by an X-ray powder diffraction pattern substantially as shown in FIG. 1.

Aspect 6. The crystalline form of any one of aspects 3, 4, or 5, characterized by an X-ray powder diffraction pattern comprising a peak at 23.8 degrees±0.2 degrees 2-theta, on the 2-theta scale with lambda=1.54 angstroms (Cu Kα).

Aspect 7. The crystalline form of any one of aspects 3-6, characterized by an X-ray powder diffraction pattern comprising peaks at 21.2 and 23.8 degrees±0.2 degrees 2-theta, on the 2-theta scale with lambda=1.54 angstroms (Cu Kα).

Aspect 8. The crystalline form of any one of aspects 3-7, characterized by an X-ray powder diffraction pattern comprising peaks at 21.2, 23.8, 27.0, and 32.5 degrees±0.2 degree 2-theta, on the 2-theta scale with lambda=1.54 angstroms (Cu Kα).

Aspect 9. The crystalline form of any one of aspects 3-8, characterized by a differential scanning calorimetry (DSC) thermogram substantially as shown in FIG. 2 when heated at a rate of 10° C./min.

Aspect 10. The crystalline form of any one of aspects 3-9 characterized by a differential scanning calorimetry (DSC) thermogram comprising an endothermic peak at about 244° C. when heated at a rate of 10° C./min.

Aspect 11. The crystalline form of any one of aspects 3-10, characterized by a thermogravimetric analysis profile substantially as shown in FIG. 3 when heated at a rate of 20° C./min.

Aspect 12. The crystalline form of aspect 3, wherein said crystalline that is Formula IA-Form II.

Aspect 13. The crystalline form of aspect 3 or aspect 12, characterized by an X-ray powder diffraction pattern substantially as shown in FIG. 4.

Aspect 14. The crystalline form of any one of aspects 3, 12, or 13, characterized by an X-ray powder diffraction pattern comprising a peak at 25.5 degrees±0.2 degrees 2-theta, on the 2-theta scale with lambda=1.54 angstroms (Cu Kα).

Aspect 15. The crystalline form of any one of aspects 3, or 12-14, characterized by an X-ray powder diffraction pattern comprising peaks at 14.8, 17.5, and 25.5 degrees±0.2 degrees 2-theta, on the 2-theta scale with lambda=1.54 angstroms (Cu Kα).

Aspect 16. The crystalline form of any one of aspects 3, or 12-15, characterized by an X-ray powder diffraction pattern comprising peaks at 14.8, 17.5, 18.4, 24.0, 25.5, 28.0, and 28.7 degrees±0.2 degree 2-theta, on the 2-theta scale with lambda=1.54 angstroms (Cu Kα).

Aspect 17. The crystalline form of any one of aspects 3, or 12-16, characterized by a thermogravimetric analysis profile substantially as shown in FIG. 5 when heated at a rate of 20° C./min.

Aspect 18. The crystalline form of aspect 3, wherein said crystalline that is Formula IA-Form IIa.

Aspect 19. The crystalline form of aspect 3 or aspect 18, characterized by an X-ray powder diffraction pattern substantially as shown in FIG. 6.

Aspect 20. The crystalline form of any one of aspects 3, 18, or 19, characterized by an X-ray powder diffraction pattern comprising a peak at 26.1 degrees±0.2 degrees 2-theta, on the 2-theta scale with lambda=1.54 angstroms (Cu Kα).

Aspect 21. The crystalline form of any one of aspects 3, or 18-20, characterized by an X-ray powder diffraction pattern comprising peaks at 14.0, 14.9, and 26.1 degrees±0.2 degrees 2-theta, on the 2-theta scale with lambda=1.54 angstroms (Cu Kα).

Aspect 22. The crystalline form of any one of aspects 3, or 18-21, characterized by an X-ray powder diffraction pattern comprising peaks at 12.5, 14.0, 14.9, 18.4, and 26.1 degrees±0.2 degree 2-theta, on the 2-theta scale with lambda=1.54 angstroms (Cu Kα).

Aspect 23. The crystalline form of any one of aspects 3, or 18-22, characterized by a differential scanning calorimetry (DSC) thermogram substantially as shown in FIG. 7 when heated at a rate of 10° C./min.

Aspect 24. The crystalline form of any one of aspects 3, or 18-23, characterized by a differential scanning calorimetry (DSC) thermogram comprising an endothermic peak at about 199° C. when heated at a rate of 10° C./min.

Aspect 25. The crystalline form of aspect 3, wherein said crystalline that is Formula IA-Form III.

Aspect 26. The crystalline form of aspect 3 or aspect 25, characterized by an X-ray powder diffraction pattern substantially as shown in FIG. 8.

Aspect 27. The crystalline form of any one of aspects 3, 25, or 26, characterized by an X-ray powder diffraction pattern comprising a peak at 8.1 degrees±0.2 degrees 2-theta, on the 2-theta scale with lambda=1.54 angstroms (Cu Kα).

Aspect 28. The crystalline form of any one of aspects 3, or 25-27, characterized by an X-ray powder diffraction pattern comprising peaks at 8.1 and 23.3 degrees±0.2 degrees 2-theta, on the 2-theta scale with lambda=1.54 angstroms (Cu Kα).

Aspect 29. The crystalline form of any one of aspects 3, or 25-28, characterized by an X-ray powder diffraction pattern comprising peaks at 8.1, 12.5, 13.7, 14.5, 16.2, 18.8, 23.3, and 24.5 degrees±0.2 degree 2-theta, on the 2-theta scale with lambda=1.54 angstroms (Cu Kα).

Aspect 30. The crystalline form of any one of aspects 3, or 25-29, characterized by a differential scanning calorimetry (DSC) thermogram substantially as shown in FIG. 9 when heated at a rate of 10° C./min.

Aspect 31. The crystalline form of any one of aspects 3, or 25-30 characterized by a differential scanning calorimetry (DSC) thermogram comprising an endothermic peak at about 121° C. when heated at a rate of 10° C./min.

Aspect 32. The crystalline form of any one of aspects 3, 25-31, characterized by a thermogravimetric analysis profile substantially as shown in FIG. 10 when heated at a rate of 20° C./min.

Aspect 33. The crystalline form of aspect 3, wherein said crystalline that is Formula IA-Form IV.

Aspect 34. The crystalline form of aspect 3 or aspect 33, characterized by an X-ray powder diffraction pattern substantially as shown in FIG. 11.

Aspect 35. The crystalline form of any one of aspects 3, 33, or 34, characterized by an X-ray powder diffraction pattern comprising a peak at 4.0 degrees±0.2 degrees 2-theta, on the 2-theta scale with lambda=1.54 angstroms (Cu Kα).

Aspect 36. The crystalline form of any one of aspects 3, or 33-35, characterized by an X-ray powder diffraction pattern comprising peaks at 4.0 and 22.7 degrees±0.2 degrees 2-theta, on the 2-theta scale with lambda=1.54 angstroms (Cu Kα).

Aspect 37. The crystalline form of any one of aspects 3, or 33-36, characterized by an X-ray powder diffraction pattern comprising peaks at 4.0, 22.7, and 27.8 degrees±0.2 degree 2-theta, on the 2-theta scale with lambda=1.54 angstroms (Cu Kα).

Aspect 38. The crystalline form of any one of aspects 3, or 33-37, characterized by a differential scanning calorimetry (DSC) thermogram substantially as shown in FIG. 12 when heated at a rate of 10° C./min.

Aspect 39. The crystalline form of any one of aspects 3, or 33-38 characterized by a differential scanning calorimetry (DSC) thermogram comprising an endothermic peak at about 169° C. when heated at a rate of 10° C./min.

Aspect 40. The crystalline form of any one of aspects 3, 33-39, characterized by a thermogravimetric analysis profile substantially as shown in FIG. 13 when heated at a rate of 20° C./min.

Aspect 41. The pharmaceutically acceptable salt of aspect 1, wherein the salt is the phosphate salt, Formula IB.

Aspect 42. A crystalline form of the phosphate salt of aspect 41.

Aspect 43. The crystalline form of aspect 42, wherein said crystalline that is Formula IB-Form I. Aspect 44. The crystalline form of aspect 42 or aspect 43, characterized by an X-ray powder diffraction pattern substantially as shown in FIG. 14A.

Aspect 45. The crystalline form of any one of aspects 42-44, characterized by an X-ray powder diffraction pattern comprising a peak at 24.9 degrees±0.2 degrees 2-theta, on the 2-theta scale with lambda=1.54 angstroms (Cu Kα).

Aspect 46. The crystalline form of any one of aspects 42-45, characterized by an X-ray powder diffraction pattern comprising peaks at 18.2, 19.6, 24.9 degrees±0.2 degrees 2-theta, on the 2-theta scale with lambda=1.54 angstroms (Cu Kα).

Aspect 47. The crystalline form of any one of aspects 42-46, characterized by an X-ray powder diffraction pattern comprising peaks at 18.2, 19.6, 24.9 25.7, and 27.0 degrees±0.2 degree 2-theta, on the 2-theta scale with lambda=1.54 angstroms (Cu Kα).

Aspect 48. The crystalline form of any one of aspects 42-47, characterized by a differential scanning calorimetry (DSC) thermogram substantially as shown in FIG. 15A when heated at a rate of 10° C./min.

Aspect 49. The crystalline form of any one of aspects 42-48 characterized by a differential scanning calorimetry (DSC) thermogram comprising an endothermic peak at about 201° C. when heated at a rate of 10° C./min.

Aspect 50. The crystalline form of any one of aspects 42-49, characterized by a thermogravimetric analysis profile substantially as shown in FIG. 16A when heated at a rate of 20° C./min.

Aspect 51. The crystalline form of aspect 42, wherein said crystalline that is Formula IB-Form II.

Aspect 52. The crystalline form of aspect 42 or aspect 51, characterized by an X-ray powder diffraction pattern substantially as shown in FIG. 14B.

Aspect 53. The crystalline form of any one of aspects 42, or 51-52, characterized by an X-ray powder diffraction pattern comprising a peak at 24.6 degrees±0.2 degrees 2-theta, on the 2-theta scale with lambda=1.54 angstroms (Cu Kα).

Aspect 54. The crystalline form of any one of aspects 42, or 51-53, characterized by an X-ray powder diffraction pattern comprising peaks at 19.3, 24.6, and 27.4 degrees±0.2 degrees 2-theta, on the 2-theta scale with lambda=1.54 angstroms (Cu Kα).

Aspect 55. The crystalline form of any one of aspects 42, or 51-54, characterized by an X-ray powder diffraction pattern comprising peaks at 19.3, 22.3, 23.6, 24.6, and 27.4 degrees±0.2 degree 2-theta, on the 2-theta scale with lambda=1.54 angstroms (Cu Kα).

Aspect 56. The crystalline form of any one of aspects 42, or 51-55, characterized by a differential scanning calorimetry (DSC) thermogram substantially as shown in FIG. 15B when heated at a rate of 10° C./min.

Aspect 57. The crystalline form of any one of aspects 42, or 51-56 characterized by a differential scanning calorimetry (DSC) thermogram comprising an endothermic peak at about 229° C. when heated at a rate of 10° C./min.

Aspect 58. The crystalline form of any one of aspects 42, or 51-57, characterized by a thermogravimetric analysis profile substantially as shown in FIG. 16B when heated at a rate of 20° C./min.

Aspect 59. The pharmaceutically acceptable salt of aspect 1, wherein the salt is the tartrate salt, Formula IC.

Aspect 60. The crystalline form of aspect 59, wherein said tartrate salt is crystalline.

Aspect 61. The crystalline form of aspect 59 or aspect 60, characterized by an X-ray powder diffraction pattern substantially as shown in FIG. 17.

Aspect 62. The crystalline form of any one of aspects 59-61, characterized by an X-ray powder diffraction pattern comprising a peak at 18.4 degrees±0.2 degrees 2-theta, on the 2-theta scale with lambda=1.54 angstroms (Cu Kα).

Aspect 63. The crystalline form of any one of aspects 59-62, characterized by an X-ray powder diffraction pattern comprising peaks at 18.4, 19.9, and 21.5 degrees±0.2 degrees 2-theta, on the 2-theta scale with lambda=1.54 angstroms (Cu Kα).

Aspect 64. The crystalline form of any one of aspects 59-63, characterized by an X-ray powder diffraction pattern comprising peaks at 18.4, 19.4, 19.9, 21.5, and 26.3 degrees±0.2 degree 2-theta, on the 2-theta scale with lambda=1.54 angstroms (Cu Kα).

Aspect 65. The crystalline form of any one of aspects 59-64, characterized by a differential scanning calorimetry (DSC) thermogram substantially as shown in FIG. 18 when heated at a rate of 10° C./min.

Aspect 66. The crystalline form of any one of aspects 59-65 characterized by a differential scanning calorimetry (DSC) thermogram comprising an endothermic peak at about 190° C. when heated at a rate of 10° C./min.

Aspect 67. The crystalline form of any one of aspects 59-66, characterized by a thermogravimetric analysis profile substantially as shown in FIG. 19 when heated at a rate of 20° C./min.

Aspect 68. A pharmaceutical composition comprising a pharmaceutically acceptable salt and/or crystalline form of any one of aspects 1-67, and a pharmaceutically acceptable excipient.

Aspect 69. A method of treating a disease or disorder associated with aberrant PRMT5 activity in a subject comprising administering to the subject, a pharmaceutically acceptable salt and/or crystalline form of any one of aspects 1-67.

Aspect 70. The method of aspect 69, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; spliceosome mutant cancers, glioblastoma, NSCLC, head and neck cancer, bladder cancer, or hepatocellular carcinoma.

What is claimed:

1. A pharmaceutically acceptable salt of a compound of Formula I:

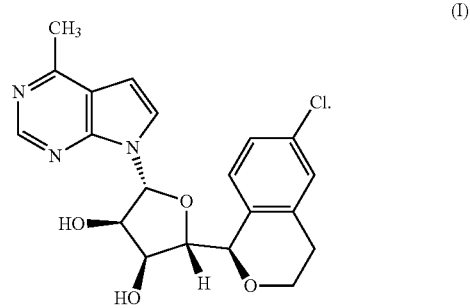 [SMILES: Cc1ncnc2c1ccn2[C@@H]1O[C@H]([C@@H]2OCCc3cc(Cl)ccc32)[C@@H](O)[C@H]1O]

2. The pharmaceutically acceptable salt of claim 1, wherein the salt is the hydrochloride salt, Formula IA

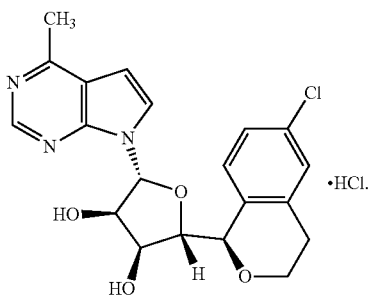

(IA)

3. A crystalline form of the hydrochloride salt of claim 2.

4. The crystalline form of claim 3, wherein said crystalline form is Formula IA-Form I.

5. The crystalline form of claim 3, characterized by an X-ray powder diffraction pattern substantially as shown in FIG. 1.

6. The crystalline form of claim 3, characterized by an X-ray powder diffraction pattern comprising a peak at 23.8 degrees±0.2 degrees 2-theta, on the 2-theta scale with lambda=1.54 angstroms (Cu Kα).

7. The crystalline form of claim 3, characterized by an X-ray powder diffraction pattern comprising peaks at 21.2 and 23.8 degrees±0.2 degrees 2-theta, on the 2-theta scale with lambda=1.54 angstroms (Cu Kα).

8. The crystalline form of claim 3, characterized by an X-ray powder diffraction pattern comprising peaks at 21.2, 23.8, 27.0, and 32.5 degrees±0.2 degree 2-theta, on the 2-theta scale with lambda=1.54 angstroms (Cu Kα).

9. The crystalline form of claim 3, characterized by a differential scanning calorimetry (DSC) thermogram substantially as shown in FIG. 2 when heated at a rate of 10° C./min.

10. The crystalline form of claim 3 characterized by a differential scanning calorimetry (DSC) thermogram comprising an endothermic peak at about 244° C. when heated at a rate of 10° C./min.

11. The crystalline form of claim 3, characterized by a thermogravimetric analysis profile substantially as shown in FIG. 3 when heated at a rate of 20° C./min.

12. The crystalline form of claim 3, wherein said crystalline form is Formula IA-Form II.

13. The crystalline form of claim 3, characterized by an X-ray powder diffraction pattern substantially as shown in FIG. 4.

14. The crystalline form of claim 3, characterized by an X-ray powder diffraction pattern comprising a peak at 25.5 degrees±0.2 degrees 2-theta, on the 2-theta scale with lambda=1.54 angstroms (Cu Kα).

15. The crystalline form of claim 3, characterized by an X-ray powder diffraction pattern comprising peaks at 14.8, 17.5, and 25.5 degrees±0.2 degrees 2-theta, on the 2-theta scale with lambda=1.54 angstroms (Cu Kα).

16. The crystalline form of claim 3, characterized by an X-ray powder diffraction pattern comprising peaks at 14.8, 17.5, 18.4, 24.0, 25.5, 28.0, and 28.7 degrees±0.2 degree 2-theta, on the 2-theta scale with lambda=1.54 angstroms (Cu Kα).

17. The crystalline form of claim 3, characterized by a thermogravimetric analysis profile substantially as shown in FIG. 5 when heated at a rate of 20° C./min.

18. The crystalline form of claim 3, wherein said crystalline form is Formula IA-Form IIa.

19. The crystalline form of claim 3, characterized by an X-ray powder diffraction pattern substantially as shown in FIG. 6.

20. The crystalline form of claim 3, characterized by an X-ray powder diffraction pattern comprising a peak at 26.1 degrees±0.2 degrees 2-theta, on the 2-theta scale with lambda=1.54 angstroms (Cu Kα).

21. The crystalline form of claim 3, characterized by an X-ray powder diffraction pattern comprising peaks at 14.0, 14.9, and 26.1 degrees±0.2 degrees 2-theta, on the 2-theta scale with lambda=1.54 angstroms (Cu Kα).

22. The crystalline form of claim 3, characterized by an X-ray powder diffraction pattern comprising peaks at 12.5, 14.0, 14.9, 18.4, and 26.1 degrees±0.2 degree 2-theta, on the 2-theta scale with lambda=1.54 angstroms (Cu Kα).

23. The crystalline form of claim 3, characterized by a differential scanning calorimetry (DSC) thermogram substantially as shown in FIG. 7 when heated at a rate of 10° C./min.

24. The crystalline form of claim 3, characterized by a differential scanning calorimetry (DSC) thermogram comprising an endothermic peak at about 199° C. when heated at a rate of 10° C./min.

25. The crystalline form of claim 3, wherein said crystalline form is Formula IA-Form III.

26. The crystalline form of claim 3, characterized by an X-ray powder diffraction pattern substantially as shown in FIG. 8.

27. The crystalline form of claim 3, characterized by an X-ray powder diffraction pattern comprising a peak at 8.1 degrees±0.2 degrees 2-theta, on the 2-theta scale with lambda=1.54 angstroms (Cu Kα).

28. The crystalline form of claim 3, characterized by an X-ray powder diffraction pattern comprising peaks at 8.1 and 23.3 degrees±0.2 degrees 2-theta, on the 2-theta scale with lambda=1.54 angstroms (Cu Kα).

29. The crystalline form of claim 3, characterized by an X-ray powder diffraction pattern comprising peaks at 8.1, 12.5, 13.7, 14.5, 16.2, 18.8, 23.3, and 24.5 degrees±0.2 degree 2-theta, on the 2-theta scale with lambda=1.54 angstroms (Cu Kα).

30. The crystalline form of claim 3, characterized by a differential scanning calorimetry (DSC) thermogram substantially as shown in FIG. 9 when heated at a rate of 10° C./min.

31. The crystalline form of claim 3 characterized by a differential scanning calorimetry (DSC) thermogram comprising an endothermic peak at about 121° C. when heated at a rate of 10° C./min.

32. The crystalline form of claim 3, characterized by a thermogravimetric analysis profile substantially as shown in FIG. 10 when heated at a rate of 20° C./min.

33. The crystalline form of claim 3, wherein said crystalline form is Formula IA-Form IV.

34. The crystalline form of claim 3, characterized by an X-ray powder diffraction pattern substantially as shown in FIG. 11.

35. The crystalline form of claim 3, characterized by an X-ray powder diffraction pattern comprising a peak at 4.0 degrees #0.2 degrees 2-theta, on the 2-theta scale with lambda=1.54 angstroms (Cu Kα).

36. The crystalline form of claim 3, characterized by an X-ray powder diffraction pattern comprising peaks at 4.0 and 22.7 degrees±0.2 degrees 2-theta, on the 2-theta scale with lambda=1.54 angstroms (Cu Kα).

37. The crystalline form of claim 3, characterized by an X-ray powder diffraction pattern comprising peaks at 4.0, 22.7, and 27.8 degrees±0.2 degree 2-theta, on the 2-theta scale with lambda=1.54 angstroms (Cu Kα).

38. The crystalline form of claim 3, characterized by a differential scanning calorimetry (DSC) thermogram substantially as shown in FIG. 12 when heated at a rate of 10° C./min.

39. The crystalline form of claim 3 characterized by a differential scanning calorimetry (DSC) thermogram comprising an endothermic peak at about 169° C. when heated at a rate of 10° C./min.

40. The crystalline form of claim 3, characterized by a thermogravimetric analysis profile substantially as shown in FIG. 13 when heated at a rate of 20° C./min.

41. The pharmaceutically acceptable salt of claim 1, wherein the salt is the phosphate salt, Formula IB.

42. A crystalline form of the phosphate salt of claim 41.

43. The crystalline form of claim 42, wherein said crystalline form is Formula IB-Form I.

44. The crystalline form of claim 42, characterized by an X-ray powder diffraction pattern substantially as shown in FIG. 14A.

45. The crystalline form of claim 42, characterized by an X-ray powder diffraction pattern comprising a peak at 24.9 degrees±0.2 degrees 2-theta, on the 2-theta scale with lambda=1.54 angstroms (Cu Kα).

46. The crystalline form of claim 42, characterized by an X-ray powder diffraction pattern comprising peaks at 18.2, 19.6, 24.9 degrees±0.2 degrees 2-theta, on the 2-theta scale with lambda=1.54 angstroms (Cu Kα).

47. The crystalline form of claim 42, characterized by an X-ray powder diffraction pattern comprising peaks at 18.2, 19.6, 24.9 25.7, and 27.0 degrees±0.2 degree 2-theta, on the 2-theta scale with lambda=1.54 angstroms (Cu Kα).

48. The crystalline form of claim 42, characterized by a differential scanning calorimetry (DSC) thermogram substantially as shown in FIG. 15A when heated at a rate of 10° C./min.

49. The crystalline form of claim 42 characterized by a differential scanning calorimetry (DSC) thermogram comprising an endothermic peak at about 201° C. when heated at a rate of 10° C./min.

50. The crystalline form of claim 42, characterized by a thermogravimetric analysis profile substantially as shown in FIG. 16A when heated at a rate of 20° C./min.

51. The crystalline form of claim 42, wherein said crystalline form is Formula IB-Form II.

52. The crystalline form of claim 42, characterized by an X-ray powder diffraction pattern substantially as shown in FIG. 14B.

53. The crystalline form of claim 42, characterized by an X-ray powder diffraction pattern comprising a peak at 24.6 degrees±0.2 degrees 2-theta, on the 2-theta scale with lambda=1.54 angstroms (Cu Kα).

54. The crystalline form of claim 42, characterized by an X-ray powder diffraction pattern comprising peaks at 19.3, 24.6, and 27.4 degrees±0.2 degrees 2-theta, on the 2-theta scale with lambda=1.54 angstroms (Cu Kα).

55. The crystalline form of claim 42, characterized by an X-ray powder diffraction pattern comprising peaks at 19.3, 22.3, 23.6, 24.6, and 27.4 degrees±0.2 degree 2-theta, on the 2-theta scale with lambda=1.54 angstroms (Cu Kα).

56. The crystalline form of claim 42, characterized by a differential scanning calorimetry (DSC) thermogram substantially as shown in FIG. 15B when heated at a rate of 10° C./min.

57. The crystalline form of claim 42 characterized by a differential scanning calorimetry (DSC) thermogram comprising an endothermic peak at about 229° C. when heated at a rate of 10° C./min.

58. The crystalline form of claim 42, characterized by a thermogravimetric analysis profile substantially as shown in FIG. 16B when heated at a rate of 20° C./min.

59. The pharmaceutically acceptable salt of claim 1, wherein the salt is the tartrate salt, Formula IC.

60. A crystalline form of the tartrate salt of claim 59.

61. The crystalline form of claim 60, characterized by an X-ray powder diffraction pattern substantially as shown in FIG. 17.

62. The crystalline form of claim 60, characterized by an X-ray powder diffraction pattern comprising a peak at 18.4 degrees±0.2 degrees 2-theta, on the 2-theta scale with lambda=1.54 angstroms (Cu Kα).

63. The crystalline form of claim 60, characterized by an X-ray powder diffraction pattern comprising peaks at 18.4, 19.9, and 21.5 degrees±0.2 degrees 2-theta, on the 2-theta scale with lambda=1.54 angstroms (Cu Kα).

64. The crystalline form of claim 60, characterized by an X-ray powder diffraction pattern comprising peaks at 18.4, 19.4, 19.9, 21.5, and 26.3 degrees±0.2 degree 2-theta, on the 2-theta scale with lambda=1.54 angstroms (Cu Kα).

65. The crystalline form of claim 60, characterized by a differential scanning calorimetry (DSC) thermogram substantially as shown in FIG. 18 when heated at a rate of 10° C./min.

66. The crystalline form of claim 60 characterized by a differential scanning calorimetry (DSC) thermogram comprising an endothermic peak at about 190° C. when heated at a rate of 10° C./min.

67. The crystalline form of claim 60, characterized by a thermogravimetric analysis profile substantially as shown in FIG. 19 when heated at a rate of 20° C./min.

68. A pharmaceutical composition comprising a pharmaceutically acceptable salt and/or crystalline form of claim 1, and a pharmaceutically acceptable excipient.

69. A method of treating a disease or disorder associated with aberrant PRMT5 activity in a subject comprising administering to the subject, a pharmaceutically acceptable salt and/or crystalline form of claim 1.

70. The method of claim 69, wherein the disease or disorder associated with aberrant PRMT5 activity is breast cancer, lung cancer, pancreatic cancer, prostate cancer, colon cancer, ovarian cancer, uterine cancer, cervical cancer, leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS), epidermoid cancer, hemoglobinopathies such as b-thalassemia and sickle cell disease (SCD), CDKN2A deleted cancers; 9P deleted cancers; MTAP deleted cancers; spliceosome mutant cancers, glioblastoma, NSCLC, head and neck cancer, bladder cancer, hepatocellular carcinoma, adenoid cystic carcinoma (ACC), primary central nervous system lymphoma, fallopian tube cancer, or non-Hodgkin lymphoma.

\* \* \* \* \*